(12) United States Patent
Pan

(10) Patent No.: US 7,060,462 B2
(45) Date of Patent: Jun. 13, 2006

(54) AOPB GENE, PROTEIN, HOMOLOGS, FRAGMENTS AND VARIANTS THEREOF, AND THEIR USE FOR CELL SURFACE DISPLAY

(75) Inventor: Shen Quan Pan, Singapore (SG)

(73) Assignee: National University of Singapore, Singapore (SG)

( * ) Notice: Subject to any disclaimer, the term of this patent is extended or adjusted under 35 U.S.C. 154(b) by 84 days.

(21) Appl. No.: 10/415,554

(22) PCT Filed: Nov. 1, 2001

(86) PCT No.: PCT/SG01/00228

§ 371 (c)(1),
(2), (4) Date: Aug. 14, 2003

(87) PCT Pub. No.: WO02/36777

PCT Pub. Date: May 10, 2002

(65) Prior Publication Data

US 2004/0076976 A1    Apr. 22, 2004

Related U.S. Application Data

(60) Provisional application No. 60/244,902, filed on Nov. 2, 2000.

(51) Int. Cl.
*C12P 21/06* (2006.01)
(52) U.S. Cl. .................... 435/69.1; 530/350; 435/71.1
(58) Field of Classification Search ................. 530/350; 514/12; 435/69.1, 7.1, 6, 252.34, 7; 424/260.1, 424/184.1, 185.1, 69.1
See application file for complete search history.

(56) References Cited

U.S. PATENT DOCUMENTS

| 3,791,932 A | 2/1974 | Schuurs et al. |
| 3,949,064 A | 4/1976 | Bornstein et al. |
| 4,174,384 A | 11/1979 | Ullman et al. |
| 4,554,101 A | 11/1985 | Hopp |
| 4,882,278 A | 11/1989 | Mekalanos |
| 4,952,496 A | 8/1990 | Studier et al. |
| 5,028,530 A | 7/1991 | Lai et al. |
| 5,348,867 A | 9/1994 | Georgiou et al. |
| 5,516,637 A | 5/1996 | Huang et al. |
| 5,866,344 A | 2/1999 | Georgiou |
| 5,955,090 A * | 9/1999 | Knapp et al. ............ 424/260.1 |
| 6,190,662 B1 | 2/2001 | Steidler et al. |
| 6,274,345 B1 | 8/2001 | Lee et al. |
| 6,300,065 B1 | 10/2001 | Kieke et al. |

FOREIGN PATENT DOCUMENTS

WO    WO 88/06626 A1    9/1988

(Continued)

OTHER PUBLICATIONS

Cloeckaert et al., NCBI Entry Accession No. U33003.*

(Continued)

*Primary Examiner*—Jon Weber
*Assistant Examiner*—Robert B. Mondesi
(74) *Attorney, Agent, or Firm*—Birch, Stewart, Kolasch & Birch, LLP

(57) ABSTRACT

The present invention provides an *Agrobacterium tumefaciens* outer membrane protein designated aopB, its variants, homologs and fragments and corresponding DNA molecules. The invention also relates to a method whereby aopB.related proteins are used as carriers to display passenger proteins on the surface of bacteria. Display of the passenger protein permits applicatins such as live vaccine development, library screening, protein purification, biodecontainment, and whole cell catalysis.

44 Claims, 13 Drawing Sheets

FOREIGN PATENT DOCUMENTS

| WO | WO 90/00594 A2 | 1/1990 |
| --- | --- | --- |
| WO | WO 91/13157 A1 | 9/1991 |
| WO | WO 92/01796 A1 | 2/1992 |
| WO | WO 92/11354 A1 | 7/1992 |
| WO | WO 92/11361 A1 | 7/1992 |
| WO | WO 92/21376 A1 | 12/1992 |
| WO | WO 93/24636 * | 12/1993 |
| WO | WO 94/01533 A1 | 1/1994 |
| WO | WO 94/19482 A1 | 9/1994 |

OTHER PUBLICATIONS

Bowers, T. J et al., NCBI Entry Accession No. AF001274.*
Agterberg et al., Gene, vol. 59, pp. 145-150, (1987).
Altschul et al., J. Mol. Biol., vol. 215, pp. 403-410, (1990).
Altschul et al., Nucleic Acids Research, vol. 25, No. 17, pp. 3389-3402, (1997).
Andreoni et al., BioTechniques, vol. 23, No. 4, pp. 696-704, (Oct. 1997).
Bachrach et al., Microbiology, vol. 146, pp. 297-303, (2000).
Bardwell et al., Cell, vol. 67, pp. 581-589, (Nov. 1, 1991).
Berger et al., Journal of Bacteriology, vol. 176, No. 12, pp. 3646-3660, (Jun. 1994).
Brickman et al., Journal of Molecular Biology, vol. 96, pp. 307-316, (1975).
Burnett et al., Vaccine, vol. 19, pp. 735-742, (2001).
Cangelosi et al., Methods in Enzymology, vol. 204, pp. 384-397, (1991).
Charbit et al., Embo. J., vol. 5, No. 11, pp. 3029-3037, (Nov. 1986).
Charles et al., Journal of Bacteriology, vol. 175, No. 20, pp. 6614-6625, (Oct. 1993).
Chen et al., Journal of Bacteriology, vol. 173, No. 3, pp. 1139-1144, (Feb. 1991).
Daugherty et al., Protein Engineering, vol. 12, No. 7, pp. 613-621, (1999).
Daugherty et al., Protein Engineering, vol. 11, No. 9, pp. 825-832, (1998).
De Maagd et al., Journal of Bacteriology, vol. 167, No. 3, pp. 1083-1085, (Sep. 1986).
Dehio et al., Gene, vol. 215, pp. 223-229, (1998).
Devereux et al., Nucleic Acids Research, vol. 12, No. 1, pp. 387-395, Jan. 1984.
Ditta et al., Proc. Natl. Acad. Sci. USA, vol. 77, No. 12, pp. 7347-7351, Dec. 1980.
Earhart, Methods in Enzymology, vol. 326, pp. 506-516, (2000).
Ekaza et al., Microbiology, vol. 146, pp. 1605-1616, (2000).
Enderle, Biotechniques, vol. 25, No. 6, pp. 954-958, (1998).
Finan et al., J. Bacteriol, vol. 167, No. 1, pp. 66-72, (Jul. 1986).
Flynn, Cellular and Molecular Biology, vol. 40, pp. 31-36, (1994).
Francisco et al., Proc. Natl. Acad. Sci. USA, vol. 89, pp. 2713-2717, (Apr. 1992).
Freudl et al., J. Mol. Biol., vol. 188, No. 3, pp. 491-494, (Apr. 1986).
Garg et al., Applied and Environmental Microbiology, vol. 65, No. 6, pp. 2802-2804, (Jun. 1999).
Giddings et al., Theor. Appl. Genet., vol. 100, pp. 820-823, (2000).
Glazebrook et al., Methods in Enzymology, vol. 204, pp. 398-418, (1991).
Gregorovic et al., Food Technology and Biotechnology, vol. 39, No. 1, pp. 49-53, (2001).
Hanes et al., Proc. Natl. Acad. Sci. USA, vol. 94, pp. 4937-4942, (May 1997).
Hansen et al., Journal Bacteriology, vol. 174, No. 16, pp. 5442-5449 (Aug. 1992).
Hatterman et al., Applied and Environmental Microbiology, vol. 56, No. 4, pp. 833-836, (Apr. 1990).
Hayashi et al., Journal of Bioscience and Bioengineering, vol. 89, No. 6, pp. 550-553, (2000).
High et al., EMBO, vol. 11, No. 5, pp. 1991-1999, (1992).
Hinds et al., Microbiology, vol. 145, pp. 519-527, (1999).
Inoue et al., Gene, vol. 96, pp. 23-28, (1990).
Jacobs et al., Gene, vol. 83, pp. 95-103, (1989).
Jia et al., Gene, vol. 284, pp. 113-124, (2002).
Jubier-Maurin et al., Infection and Immunity, vol. 69, No. 8, pp. 4823-4830, (2001).
Jung et al., Nature Biotechnology, vol. 16, pp. 576-580, (Jun. 1998).
Kamitani et al., EMBO, vol. 11, No. 1, pp. 57-62, (1992).
Karlin et al., Proc. Natl. Acad. Sci. USA, vol. 87, pp. 2264-2268, (Mar. 1990).
Karlin et al., Proc. Natl. Acad. Sci. USA, vol. 90, pp. 5873-5877, (Jun. 1993).
Kim et al., Applied Biochemistry and Biotechnology, vol. 73, pp. 81-88, (1998).
Kim et al., Letters in Applied Microbiology, vol. 29, pp. 292-297, (1999).
Kim et al., Applied and Environmental Microbiology, vol. 66, No. 2, pp. 788-793, (Feb. 2000).
Klauser et al., EMBO, vol. 9, No. 6, pp. 1991-1999, (1990).
Lee et al., Nature Biotechnology, vol. 18, pp. 645-648, (Jun. 2000).
Li et al., FEMS Microbiology Letters, vol. 179, pp. 141-146, (1999).
Marciel et al., Infection and Immunity, vol. 69, No. 10, pp. 6231-6239, Oct. 2001).
Medaglini et al., Proc. Natl. Acad. Sci. USA, vol. 92, pp. 6868-6872, (Jul. 1995).
Oh et al., Journal of Bacteriology, vol. 179, No. 1, pp. 122-127, (Jan. 1997).
Pan et al., Molecular Microbiology, vol. 17, No. 2, pp. 259-269, (1995).
Panda et al., J. Biosci., vol. 20, No. 3, pp. 367-376, (Jun. 1995).
Roest et al., Molecular Plant-Microbe Interactions, vol. 8, No. 4, pp. 576-583, (1995).
Rosenberg et al., Mol. Gen. Genet., vol. 196, pp. 533-536, (1984).
Shi et al., Enzyme and Microbial Technology, vol. 28, pp. 25-34, (2001).
Sizemore et al., Science, vol. 270, pp. 299-302, (Oct. 1995).
Stathopoulos et al., Appl. Microbiol Biotechnol, vol. 45, pp. 112-119, (1996).
Steidler et al., Applied and Environmental Microbiology, vol. 64, No. 1, pp. 342-345, (Jan. 1998).
Suarez et al., Gene, vol. 196, pp. 69-74, (1997).
Suzuki et al., Journal of Biological Chemistry, vol. 270, No. 52, pp. 30874-30880, (1995).
Tang et al., FEMS Microbiology Letters, vol. 179, pp. 37-42, (1999).
Tommassen et al., J. Bacteriol., vol. 157, pp. 327-329, (Jan. 1984).
Vaughan et al., Nat. Biotechnol., vol. 14, No. 3, pp. 309-314, (Mar. 1996).
Watson et al., J. Bacteriol., vol. 123, No. 1, pp. 255-264, (Jul. 1975).

Windsor et al., Medical Microbiology Letters, vol. 2, No. 4, pp. 159-167, (Jun. 15, 1993).

Winter et al., Nature, vol. 349, pp. 293-299, (Jan. 1991).

Yarosh et al., Mol. Microbiol., vol. 3, No. 6, pp. 813-823, (Jun. 1989).

Genbank Accession No. AE008132. Oct. 17, 2001. Hinkle G, et al. *Agrobacterium tumefaciencs* strain C58 circular chromosome, section 190 of 254 of the complete sequence. Relevant to SEQ ID No. 2.

Genbank Accession No. AAK86934 Aug. 14, 2001. Hinkle G, et al. *Agrobacterium tumefaciencs*. Relevant to SEQ ID No. 1.

Swiss Prot Accession No. Q52866. Dec. 15, 1998, Roest HP et al. 22KD outer membrane protein precursor. Relevant to SEQ ID No. 2.

Genbank Accession No. AJ006231. Sep. 7, 1998. Priefert H, et al. Pseudomonas sp. calB gene.

* cited by examiner

Fig. 1A.

```
        NheI
1       CTAGCTGTCACTCAGCTCCAAAAGAATTGGGCGATTTTTCATTCACAATGCAATTTCGGT
61      TTAATTTGAATATAACTAAGTTTAAAGGCGATCTATTGCTGGTTAGGCTTCTGTTAGGGT
121     TAATATAACCCTTGTGGCAATTAGGCAACGTCTAATTCTAGTCACGTCTCTGCCCCAAAC
181     AATTCACATTTTGGCTCTTTGATCTCCGCATTCTCCCATCAAGTTCAGTTTCCAGAGGGG
241     CAAATTAACCCGACGATTTTTACCGCGTCTGAAAACAATGTTTTGAGTGCAGAGCGGTCC
301     TGAAAGGAGAATAACATGCGTATTTTCGTAGCAACCCTTATGGCTTCGACCATGGCAGCC
                       M   R   I   F   V   A   T   L   M   A   S   T   M   A   A
361     GCCGGTTTTTCGGCTGCTTACGCCGCCGACGCCGTAAATGAGGTGCCGCAGGCACCGGTA
         A   G   F   S   A   A   Y   A   A   D   A   V   N   E   V   P   Q   A   P   V
421     GCCTACGACCAGCCCGCCGCGGTCAAGGATTGGTCCGGCGCCTACCTCGGTGGTACGGTC
         A   Y   D   Q   P   A   A   V   K   D   W   S   G   A   Y   L   G   G   T   V
481     AACTATGACTGGGGCCGTTTCAGCTCCAGCAATGACGGTCGTGACGCCAAGGGCTTCGGT
         N   Y   D   W   G   R   F   S   S   S   N   D   G   R   D   A   K   G   F   G
541     GGCGGCGTCTATGGTGGTTACAACATGCAGAGCGGCCAGATCGTTTACGGTGCTGAAGCA
         G   G   V   Y   G   G   Y   N   M   Q   S   G   Q   I   V   Y   G   A   E   A
601     GACGTGAACATGGGCGACGAGAAGGGCTCCGCCGGTACGGTTGCCGGTCGCGCCGTCGAA
         D   V   N   M   G   D   E   K   G   S   A   G   T   V   A   G   R   A   V   E
661     GGCAAGCAGGGCGTCAACGGCTCGCTGCGTGGCCGCGTCGGTTACGACATGAACCCGTTC
         G   K   Q   G   V   N   G   S   L   R   G   R   V   G   Y   D   M   N   P   F
721     CTGCTTTATGGTACGGCCGGTCTTGCTGTCTCCGACAACAAGGTTCGTGACGGCGTCAAC
         L   L   Y   G   T   A   G   L   A   V   S   D   N   K   V   R   D   G   V   N
781     AAGGACAGCGCCACGGCTCTCGGTTACACGGTTGGTGCCGGTGTTGAAGCCATGGTGACC
         K   D   S   A   T   A   L   G   Y   T   V   G   A   G   V   E   A   M   V   T
841     GACAACATCACCGCTCGTCTGGAATATCGCTACAGCGATTACCAGAAGAAGGACTACACG
         D   N   I   T   A   R   L   E   Y   R   Y   S   D   Y   Q   K   K   D   Y   T
901     CTCGGCAACGATGCCTTCTCGCGTGGTTTTGACGACCACTCGGTCAAGGCCGGTATCGGC
         L   G   N   D   A   F   S   R   G   F   D   D   H   S   V   K   A   G   I   G
961     GTCAAGTTCTGATCCTTCTCGGATCGGTCAAGGAAAAGCCGGGGTTTACGCCCCGGCTTT
         V   K   F
1021    TTTTTGTTTCTGTGATTTGCCATCGCCTTAACGCCCGGTGGAAAGAACCGGGCGTTTTGT
1081    TCGGCGGGTCTAGGCGGCGGCTTTCATTTCCGCATAGGCGTCGAAACGCTTGCCGAAGGT
1141    TTCTGGCCAGGCTGCCAGCGCATCACGTCCCTCGGCCCACTCACCGGCAAAACGCAGGTC
1201    GAGATAGCCGATCATCGCTGCAAGGGCGAAATGGCCGCCATGCAGCTTCTTGCCGGTTTT
1261    CGGCAGGTTGGCGTTGAGGTGATCGAGCCCGCGGACCACCTTGCTCCACTGCTTGTCGAT
1321    CCACGGCTGATGAATCTTGTCTTCCGGGCGGAAACGCCGCTCGTAGACGATGGCGAGCAG
1381    GCAATCCATGATGCCGTCGCACAGAGCTTCCAGAATTTCCGCTTCAGTGCGCTAG
                                                                       NheI
```

Fig. 2.

```
             10         20         30         40         50
AopB   1  MRIFVATLMA STMAAAGFSA AYAADAVNEV POAPVAYDQP A-AVKDWSGA  50
RopB   1  MRVLIAGLMA SVFAIAGVSA AQAADRVDQV PEAPVQEAP  VKPAGSWEGF  50
             60         70         80         90        100
AopB  51  YLGGTVNYDW GRESSSNDGR DAKGFGGGVY GGYNMQSGQI VYGAEADVNM 100
RopB  51  YLGGAGTYNM CDEGS---DR HTYGFGGQVF TGYNWQQGQI VYGVESDLGY 100
            110        120        130        140        150
AopB 101  GDEKGSAGTV AGRAVEGKQG VNGSLRGRVG TDMNPFLIYC TAGLAVSDNK 150
RopB 101  SGDDVSSG-- ---GVENKYG WNGSVRGRVG TDMNPFLIYC TAGLAIGDVK 150
            160        170        180        190        200
AopB 151  VRDGVNKDSA TALGYTVGAC VEAMVIDNIT ARLEYRYSDY QKKDYTLGND 200
RopB 151  VSDDTSDESK TNFGYTVGAC VEAFVINNIT TRLEYRYTDY CSKDYDLDSG 200
            210        220        230        240        250
AopB 201  AFSRGFDDHS VKAGIGVKE                                   250
RopB 201  SESRGYDENS VKLGIGVKE                                   250
```

Sequence of the multiple cloning site (MCS):

```
              HindIII              PstI            KpnI
---atg---gaa GCT TGC TAG CTG CTG CAG GAT CCG GTA CC---
 aopB(1-516)     NheI            BamHI
```

AOPB GENE, PROTEIN, HOMOLOGS, FRAGMENTS AND VARIANTS THEREOF, AND THEIR USE FOR CELL SURFACE DISPLAY

REFERENCE TO RELATED APPLICATIONS

This application is the national phase under 35 U.S.C. § 371 of PCT International Application No. PCT/SG01/00228 which has an International filing date of Nov. 1, 2001, which designated the United States of America.

This application claims the benefit of U.S. Provisional Application No: 60/244,902 filed Nov. 2, 2000; the content of which is herein incorporated by reference.

FIELD OF INVENTION

The present invention relates to the AopB outer membrane protein of *Agrobacterium tumefaciens*, its variants, homologs and fragments and corresponding DNA molecules, which can be used for bacterial cell surface display of proteins.

BACKGROUND OF THE INVENTION

Molecular display technologies have been developed, to construct and screen polypeptide and antibody display libraries and to develop recombinant vaccines, adsorbents, recombinant biocatalysts, and solid phase reagents for diagnostic and analytical purposes. The concept of molecular display technology is the provision of a physical linkage between genotype (e.g., antibody variable region genes) and phenotype (e.g., antigen-binding) to allow simultaneous selection of the genes that encode a protein with the desired function (e.g., binding).

Phage display has been used to probe polypeptide-ligand interactions and extensively for the isolation of high-affinity proteins, including antibodies (Winter G, Milstein C. 1991. Man-made antibodies. Nature 349: 293–299; Vaughan T. J., Williams A. J., Pritchard K., Osbourn J. K., Pope A. R., Earnshaw J. C., McCafferty J., Hodits R. A., Wilton J., Johnson K. S. 1996. Human antibodies with sub-nanomolar affinities isolated from a large non-immunized phage display library. Nat Biotechnol 14: 309–314). Phage libraries are typically screened using repeated cycles of phage capture and elution from an immobilized ligand followed by phage amplification in bacteria. A display technology wherein polypeptides are physically linked in vitro to their coding RNA through a ribosome was recently described (Hanes J., Pluckthun A. 1997. In vitro selection and evolution of functional proteins by using ribosome display. Proc Natl Acad Sci USA 94: 4937–42). However, both phage and ribosome used in these two technologies cannot self-replicate and are too small to be assisted by the powered cell sorting technology, such as fluorescence-activated cell sorting (FACS).

FACS can facilitate high throughput and quantitative screening of protein or antibody libraries displayed on the surface of bacteria, because the relatively large sizes of bacterial cells can allow the system to pick up the clones that bind to fluorescently labeled ligands with high affinity and specificity (Daugherty P S, Olsen M J, Iverson B L, Georgiou G. 1999. Development of an optimized expression system for the screening of antibody libraries displayed on the *Escherichia coli* surface. Protein Eng. 12: 613–21; Steidler L; Viaene J; Fiers W; Remaut E. 1996. Functional display of a heterologous protein on the surface of *Lactococcus lactis* by means of the cell wall anchor of *Staphylococcus aureus* protein A. Immunotechnology. 2: 97–102; Andreoni C, Goetsch L, Libon C, Samuelson P, Nguyen T N, Robert A, Uhlen M, Binz H, Stahl S. 1997. Flow cytometric quantification of surface-displayed recombinant receptors on staphylococci. Biotechniques. 23: 696–702, 704). With current high-speed cell sorters, $10^8$ cells can be screened quantitatively in 1 h, a throughput similar to that obtained in phage library selections. Thus, cell surface display coupled with FACS provides an important alternative display technology for protein engineering. Phage display formats designed for sensitive affinity selections rely upon a single molecular binding event or monovalent display through gpIII fusions. In contrast, cell surface formats achieve typically $10^4$–$10^5$ copies per cell. Consequently, stochastic variations in stability or expression level do not interfere with cell surface library selections.

Bacterial surface display systems have been developed since small peptides fused onto some outer membrane proteins, such as OmpA, LamB, and PhoE, were found to be directed to the *Escherichia coli* cell surface (Charbit A, Boulain J. C, Ryter A, Hofnung M. 1986. Probing the topology of a bacterial membrane protein by genetic insertion of a foreign epitope: expression at the cell surface. EMBO J. 5: 3029–37; Freudl R, MacIntyre S, Degen M, Henning U. 1986. Cell surface exposure of the outer membrane protein OmpA of *Escherichia coli* K-12. J Mol Biol. 188: 491–494; Agterberg M, Adriaanse H, Tommassen J. 1987. Use of outer membrane protein PhoE as a carrier for the transport of a foreign antigenic determinant to the cell surface of *Escherichia coli* K-12. Gene. 59: 145–50). One of the most intriguing applications of expressing proteins on bacterial cell surface is to develop live bacterial vaccines. Presentation of antigens on bacterial cell surface is considered to be advantageous since the surface-exposed antigens might be better recognized by the immune systems. Moreover, the outer membrane lipopolysaccharides can enhance the immune response and may serve as an adjuvant for surface-anchored polypeptides (Lee J. S., Shin K. S., Pan J. G., and Kim C. J. 2000. Surface-displayed viral antigens on *Salmonella* carrier vaccine. Nat. Biotechnol. 18: 645–648). Further, bacteria are easy to be manipulated and inexpensive to be manufactured and distributed. Successful examples of producing new recombinant vaccines have been reported (Kim E J; Yoo S K. 1999. Cell surface display of hepatitis B virus surface antigen by using *Pseudomonas syringae* ice nucleation protein. Lett Appl Microbiol 29: 292–297; Lee J. S., Shin K. S., Pan J. G., and Kim C. J. 2000. Nat. Biotechnol. 18: 645–648). Other applications of bacterial surface display systems include the production of whole-cell adsorbents for bioremediation and novel biocatalysts (Kim Y S.; Jung H C; Pan J G. 2000. Bacterial cell surface display of an enzyme library for selective screening of improved cellulase variants. Appl Environ Microbiol. 66: 788–793; Jung H C; Lebeault J M; Pan J G. 1998. Surface display of *Zymomonas mobilis* levansucrase by using the ice-nucleation protein of *Pseudomonas syringae*. Nat Biotechnol. 16: 576–80).

The commonly used Lpp-OmpA surface display system includes three parts: the signal sequence and first nine N-terminal amino acids of the mature major *E. coli* lipoprotein (Lpp), amino acids 46–159 of *E. coli* outer membrane protein OmpA, and the passenger protein (Francisco J A, Earhart C F, Georgiou G. 1992. Transport and anchoring of beta-lactamase to the external surface of *Escherichia coli*. Proc Natl Acad Sci USA. 89: 2713–2717). This system has been successfully used to display β-lactamase (Francisco J A, Earhart C F, Georgiou G. 1992. Proc Natl Acad Sci USA. 89: 2713–2717), green fluorescent protein (Shi, Huidong; Su, Wei Wen. 2001. Display of green fluorescent protein on *Escherichia coli* cell surface. Enzyme and Microbial Technology. 28: 25–34), single chain Fv (scFv) libraries (Daugherty P S; Chen G; Olsen M J; Iverson B L, Georgiou G. 1998. Antibody affinity maturation using bacterial surface display. Protein Eng. 11: 825–32; Daugherty P S, Olsen M J, Iverson B L, Georgiou G. 1999. Development of an optimized expression system for the screening of antibody libraries displayed on the *Escherichia coli* surface. Protein Eng. 12: 613–21) and recently the HIV-reverse transcriptase (Burnett M S, Wang N. Hofmann M, Kitto G B. 2001. Potential live vaccines for HIV. Vaccine. 19: 735–742). However, this system has limitations: (1) The cell viability is much lower when the Lpp-OmpA is under a constitutive expression condition; thus it is critical to use a tightly regulatory system and an appropriate plasmid of low copy number to optimize the display, especially for large passenger proteins (Daugherty P S, Olsen M J, Iverson B L, Georgiou G. 1999. Development of an optimized expression system for the screening of antibody libraries displayed on the *Escherichia coli* surface. Protein Eng. 12: 613–21; Earhart C. F. 2000. Use of an Lpp-OmpA fusion vehicle for bacterial surface display. Methods Enzymol. 326: 506–516). (2) This system cannot display a dimeric protein like bacterial alkaline phosphatase (PhoA) (Stathopoulos C, Georgiou G, Earhart C F. 1996. Characterization of *Escherichia coli* expressing an Lpp'OmpA(46–159)-PhoA fusion protein localized in the outer membrane. Appl Microbiol Biotechnol. 45: 112–119). The function of PhoA requires the formation of disulfide bridges, which is not spontaneous but catalyzed at least at the disulfide bond formation step (Bardwell J C, McGovern K, Beckwith J. 1991. Identification of a protein required for disulfide bond formation in vivo. Cell 67: 581–589; Kamitani S, Akiyama Y, Ito K. 1992. Identification and characterization of an *Escherichia coli* gene required for the formation of correctly folded alkaline phosphatase, a periplasmic enzyme. EMBO J 11: 57–62).

Many active proteins and enzymes are of multi-subunit nature; and many require disulfide bridges for intra- and inter-molecular interactions. The formation of disulfide bonds and protein folding of passenger proteins in the periplasmic space can hinder the successful display of these proteins. Thus, reducing agents have been added into the culturing medium to increase the efficiency of translocation of CtxB domain and PhoA (Klauser T, Pohlner J, Meyer T F. 1990. Extracellular transport of cholera toxin B subunit using Neisseria IgA protease beta-domain: conformation-dependent outer membrane translocation. EMBO J. 9: 1991–1999; Stathopoulos et al., 1996; Suzuki T, Lett M C, Sasakawa C. 1995. Extracellular transport of VirG protein in Shigella. J Biol Chem. 270: 30874–30880). However, addition of reducing agents in the growth medium can break up the-disulfide bonds required for intra- and inter-molecular interactions. This may interfere with the activity and/or display of some enzymes or proteins; it may also alter the bacterial growth and gene expression, in addition to increasing the operation costs, particularly for large-scale applications.

References relevant to cell surface display technology include: U.S. Pat. No. 5,348,867, U.S. Pat. No. 5,516,637, U.S. Pat. No. 5,866,344, U.S. Pat. No. 6,274,345, U.S. Pat. No. 6,300,065, and U.S. Pat. No. 6,190,662.

SUMMARY OF THE INVENTION

One aspect of the present invention provides a nucleic acid molecule comprising a nucleic acid sequence which encodes a polypeptide selected from any one of:
(a) SEQ ID No: 2;
(b) a fragment comprising at least 39 consecutive amino acids from the N-terminus of SEQ ID No: 2; and
(c) a variant of (a) or (b), which is (i) at least 65% identical in amino acid sequence to the corresponding polypeptide of (a) or (b); and (ii) an outer membrane protein when the variant is produced in a Gram-negative bacterium.

The fragment comprising at least 39 consecutive amino acids from the N-terminus of SEQ ID No: 2 may comprise at least the N-terminal region of SEQ ID No:2. Embodiments of the invention include fragments of at least 125, 134, 172, 183, 207 amino acids of the N-terminal region of SEQ ID No:2.

Another aspect of the invention provides a nucleic acid molecule comprising a nucleic acid sequence which encodes a polypeptide selected from any one of:
(a) SEQ ID No: 4;
(b) a fragment comprising at least 16 consecutive amino acids from the N-terminus of SEQ ID No: 4; and
(c) a variant of (a) or (b) which is (i) at least 65% identical in amino acid sequence to the corresponding polypeptide of (a) or (b); and, (ii) an outer membrane protein when the variant is: (1) joined in-frame with a bacterial secretion signal and a targeting signal and, (2) is produced in a gram-negative bacterium.

The fragment comprising at least 16 consecutive amino acids from the N-terminus of SEQ ID No: 4 may comprise at least the N-terminal region of SEQ ID No:2. Embodiments of the invention include fragments of at least,102, 111, 149, 160, 184 amino acids of the N-terminal region of SEQ ID No:2.

Another aspect of the invention provides a nucleic acid sequence which encodes a fusion protein, said fusion protein comprising a first polypeptide encoded by a nucleic acid molecule of the invention and a second polypeptide. In one embodiment, the second polypeptide is fused to the C-terminus of the first polypeptide.

Another aspect of the invention provides an *Agrobacterium* promoter comprising nucleotides 6 to 309 of SEQ ID No: 1.

Another aspect of the invention provides an isolated nucleic acid probe of 5 to 100 nucleotides or a primer of 10 to 40 nucleotides which hybridizes under stringent conditions to the nucleic acid molecule of SEQ ID No: 1 or 3, or to a complementary sequence of said nucleic acid molecule.

Another aspect of the invention provides an expression vector comprising the nucleic acid molecule of the invention, operably linked to one or more expression control sequences. In one embodiment, the expression control sequences comprise the aopB promoter. In another embodiment, the vector is an expression vector in *E. coli*, wherein the expression control sequences are suitable for expressing the nucleic acid molecule in *E. coli*. In another embodiment, the vector is an expression vector in *Agrobacterium*, wherein the expression control sequences are suitable for expressing the nucleic acid molecule in *Agrobacterium*, preferably *A. tumefaciens*.

Another aspect of the invention provides a recombinant microorganism transformed with the nucleic acid molecule or expression vector of the invention. In one embodiment, the recombinant microorganism displays on its surface the polypeptide or the fusion protein of the invention.

Another aspect of the invention provides a polypeptide comprising an amino acid sequence selected from any one of:
(a) SEQ ID No: 2;
(b) a fragment comprising at least 39 consecutive amino acids from the N-terminus of SEQ ID No: 2; and
(c) a variant of (a) or (b) which is (i) at least 65% identical in amino acid sequence to the corresponding polypeptide of (a) or (b); and (ii) an outer membrane protein when the variant is produced in a gram-negative bacterium.

Another aspect of the invention-provides polypeptide comprising an amino acid sequence selected from any one of:
(a) SEQ ID No: 4;
(b) a fragment comprising at least 16 consecutive amino acids from the N-terminus of SEQ ID No: 4; and
(c) a variant of (a) or (b) which is (i) at least 65% identical in amino acid sequence to the corresponding polypeptide of (a) or (b); and, (ii) an outer membrane protein when the variant is: (1) joined in-frame with a bacterial secretion signal and, (2) is produced in a Gram-negative bacterium.

Another aspect of the invention provides a method for producing the polypeptide or fusion protein of the invention, the method comprising the step of culturing a microorganism transformed with an expression vector comprising the nucleic acid molecule encoding the polypeptide or fusion protein of the invention, the nucleic acid being operably linked to one or more expression control sequences.

Another aspect of the invention provides an antibody specifically reactive against the polypeptide of the invention or against the carrier protein in the fusion protein of of the invention. In one embodiment, the antibody is a monoclonal antibody.

Another aspect of the invention provides a method of producing a microorganism on whose surface is displayed a passenger protein, the method comprising the steps of:
(1) introducing an expression vector into a microorganism; and
(2) culturing the microorganism obtained from step (1) to express the protein;

The expression vector in the display method comprises:
(a) a nucleic acid encoding a carrier protein, wherein the carrier protein is selected from the group consisting of: the polypeptide of the invention, specifically those related to AopB, and a member of the AopB-related outer membrane protein family; wherein the carrier protein is display-compatible with the microorganism and wherein the carrier protein contains a bacterial secretion signal functional in the microorganism;
(b) a nucleic acid encoding a passenger protein, which nucleic acid being joined in frame with, and 3' of, the nucleic acid encoding the carrier protein; and
(c) expression control sequences operably linked to the nucleic acid encoding the carrier protein, wherein the expression control sequences are suitable for expressing the nucleic acid encoding the carrier protein in the microorganism.

In one embodiment, the expression control sequences comprise the aopB promoter. In another embodiment, the microorganism used in the display method is cultured under acidic pH conditions.

In another embodiment, the carrier protein and the microorganism of the display method are selected from the group consisting of:
(a) the carrier protein which is an AopB-related polypeptide, a fragment or variant thereof, and the display-compatible microorganism which is *Agrobacterium*,
(b) the carrier protein which comprises 150 to 220 consecutive amino acids from the N-terminus of the RopB polypeptide sequence and the display-compatible microorganism which is *Rhizobium*,
(c) the carrier protein which comprises 150 to 220 consecutive amino acids from the N-terminus of an outer membrane protein sequence of *Brucella* and the display-compatible microorganism which is *Brucella*,
(d) the carrier protein which comprises 150 to 220 consecutive amino acids from the N-terminus of the Pap31 polypeptide sequence and the display-compatible microorganism which is *Bartonella*,
(e) the carrier protein which comprises 150 to 220 consecutive amino acids from the N-terminus of the PomA polypeptide sequence and the display-compatible microorganism which is *Pasteurella* (*Mannheimia*),
(f) the carrier protein which comprises 150 to 220 consecutive amino acids from the N-terminus of the PPE polypeptide sequence and the display-compatible microorganism which is *Mycobacterium*,
(g) the carrier protein which comprises 150 to 220 consecutive amino acids from the N-terminus of the major outer membrane protein sequence and the display-compatible microorganism which is *Haemophilus*, and
(h) the carrier protein which comprises 150 to 220 consecutive amino acids from the N-terminus of the outer membrane porin polypeptide sequence and the display-compatible microorganism which is *Vibrio*.

In a preferred embodiment, the secretion signal which functions with the carrier protein to display the passenger protein comprises amino acids 1 to 23 of SEQ ID No:2. In a further preferred embodiment, the microorganism is *Agrobacterium tumefaciens*.

The display method of the invention may further comprise the step of assaying the cultured microorganism for the presence of the passenger protein on the surface of the microorganism and selecting those organisms with the passenger protein on the surface. In one embodiment, the assay method comprises fluorescence-activated cell sorting (FACS).

Another aspect of the invention provides a method for expressing a fusion protein on the surface of *Agrobacterium*, the method comprising the steps of:
(1) introducing a vector into a bacterium of the *Agrobacterium* genus; and
(2) culturing the bacterium obtained from step (1) to express the fusion protein;

wherein the vector comprises:
(a) a nucleic acid sequence which encodes the fusion protein of the invention, wherein the fusion protein contains a bacterial secretion signal; and
(b) expression control sequences operably linked to the nucleic acid encoding the-fusion protein, wherein the expression control sequences are suitable for expressing the nucleic acid encoding the fusion protein in *Agrobacterium*.

Another aspect of the invention provides a method for selecting a nucleic acid encoding a polypeptide which has a desired property, the method comprising the display method of the invention, wherein the passenger protein is a plurality of polypeptides which has putatively the desired property. The method further comprises the steps of testing the passenger-displaying microorganism for the desired property in the passenger protein; selecting and isolating the microorganism which displays on its surface the passenger protein with the desired property in the passenger protein; and isolating the expression vector from the organism.

In one embodiment of the method for selecting a nucleic acid encoding a polypeptide which has a desired property, the passenger protein is from an antibody expression library. The desired property may be strong binding to an antigen specific to the antibody, presence of a specific epitope, or catalytic activity.

An other aspect of the invention provides a method for removing a contaminant from a liquid, the method comprising the display method of the invention, wherein the passenger protein is capable of binding to the contaminant, and the method further comprising the steps of contacting the liquid containing the contaminant with the passenger-displaying microorganism for a time and under conditions effective for the passenger protein to bind to the contaminant; and removing the microorganism from the liquid. In one embodiment, the contaminant is a heavy metal and the passenger protein is metallothionein.

Another aspect of the invention provides a method for eliciting an immune response in a mammal, the method comprising the display method of the invention, wherein the passenger protein is capable of eliciting an immune response in the mammal, and the method further comprising the steps of administering the passenger-displaying microorganism for a time and under conditions effective for the mammal to mount an immune response to the passenger protein. In one embodiment, the display microorganism is *A. tumefaciens*, which may be administered as a live vaccine.

Another aspect of the invention provides a method for solid phase enzymatic catalysis of a reaction, the method comprising the display method of the invention, wherein the passenger protein is capable of catalyzing the reaction, and the method further comprising the steps of contacting a substrate of the reaction to be catalyzed with the passenger-displaying microorganism for a time and under conditions effective for enzymatic catalysis of the reaction. In one embodiment, the passenger protein is alkaline phosphatase.

Another aspect of the invention provides a method for purifying a compound, the method comprising the display method of the invention, wherein the passenger protein is capable of binding specifically to the compound, and the method further comprising the steps of contacting a composition containing the compound with the passenger-displaying microorganism for a time and under conditions effective for the passenger protein to bind to the compound; washing the microorganisms for a time and under conditions effective to remove non-specific binding contaminants; and eluting the compound from the microorganisms for a time and under conditions effective to disrupt specific binding between the passenger protein and the compound. In one embodiment, the compound is an antibody and the passenger protein is an antigen specific to the antibody.

BRIEF DESCRIPTION OF THE DRAWINGS

The present invention will be further understood from the following description with reference to the drawings.

A. DNA sequence of the 1.4 kb NheI fragment encompassing aopB and deduced amino acid sequence of AopB. The vertical arrow indicates the mini-Tn5 transposon insertion site. The amino acids predicted to be the putative signal peptide are underlined. A putative Shine-Dalgarno ribosome binding site (AGGAG) was highlighted in bold letters. The horizontal arrows indicate the repeat sequences that may function as a a rho-independent transcription terminator.

B. The genetic and physical maps of different constructs. The numbers above the vertical lines indicate the DNA sequence positions; the numbers in the parentheses indicate the amino acid positions in AopB. The boxed horizontal arrow denotes the aopB open reading frame; the black area of the boxed horizontal arrow denotes the putative signal peptide. The ♦ denotes the insertion site of mini-Tn5. The vertical arrowheads indicate the TnphoA transposon insertion positions of the active phoA-aopB fusions. The horizontal arrows with vertical lines indicate the PCR primers with the introduced restriction sites.

FIG. 2 shows an alignment of the amino acid sequences of the aopB and ropB gene products. Alignment was completed by using the DNASIS program. Shaded letters indicate the amino acids that are identical in both gene products.

Figure 3:
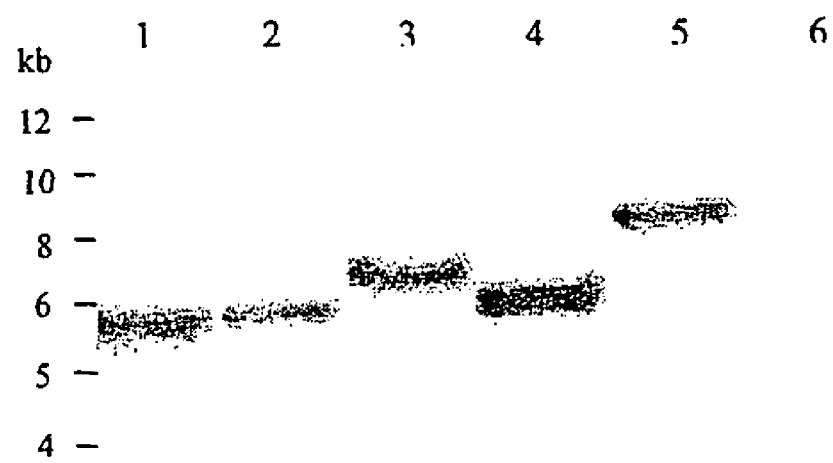

FIG. 3 shows a Southern analysis of the aopB gene region. The total DNA of *Agrobacterium tumefaciens* strains GMI9023 (lane 1), A136 (lane 2), A6 (lane 3), C58 (lane 4) and CGI1 (lane 5) as well as *Rhizobium meliloti* RCR2011 (lane 6) was prepared as described in Example 1. The DNA was digested with SphI and hybridized with the aopB probe labeled with fluorescein.

Figure 4:
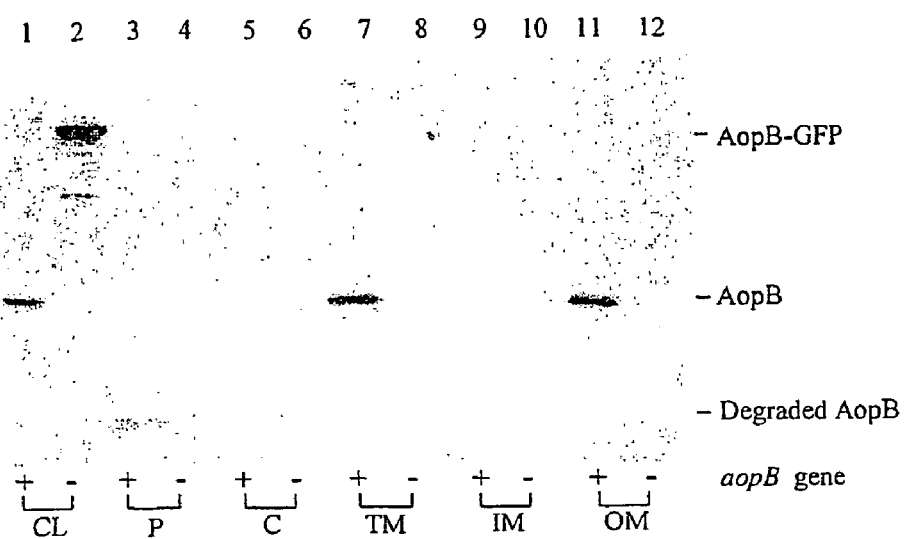

FIG. 4 shows subcellular localization of the AopB protein-in *Agrobacterium tumefaciens*. Induced *A. tumefaciens* cells of C58 (lanes 1, 3, 5, 7, 9, 11) and CGI1 (lanes 2, 4, 6, 8, 10, 12) were collected and fractionated as described in Example 1 into the total cell lysate (CL) (lanes 1 and 2), periplasmic (P) (lanes 3 and 4), cytosolic (C) (lanes 5 and 6), total membrane (TM) (lanes 7 and 8), inner membrane (IM) (lanes 9 and 10) and outer membrane (OM) (lanes 11 and 12) fractions. Samples from the same preparations were electrophoresed on SDS/12% PAGE gels. The proteins were transferred onto Immobilon-P membrane and visualized by AopB antibody.

Figure 5:
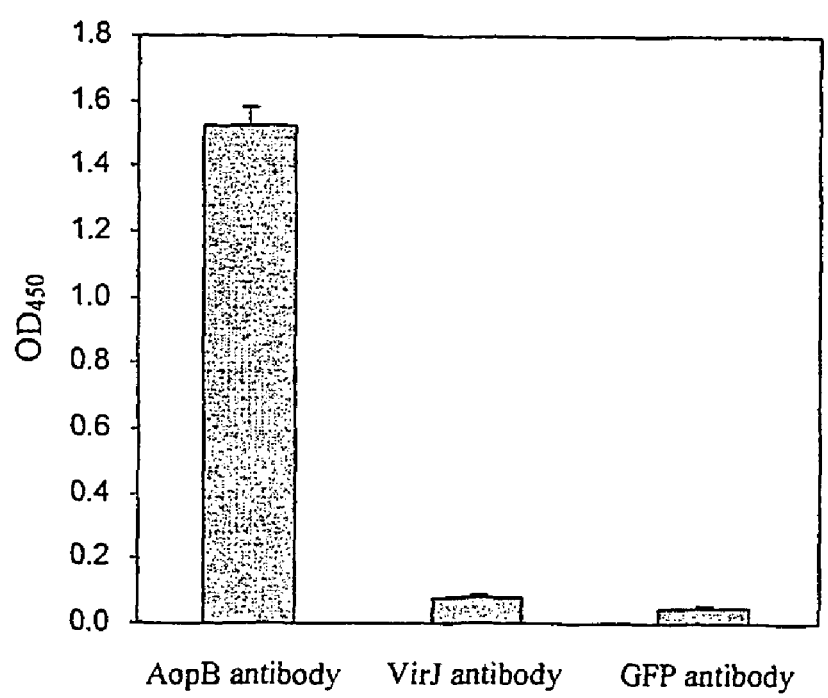

FIG. 5 shows detection of AopB protein on the bacterial cell surface. *Agrobacterium tumefaciens* strain A6010 was grown as described in Example 1. The cells were directly used to interact with different antibodies: rabbit polyclonal AopB antibody, mouse polyclonal VirJ antibody or mouse monoclonal GFP antibody. The whole cell ELISA was conducted as described in Example 1. Error bars indicate standard deviations of triplicate samples.

Figure 6:
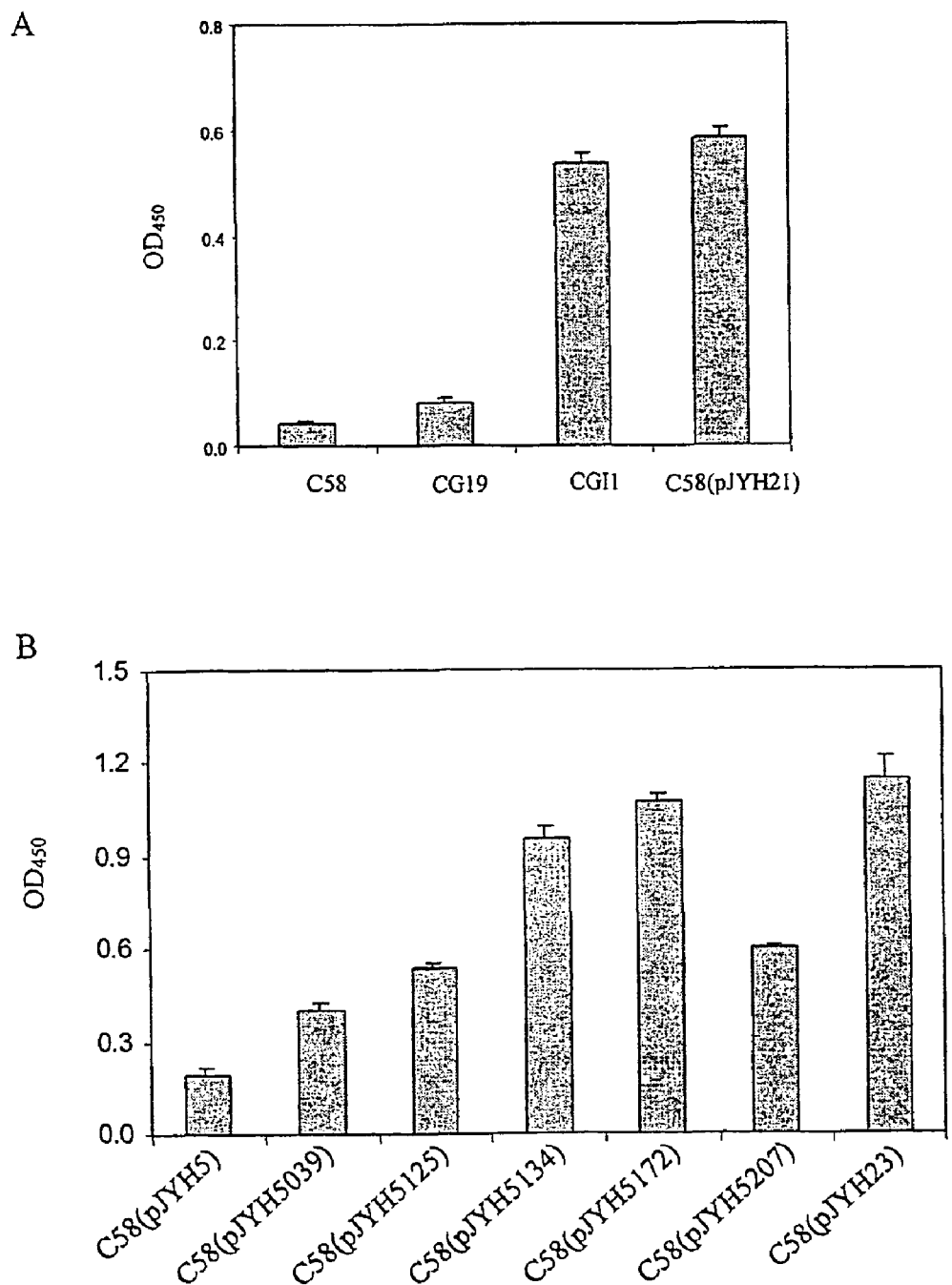

FIG. 6 shows results of whole cell ELISA to detect the display of the AopB-GFP (A) and AopB-PhoA fusion proteins (B) on the cell surface. *Agrobacterium tumefaciens* strains C58 (GFP$^-$), CG19 (producing cytoplasmic GFP), CGI1 (containing aopB-gfp on the chromosome), C58 (pJYH21 (containing aopB-gfp on the plasmid) were grown and fixed, and the AopB-GFP displayed on the cell surface were detected by the whole cell ELISA assays, as described in Example 1 (panel A). The plasmids pJYH5039, pJYH5125, pJYH5134, pJYH5172 and pJYH5207 contained the aopB-phoA fusions with PhoA fused onto AopB at the amino acid positions 39, 125, 134, 172 and 207, respectively; pJYH5 contained the wild-type aopB and pJYH23 contained the phoA coding sequence carried by the display vector. These plasmids were introduced into C58; the C58 cells containing the plasmids were analyzed for the display of AopB-PhoA by the whole cell ELISA assays using the PhoA antibody (panel B). Error bars indicate the standard deviations of triplicated samples.

Figure 7:
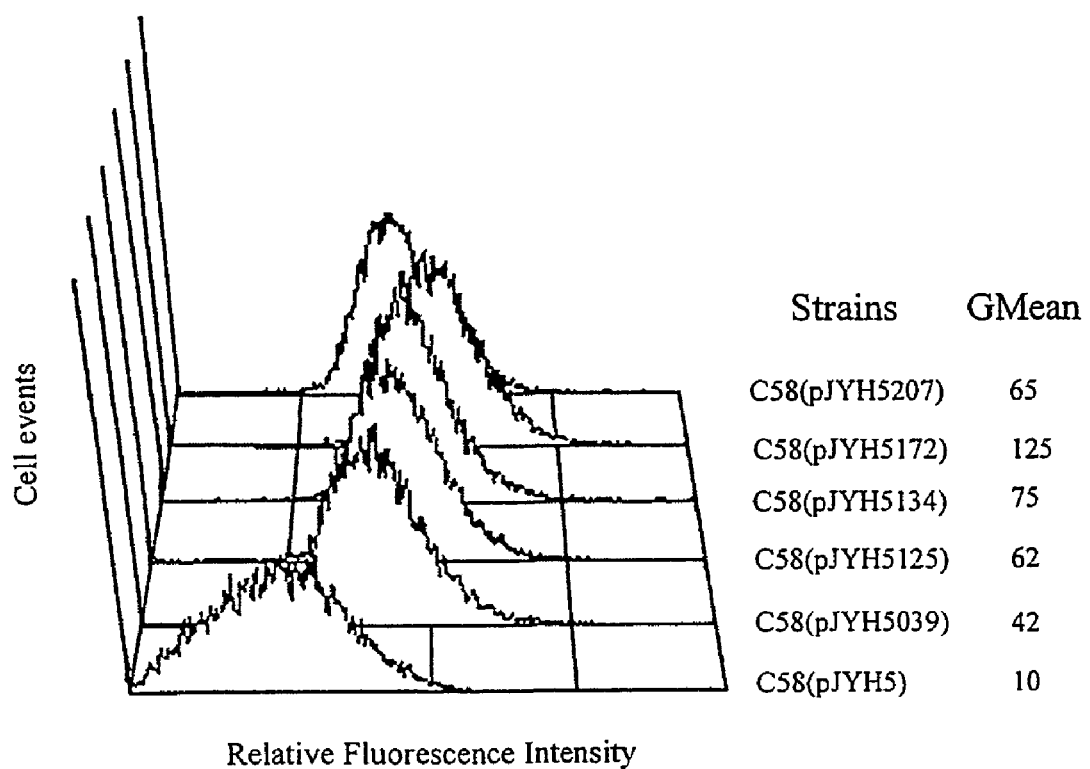

FIG. 7 shows surface display of AopB-PhoA as assessed by flow cytometry analysis. *Agrobacterium tumefaciens* C58 cells containing pJYH5, pJYH5039, pJYH5125, pJYH5134, pJYH5172 and pJYH5207 were grown in IB medium as described in Example 1. Mouse anti-AP antibody was added at 1:1000, and goat anti mouse r-PE conjugate was used at 1:100. Total events of 10, 000 were recorded. GMean stands for geometric mean which is the mean fluorescence intensity of recorded cells.

Figure 8:
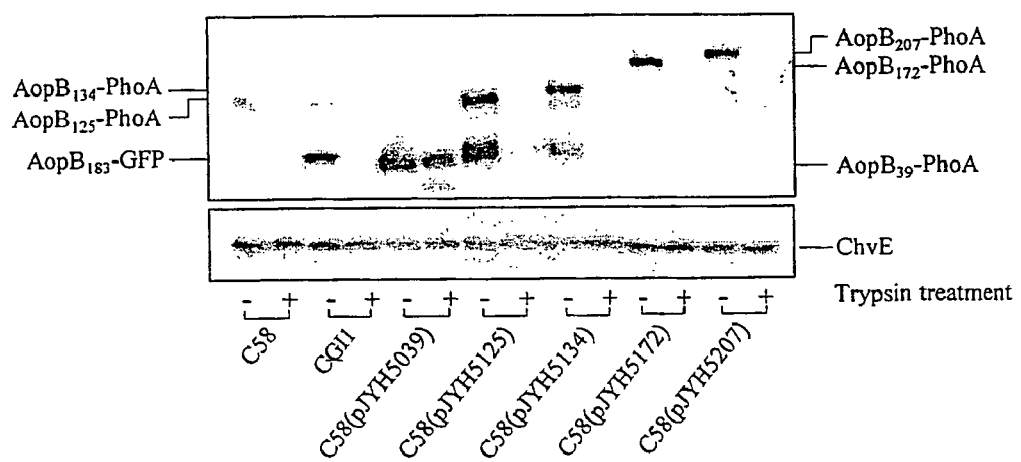

FIG. 8 shows results of protease accessibility assays. *Agrobacterium tumefaciens* strains C58, CGI1, and C58 containing pJYH5039, pJYH5125, pJYH5134, pJYH5172 and pJYH5207 were grown in IB medium. After washing, the cells were treated in the absence or presence of trypsin as described in Example 1. AopB-GFP and AopB-PhoA fusion proteins were visualized by using anti-AopB antibody, and periplasmic protein ChvE was visualized by anti-ChvE antibody.

Figure 9:
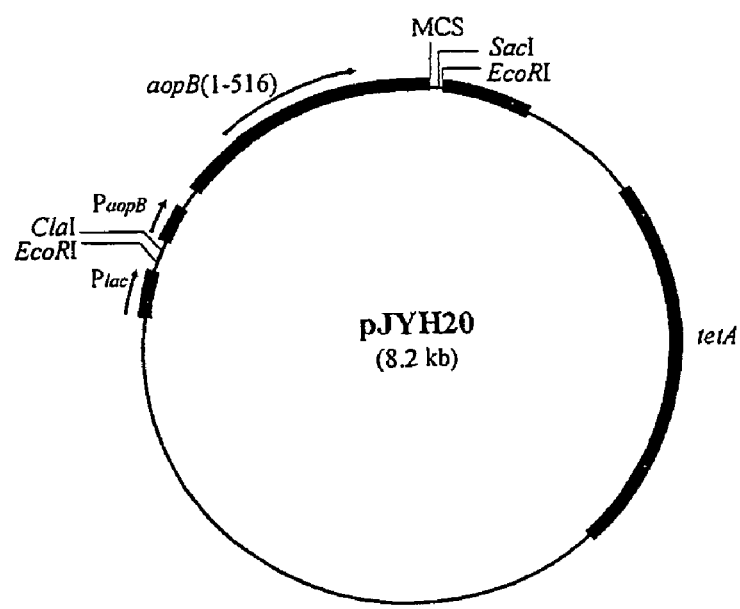

FIG. 9 shows a physical map of display vector pJYH20. This plamid contains the aopB promoter and the 1–516 bp of the aopB, which encodes 1–172 amino acids of AopB. The polylinker was introduced downstream of aopB to facilitate cloning and fusion of foreign genes encoding passenger proteins in frame with the aopB ORF.

Figure 10:
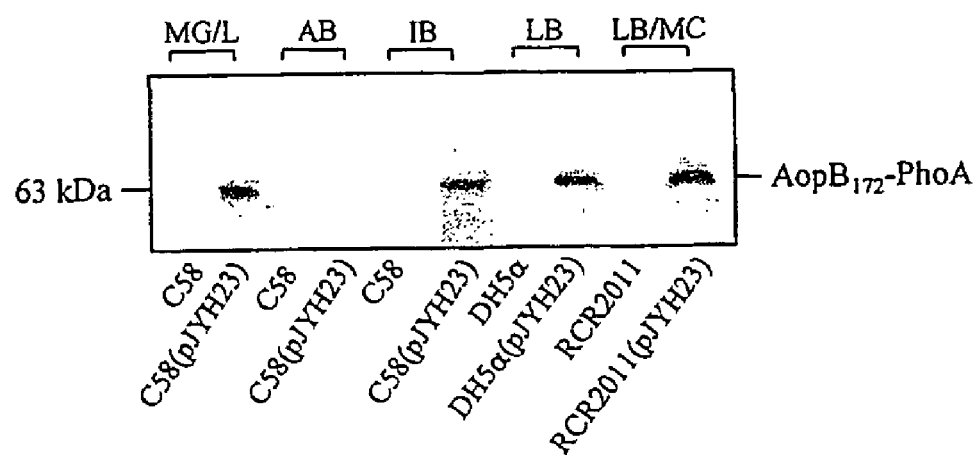

FIG. 10 shows the results of detection of AopB-PhoA expression under different conditions. *Agrobacterium tumefaciens* cells C58 (pJYH23), *E. coli* DH5α(pJYH23) and *R. meliloti* RCR2011 (pJYH23) were grown in the indicated media. The bacterial cells were harvested; and the AopB$_{172}$-PhoA was visualized by anti-AP antibody.

Figure 11:
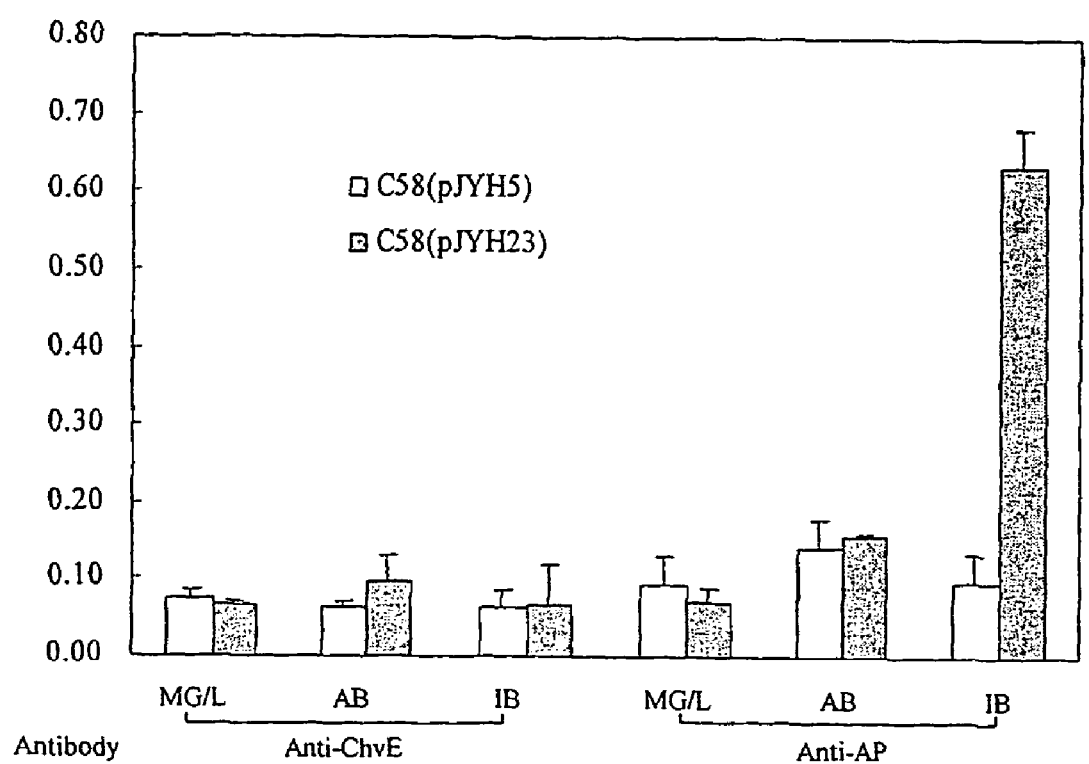

FIG. 11 shows the effects of growth media on surface display. *Agrobacterium tumefaciens* C58 cells containing plasmid pJYH5 or pJYH23 were grown in MG/L at 28° C. overnight and/or transferred to fresh AB or IB at OD$_{600}$=0.3; the cells were cultured for 18 h at 28° C. The display efficiency was determined by the whole cell ELISA. C58 (pJYH5) was used as the negative control. The samples were triplicated during experimentation.

Figure 12:
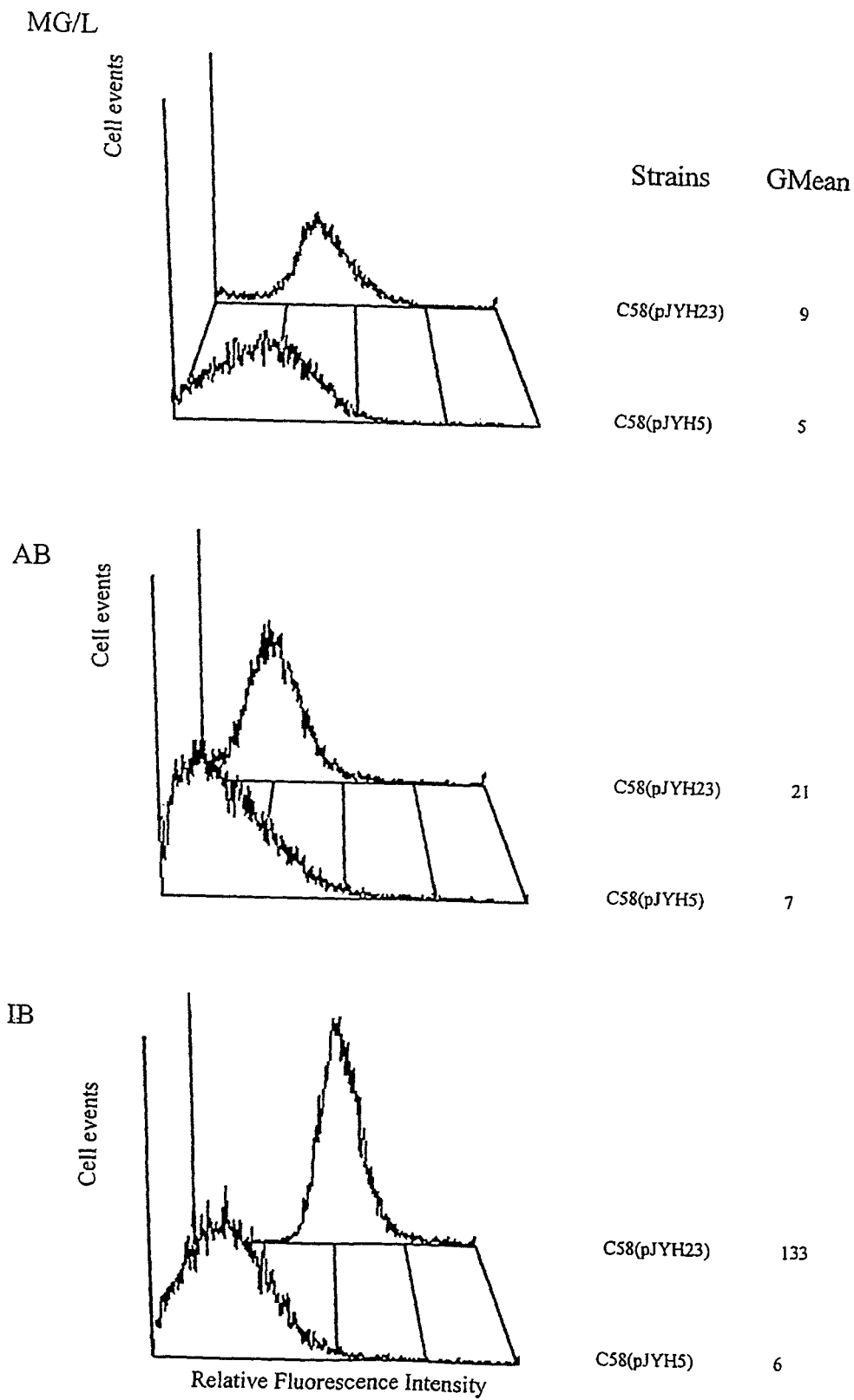

FIG. 12 shows results from flow cytometry analysis of AopB-PhoA display. *Agrobacterium tumefaciens* harboring pJYH5 or pJYH23 were cultured in MG/L, AB or IB medium. Mouse anti-AP antibody was added at 1:1000, and goat anti mouse r-PE conjugate was used at 1:100. Total events of 10, 000 were recorded. GMean stands for geometric mean which is the mean fluorescence intensity of recorded cells.

DETAILED DESCRIPTION OF THE PREFERRED EMBODIMENTS

A. The aopB Gene and aopB Protein

An *Agrobacterium tumefaciens* chromosomal gene designated aopB has been identified and characterized. This gene shares high homology with ropB, a *Rhizobium leguminosarum* gene encoding an outer membrane protein. Mutation at aopB by a transposon did not affect the bacterial growth on different growth media.

The mutant CGI1 cells (containing the aopB-gfp fusion) cultured on a minimal medium of pH 5.5 gave strong fluorescence under UV light but not on a minimal medium of neutral pH, indicating that the aopB gene is inducible by an acidic pH. aopB encodes a putative protein of 218 amino acids with a predicted molecular weight of 22.8 kDa. TnphoA transposon mutagenesis of aopB, subcellular fractionation and whole cell ELISA experiments indicated that AopB is an outer membrane protein exposed on the bacterial cell surface and that AopB was present exclusively in the outer membrane and not in other fractions.

A description of the exemplified sequences is provided below:
SEQ ID No: 1 Nucleotide sequence containing aopB gene
SEQ ID No: 2 Amino acid sequence of full-length AopB
SEQ ID No: 3 aopB nucleotide sequence encoding AopB without putative signal sequence
SEQ ID No: 4 Amino acid sequence of AopB without putative signal sequence
SEQ ID No: 5 primer p54
SEQ ID No: 6 primer p55
SEQ ID No: 7 primer p119
SEQ ID No: 8 primer p112
SEQ ID No: 9 primer p118
SEQ ID No: 10 GFPuvFh3
SEQ ID No: 11 GFPuvRp1
SEQ ID No: 12 PhoAfH3
SEQ ID No: 13 PhoAreP1

AopB has been identified as a member of a group of membrane proteins of Gram-negative bacteria (hereafter referred to as "AopB-related membrane proteins") which include: RopB (60% amino acid sequence similarity), the immunogenic outer membrane proteins of *Brucella* species (42–47% amino acid sequence similarity), Pap31 of *Bartonella hensela* infected with a bacteriophage (46% amino acid sequence similarity), *Pasteurella* (*Mannheimia*) *haemolytica* outer membrane protein PomA (47% amino acid sequence similarity), PPE of *Mycobacterium tuberculosis* (39% amino acid sequence similarity), *Haemophilus ducreyi* major outer membrane protein (43% amino acid sequence similarity), and the outer membrane porin of *Vibrio cholerae* (40% amino acid sequence similarity), as well as the C-terminal half of the porin protein F (OprF) of *Pseudomonas* species.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

The term "isolated polynucleotide" is defined as a polynucleotide removed from the environment in which it naturally occurs. "Isolated polynucleotide" is a polynucleotide the structure of which is not identical to that of any naturally occurring polynucleotide. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a polynucleotide incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of-a hybrid gene, i.e. a gene encoding a fusion protein. Specifically excluded from this definition are polynucleotides present in mixtures of (i) DNA molecules, (ii) transfected cells, and (iii) cell clones, e.g. as these occur in a DNA library such as a cDNA or genomic DNA library.

For example, a DNA molecule present naturally in the genome of a bacterium or as part of a gene bank is not isolated, but the same molecule separated from the remaining part of the bacterial genome, as a result of, e.g., a cloning event (amplification), is isolated. Typically, an isolated DNA molecule is free from DNA regions (e.g., coding regions) with which it is immediately contiguous at the 5' or 3' end, in the naturally occurring genome. Such isolated polynucleotides may be part of a vector-or a composition or a non-native genome and still be defined as isolated in that such a vector or composition is not part of the natural environment of such polynucleotide.

The polynucleotide of the invention is either RNA or DNA (cDNA, genomic DNA, or synthetic DNA), or modifications, variants, homologs or fragments thereof. The DNA is either double-stranded or single-stranded, and, if single-stranded, is either the coding strand or the non-coding (anti-sense) strand. Any one of the sequences that encode the polypeptides of the invention as shown in SEQ ID NO: 1 or 3 is (a) a coding sequence, (b) a ribonucleotide sequence derived from transcription of (a), or (c) a coding sequence which uses the redundancy or degeneracy of the genetic code to encode the same polypeptides.

By "polypeptide" or "protein" is meant any chain of amino acids, regardless of length or post-translational modification (e.g., glycosylation or phosphorylation). Both terms are used interchangeably in the present application.

Amino acid sequences are provided which are homologous to SEQ ID NO: 2 or 4. As used herein, "homologous amino acid sequence" is any polypeptide which is encoded, in whole or in part, by a nucleic acid sequence which hybridizes at 25–35° C. below critical melting temperature (Tm), to any portion of the nucleic acid sequence of any one of SEQ ID NO: 1 or 3. A homologous amino acid sequence is one that differs from an amino acid sequence shown in SEQ ID NO: 2 or 4 by one or more amino acid substitutions, preferably conservative substitutions. Such a sequence also encompass serotypic variants (defined below) as well as sequences containing deletions or insertions which retain inherent characteristics of the polypeptide such as immunogenicity. Preferably, such a sequence is at least 61% (for example, 65%, 68%, 70%, 73%, 75%, 78%), and preferably at least 80% (for example, 82%, 85%, 88%, 90%, 93%, 95%, 98%) identical to SEQ ID NO: 2 or 4.

Homologous amino acid sequences include sequences that are identical or substantially identical to SEQ ID NO: 2 or 4. By "amino acid sequence substantially identical" is meant a sequence that is at least 90% (for example 92%, 94%, 95%, 96%, 97%, 98%), and preferably 99% identical to an amino acid sequence of reference. In one preferred embodiment, the homologous sequence differs from the sequence of reference by a majority of conservative amino acid substitutions.

Conservative amino acid substitutions are substitutions among amino acids of the same class. These classes include, for example, amino acids having uncharged polar side chains, such as asparagine, glutamine, serine, threonine, and tyrosine; amino acids having basic side chains, such as lysine, arginine, and histidine; amino acids having acidic side chains, such as aspartic acid and glutamic acid; and amino acids having nonpolar side chains, such as glycine, alanine, valine, leucine, isoleucine, proline, phenylalanine, methionine, tryptophan, and cysteine.

Homologous polynucleotide sequences are defined in a similar way. Preferably, a homologous sequence is one that is at least 45%, (for example 50%, 55%, 60%, 65%, 70%, 75%, 80%, 85%, 87%, 90%, 93%, 96%) and preferably 99% identical to the coding sequence of SEQ ID No: 1 or 3.

Homology is measured-using sequence analysis software such as Sequence Analysis Software Package of the Genetics Computer Group, University of Wisconsin Biotechnology Center, 1710 University Avenue, Madison, Wis. 53705. Amino acid sequences are aligned to maximize identity. Gaps may be artificially introduced into the sequence to attain proper alignment. Once the optimal alignment has been set up, the degree of homology is established by recording all of the positions in which the amino acids of both sequences are identical, relative to the total number of positions.

As used herein, "percent homology", "percent identity" or "percent similarity" of two amino acid sequences or of two nucleic acids is determined by aligning the subject sequences so that the highest order homology (match) is obtained. "Identity" or "similarity" per se has an art-recognized meaning and can be calculated using published techniques. The computer program used in this application to determine identity or similarity between two sequences is the DNAStar software (DNAStar Inc., Madison, Wis.). However, other software such as the GCG program package (Devereux, J., et al., Nucleic Acids Research (1984) 12(1): 387) and BLASTP, BLASTN, FASTA (Atschul, S. F. et al., J Molec Biol (1990) 215:403) may be used. Homology (identity or similarity) as defined herein is determined conventionally using the well known computer program, BESTFIT (Wisconsin Sequence Analysis Package, Version 8 for Unix, Genetics Computer Group. University Research Park, 575 Science Drive, Madison, Wis. 53711). When using BESTFIT or any other sequence alignment program to determine whether a particular sequence is, for example, about 90% homologous to a reference sequence, according to the present invention, the parameters are set such that the percentage of identity is calculated over the full length of the reference nucleotide sequence or amino acid sequence and that gaps in homology of up to about 10% of the total number of nucleotides in the reference sequence are allowed.

Percentage similarity between two polypeptides may also be scored by comparing the amino acid sequences of the two polypeptides by using programs well known in the art, including the BESTFIT program, by employing default settings for determining similarity.

The algorithm of Karlin and Altschul (Proc. Natl. Acad. Sci. USA 87:2264–2268, 1990), modified as in Karlin and Altschul (Proc. Natl. Acad. Sci. USA 90:5873–5877, 1993), as incorporated into the NBLAST and XBLAST programs of Altschul et al. (J. Mol. Biol. 215:403–410, 1990), are used for searches to obtain sequences homologous to a reference sequence.

BLAST nucleotide searches are performed with the NBLAST program, score=100, wordlength=12, to obtain nucleotide sequences homologous to a nucleic acid of the invention. BLAST protein searches are performed with the XBLAST program, score=50, wordlength=3, to obtain amino acid sequences homologous to a reference polypeptide (e.g. SEQ ID NO: 2 or 4). To obtain gapped alignments for comparison purposes, Gapped BLAST is utilized as described in Altschul et al. (Nucleic Acids Res. 25:389–3402, 1997). When utilizing BLAST and Gapped BLAST programs, the default parameters of the respective programs (e.g. XBLAST and NBLAST) are used. See Altschul, Stephen F., et al. (1997), "Gapped BLAST and PSI-BLAST; a new generation of protein database search programs", Nucleic Acids Res. 25:3389–3402.

Polypeptides having a sequence homologous to SEQ ID NO: 2 or 4 include naturally-occurring allelic variants, as well as mutants or any other non-naturally occurring variants that retain the inherent characteristics of the reference polypeptide. Such an inherent characteristic for AopB include its topology as a surface-exposed outer membrane protein in gram-negative bacteria.

As is known in the art, an allelic variant is an alternate form of a polypeptide that is characterized as having a substitution, deletion, or addition of one or more amino acids that does not alter the biological function of the polypeptide. By "biological function" is meant the function of the polypeptide in the cells in which it naturally occurs, even if the function is not necessary for the growth or survival of the cells. For example, the biological function of a porin is to allow the entry into cells of compounds present in the extracellular medium.

Allelic variants are very common in nature. For example, a bacterial species such as *M. catarrhalis*, is usually represented by a variety of strains that differ from each other by minor allelic variations. Indeed, a polypeptide that fulfills the same biological function in different strains can have an amino acid sequence (and polynucleotide sequence) that is not identical in each of the strains. Such an allelic variation may be equally reflected at the polynucleotide level.

One method of obtaining polynucleotides encoding homologous polypeptides or allelic variants is by polymerase chain reaction (PCR) amplification of genomic bacterial DNA extracted by conventional methods. This involves the use of synthetic oligonucleotide primers matching upstream and downstream of the 5' and 3' ends of the coding sequence. Suitable primers are designed according to the nucleotide sequence information provided in SEQ ID NO: 1 or 3. The procedure is as follows: a primer is selected which consists of 10 to 40 (e.g. 13, 16, 19, 22, 24 and so forth), preferably 15 to 25 nucleotides. It is advantageous to select primers containing C and G nucleotides in a proportion sufficient to ensure efficient hybridization; i.e., an amount of C and G nucleotides of at least 40%, preferably 50% of the total nucleotide content. A standard PCR reaction contains typically 0.5 to 5 Units of Taq DNA polymerase per 100 μL, 20 to 200 μM deoxynucleotide each, preferably at equivalent concentrations, 0.5 to 2.5 mM magnesium over the total deoxynucleotide concentration, $10^5$ to $10^6$ target molecules, and about 20 pmol of each primer. About 25 to 50 PCR cycles are performed, with an annealing temperature 15° C. to 5° C. below the true Tm of the primers. A more stringent annealing temperature improves discrimination against incorrectly annealed primers and reduces incorporation of incorrect nucleotides at the 3' end of primers. A denaturation temperature of 95° C. to 97° C. is typical, although higher temperatures may be appropriate for dematuration of G+C-rich targets. The number of cycles performed depends on the starting concentration of target molecules, though typically more than 40 cycles is not recommended as non-specific background products tend to accumulate.

An alternative method for retrieving polynucleotides encoding homologous polypeptides or allelic variants is by hybridization screening of a DNA or RNA library. Hybridization procedures are well-known in the art and are described for example in Sambrook et al. (Sambrook, J. E. F. et. al. (1989) Molecular Cloning a Laboratory Manual $2^{nd}$ ed. Cold Spring Harbor Laboratory Press, Cold Spring Harbor N.Y.). Important parameters for optimizing hybridization conditions are reflected in a formula used to obtain the critical melting temperature above which two complementary DNA strands separate from each other. For polynucleotides of about 600 nucleotides or larger, this formula is as follows: Tm=81.5+0.41×(% G+C)+16.6 log(cation ion concentration)−0.63×(% formamide)−600/base number. Under appropriate stringency conditions, hybridization temperature (Th) is approximately 20 to 40° C., 20 to 25° C., or, preferably 30 to 40° C. below the calculated Tm. Those skilled in the art will understand that optimal temperature and salt conditions can be readily determined.

Hybridizing nucleic acids of the type described herein-can be used, for example, as a cloning probe, a primer or a diagnostic probe. Hybridization is typically performed under stringent conditions. Nucleic acid duplex or hybrid stability is expressed as the melting temperature or Tm, which is the temperature at which the hybridizing strands dissociate. This melting temperature is used to define the required stringency conditions. If sequences are to be identified that are related and substantially identical, rather than identical, to the probe sequence, then it is useful to first establish the lowest temperature at which only homologous hybridization occurs with a particular concentration of salt (e.g. SSC OR SSPE). Then, assuming that a 1% mismatching results in a 1° C. decrease in the Tm, the temperature of the final wash in the hybridization reaction is reduced accordingly (for example, if sequences having more than 95% identity with the probe are sought, the final wash temperature is decreased by 5%). In practice, the change in Tm can be between 0.5° C. and 1.5° C. per 1% mismatch. Stringent conditions are achieved for both pre-hybridizing and hybridizing incubations (i) within 4–16 hours at 42° C., in 6×SSC containing 50% formamide, or (ii) within 4–16 hours at 65° C. in an aqueous 6×SSC solution (1 M NaCl, 0.1 M sodium citrate (pH 7.0)). Typically, hybridization experiments are performed at a temperature from 60 to 68° C., e.g. 65° C. At such a temperature, stringent hybridization conditions can be achieved in 6×SSC, preferably in 2×SSC or 1×SSC, more preferably in 0.5×SSc, 0.3×SSC or 0.1×SSC (in the absence of formamide). 1×SSC contains 0.15 M NaCl and 0.015 M sodium citrate.

Useful homologs and fragments thereof that do not occur naturally are designed using known methods for identifying regions of an antigen that are likely to tolerate amino acid sequence changes and/or deletions. As an example, homologous polypeptides from different species are compared; conserved sequences are identified. The more divergent sequences are the most likely to tolerate sequence changes. Homology among sequences may be analyzed as described above using, as an example, the BLAST homology searching algorithm of Altschul et al., Nucleic Acids Res.; 25:3389–3402 (1997). Alternatively, sequences may be modified in vitro, then screened for their ability to display a passenger protein according to the method outlined below.

A person skilled in the art will readily understand that by following the screening process of this invention, it will be determined without undue experimentation whether a particular homolog or fragment of SEQ ID NO: 2 or 4 retains the outer membrane topology of AopB and is useful as a carrier protein for displaying a passenger protein. A typical assay comprises the steps:

(i) joining a reporter (passenger) protein such as GFP in-frame with the test homolog or fragment. Conveniently, nucleic acid molecules encoding the passenger protein and the test homolog or fragment are joined in-frame to create a fusion protein. The nucleic acid encoding the fusion protein is then inserted into an expression vector for expressing the fusion protein in the bacterium in step (ii);

(ii) transforming a Gram-negative bacterium, preferably *Agrobacterium tumefaciens*, with the nucleic acid encoding the fusion protein; and (iii) assaying the transformed bacteria for reporter protein activity using an assay suitable for whole cells, such as FACS. Reporter protein activity at the cell surface would indicate that the homolog or fragment is an outer membrane protein and may be useful as a carrier protein for display.

Polypeptide derivatives are provided that are partial sequences of SEQ ID NO: 2 or 4, partial sequences of polypeptide sequences homologous to SEQ ID NO: 2 or 4, polypeptides derived from full-length polypeptides by internal deletion, and fusion proteins.

In a preferred embodiment, fragments of AopB are from the N-terminal region of SEQ ID No:2. In other embodiments, fragments of AopB which are at least 39 consecutive amino acids from the N-terminal region of SEQ ID No:2 are preferred, e.g. 125, 134, 172, 183 and 207 consecutive amino acids from the N-terminal region of SEQ ID No:2. Fusions of passenger proteins to 125, 134, 172, 183 and 207 amino acid fragments of SEQ ID No:2 have been exemplified and shown to be effective for cell surface display.

Especially preferred are fragments of 134 to 183 consecutive amino acids from the N-terminal region of SEQ ID No:2, e.g. fragments of 140, 150, 155, 160, 165, 166, 168, 170, 172, 174, 176, 178, 180 amino acids.

Fusions between carrier and passenger protein may be such that the carrier fragment is directly contiguous with the passenger amino acid sequence. Alternatively, the carrier fragment may be joined to the passenger by way of a linker sequence such as the flexible linker from an immunoglobulin (see U.S. Pat. No. 5,516,637). The linker may also contain a protease-specific cleavage site so that the passenger protein may be controllably released from the carrier protein. Examples of protease sites include those specific to cleavage by: factor Xa, enterokinase, collagenase, Igase (from *Neisseria gonorrhoeae*), thrombin, and TEV (Tobacco Etch Virus) protease.

Polynucleotides of 30 to 600 nucleotides of SEQ ID NO: 1 or 3 or their corresponding complements, homologs or variants, are useful at least as probes for retrieving other homologs or variants. One method for retrieving the partial sequences is by PCR amplification. The parameters outlined above are applied and primers are used which match the sequences upstream and downstream of the 5' and 3' ends of the fragment to be amplified. The template polynucleotide for such amplification is either the full length polynucleotide of SEQ ID NO: 1 or 3 or their corresponding homologs or variants, or a polynucleotide contained in a mixture of polynucleotides such as a DNA or RNA library. As an alternative method for retrieving the partial sequences, screening hybridization is carried out under conditions described above and using the formula for calculating Tm. Where fragments of 30 to 600 nucleotides are to be retrieved, the calculated Tm is corrected by subtracting (600/polynucleotide size in base pairs) and the stringency conditions are defined by a hybridization temperature that is 5 to 10° C. below Tm. Where oligonucleotides shorter than 20–30 bases are to be obtained, the formula for calculating the Tm is as follows: $Tm=4\times(G+C)+2(A+T)$. For example, an 18 nucleotide fragment of 50% G+C would have an approximate Tm of 54° C.

Short peptides that are fragments of SEQ ID NOs: 2 or 4 or their corresponding homologous sequences, may be obtained directly by chemical synthesis (E. Gross and H. J. Meinhofer, 4 The Peptides: Analysis, Synthesis, Biology; Modern Techniques of Peptide Synthesis, John Wiley & Sons (1981), and M. Bodanzki, Principles of Peptide Synthesis, Springer-Verlag (1984)).

Polynucleotides encoding polypeptide fragments and polypeptides having large internal deletions are constructed using standard methods (Sambrook, J. E. F. et. al. (1989) Molecular Cloning a Laboratory Manual $2^{nd}$ ed. Cold Spring Harbor Laboratory Press, Cold Spring Harbor N.Y.). Such methods include standard PCR, inverse PCR, and restriction enzyme treatment of cloned DNA molecules. Components for these methods and instructions for their use are readily available from various commercial sources such as Stratagene.

Certain amino acids may be substituted for other amino acids in a protein structure without appreciable loss of interactive binding capacity with structures such as, for example, binding sites. Since it is the interactive capacity and nature of a protein that defines that protein's biological functional activity, certain amino acid sequence substitutions can be made in a protein sequence to obtain a protein with like properties. It is contemplated that changes may be made in the polypeptide sequences of AopB, or corresponding DNA sequences which encode AopB without appreciable loss of biological utility or activity.

In making such changes, the hydropathic index of amino acids may be considered. The importance of the hydropathic amino acid index in conferring interactive biologic function on a protein is generally understood in the art (Kyte, J., and Doolittle, R. F. (1982) Simple method for displaying the hydropathy character of a protein. J Mol Biol 157: 105–132). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Membrane topology may be predicted based on the algorithms described by Sipos and von Heijne (Sipos et al.,1993, Eur. J. Biochem 213:1333–1340).

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within .+−.2 is preferred, those which are within .+−.1 are particularly preferred, and those within .+−.0.5 are even more particularly preferred.

It is also understood in the art that the substitution of like amino acids can be made effectively on the basis of hydrophilicity. U.S. Pat. No. 4,554,101, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0 .+−.1); glutamate (+3.0 .+−.1); serine (+0.3); asparagine (+0.2); glutamine (+0.2); glycine (0); threonine (−0.4); proline (−0.5 .+−.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within .+−.2 is preferred, those which are within .+−.1 are particularly preferred, and those within .+−.0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

As used herein, a fusion polypeptide is one that contains a polypeptide or a polypeptide derivative of the invention fused at the N- or C-terminal end to any other polypeptide (hereinafter referred to as a passenger protein or polypeptide). A simple way to obtain such a fusion polypeptide is by translation of an in-frame fusion of the polynucleotide sequences, i.e., a hybrid gene. The hybrid gene encoding the fusion polypeptide is inserted into an expression vector which is used to transform or transfect a host cell. Alternatively, the polynucleotide sequence encoding the polypeptide or polypeptide derivative is inserted into an expression vector in which the polynucleotide encoding the passenger polypeptide is already present. Large proteins, e.g. β-lactamase, alkaline phosphatase, cellulose binding domain of cellulase, or single-chain $F_v$ antibody, are expected to be effectively surface expressed.

An advantageous example of a fusion polypeptide is one where the polypeptide or homolog or fragment of the invention (the 'carrier protein') is fused to a polypeptide having enzymatic activity, such as alkaline phosphatase or a enzyme capable of secondary modification (e.g. glycosylase or disulfide isomerase). Another advantageous fusion is one where the carrier protein is fused to a passenger polypeptide which can bind to a compound such as a contaminant (e.g. heavy metals in solution, or viral contaminants in blood) or another protein (e.g. an antibody). If the passenger protein is itself an antibody, the fusion may be used to purify the antigen specific to the antibody, or used to remove the specific antigen from solution. If the passenger protein is an antigenic protein, the fusion protein may be used as a vaccine to elicit an immune response against the antigen.

To effect fusion, the passenger polypeptide is fused to the N-, or preferably, to the C-terminal end of the polypeptide of the invention. Preferred sites of insertion are amino acid positions 39, 125, 134, 172, 183 and 207 of SEQ ID No:2. Insertion within 10 amino acids upstream or downstream of amino acid position 172 is most preferred.

The polynucleotides of the invention also encode hybrid precursor polypeptides containing heterologous signal peptides, which mature into polypeptides of the invention. By "heterologous signal peptide" is meant a signal peptide that is not found in naturally-occurring precursors of polypeptides of the invention. Preferred heterologous signal peptides are those of, or derived from, Gram-negative bacteria. In preferred embodiments, the heterologous signal peptides are joined to the N-terminus of the mature sequence of the carrier protein.

Gram-negative bacteria possess unique as well as complex cell envelope structure which consists of inner cellular membrane, periplasm, and outer cellular membrane. For expression of passenger proteins on the surface using the carrier proteins of the invention, the expressed fusion protein has to be able to be transported through the inner cellular membrane and outer membrane to the surface and be maintained on the surface of the bacteria.

In order for the fusion protein to be located to the surface of the cell, the carrier protein should have efficient secretion signal sequences for facilitating the penetration of the carrier protein through the inner membrane of the cell and a targeting signal for anchoring the fusion protein to the surface of the cell. Signal and targeting sequences may found in naturally-occurring precursors of the carrier protein, or they may be heterologous sequences, i.e. derived either from the same bacterial protein or from different proteins of the same or different bacterial species.

In gram-negative bacteria the outer membrane acts as a barrier to restrict the export of proteins from the cell. Normally only pilins, flagellins, specific enzymes and a few toxins are completely transported across the outer membrane. Most of these proteins are first secreted into the periplasmic space via the general secretion pathway and then cross the outer membrane by a process that involves the action of several additional gene products.

For some outer membrane proteins, such as the PhoE porin, the information necessary for proper localization and assembly is interspersed within the primary sequence. Alternatively, the targeting signal may be contained within a single short continuous segment. For example, the first nine N-terminal amino acids of the major *E. coli* lipoprotein are necessary for proper localization in the outer membrane. Fusion to this short sequence is sufficient to direct the normally soluble periplasmic protein β-lactamase to the outer membrane. Similarly, studies with OmpA have suggested that the region between residues 154 and 180 is crucial for localization. With OmpA, targeting and outer membrane assembly appear to be distinct events.

In one embodiment, a hybrid precursor polypeptide comprises SEQ ID No:4 and, joined to its N-terminus, an amino acid sequence responsible for secretion to the outer membrane. Membrane targeting sequences have been identified in several of membrane proteins including Lpp. Generally, as in the case of Lpp, the protein domains serving as localization signals are relatively short. The Lpp targeting sequence includes the signal sequence and the first 9 amino acids of the mature protein. These amino acids are found at the N-terminus of Lpp. Examples of other proteins that may serve as sources of secretion and membrane localization signals include *E. coli* outer membrane lipoproteins such as TraT, OsmB, NlpB, BlaZ; *Pseudomonas aeruginosa* lipoprotein 1; *Haemophilus influenza* PA1 and PCN proteins; *Rickettsia rickettsii* 17 kDa lipoprotein; *Neisseria gonorrhea* H.8 protein and the like.

One aspect of the invention encompasses (i) an expression cassette containing a polynucleotide of the invention placed under the control of the elements required for expression, in particular under the control of an appropriate promoter; (ii) an expression vector containing an expression cassette of the invention; (iii) a procaryotic or eucaryotic cell transformed or transfected with an expression cassette and/or vector of the invention; as well as (iv) a process for producing a polypeptide or polypeptide derivative encoded by a polynucleotide of the invention, which involves culturing a procaryotic or eucaryotic cell transformed or transfected with an expression cassette and/or vector of the invention, under conditions that allow expression of the DNA molecule of the invention and, recovering the encoded polypeptide or polypeptide derivative from the culture.

*R. leguminosarum* cells can be transformed as described in Garg B, Dogra R C, Sharma P K. 1999. High-efficiency transformation of *Rhizobium leguminosarum* by electroporation. Applied and Environmental Microbiology 65: 2802–2804; and Giddings G. Mytton L, Taylor L, Thomas S, Allen D, Skot L. 2000. A secondary effect of transformation in *Rhizobium leguminosarum* transgenic for *Bacillus thuringiensis* Subspecies tenebrionis delta-endotoxin (cryIIIA) genes. Theoretical and Applied Genetics 100: 820–823.

*Sinorhizobium. meliloti* cells can be transformed as described in Hayashi M, Maeda Y, Hashimoto Y, Murooka Y. 2000. Efficient transformation of *Mesorhizobium huakuii* subsp rengei and *Rhizobium* species. Journal of Bioscience and Bioengineering 89: 550–553.

*Mesorhizobium loti* cells can be transformed as described in Hayashi M, Maeda Y. Hashimoto Y, Murooka Y. 2000. Journal of Bioscience and Bioengineering 89: 550–553.

*Bradyrhizobium japonicum* cells can be transformed as described in Hattermann D R, Stacey G. 1990. Efficient DNA transformation of *Bradyrhizobium japonicum* by electroporation. Applied and Environmental Microbiology 56: 833–836; and Hayashi M, Maeda Y, Hashimoto Y, Murooka Y. 2000. Journal of Bioscience and Bioengineering 89: 550–553.

*B. melitensis* cells can be transformed as described in Ekaza E, Guilloteau L, Teyssier J, Liautard J P, Kohler S. 2000. Functional analysis of the ClpATPase ClpA of *Brucella suis*, and persistence of a knockout mutant in BALB/c mice. Microbiology 146: 1605–1616; and Jubier-Maurin V, Boigegrain R A, Cloeckaert A, Gross A, Alvarez-Martinez M T, Terraza A, Liautard J, Kohler S, Rouot B, Dornand J, Liautard J P. 2001. Major outer membrane protein Omp25 of *Brucella suis* is involved in inhibition of tumor necrosis factor alpha production during infection of human macrophages. Infection and Immunity 69: 4823–4830.

*B. henselae* cells can be transformed as described in Dehio M, Knorre A, Lanz C, Dehio C. 1998. Construction of versatile high-level expression vectors for *Bartonella henselae* and the use of green fluorescent protein as a new expression marker. Gene 215: 223–229.

*Bartonella quintana* cells can be transformed as described in Dehio M, Knorre A, Lanz C, Dehio C. 1998. Construction of versatile high-level expression vectors for *Bartonella henselae* and the use of green fluorescent protein as a new expression marker. Gene 215: 223–229.

*Mannheimia haemolytica* cells can be transformed as described in Marciel A M, Highlander S K. 2001. Use of operon fusions in *Mannheimia haemolytica* to identify environmental and cis-acting regulators of leukotoxin transcription. Infection and Immunity 69: 6231–6239.

*Mycobacterium tuberculosis* cells can be transformed as described in Hinds J, Mahenthiralingam E, Kempsell K E, Duncan K, Stokes R W, Parish T, Stoker N G. 1999. Enhanced gene replacement in mycobacteria. Microbiology 145: 519–527; and Bachrach G, Colston M J, Bercovier H, Bar-Nir D, Anderson C, Papavinasasundaram K G. 2000. A new single-copy mycobacterial plasmid, pMF1, from *Mycobacterium fortuitum* which is compatible with the pAL5000 replicon. Microbiology 146: 297–303.

*Pseudomonas aeruginosa, Pseudomonas agarici* and *Pseudomonas fuscovaginae* cells can be transformed as described in Enderle P J, Farwell M A. 1998. Electroporation of freshly plated *Escherichia coli* and *Pseudomonas aeruginosa* cells. Biotechniques 25: 954; and Kim C, Wood T K.1998. Electroporation of pink-pigmented methylotrophic bacteria. Applied Biochemistry and Biotechnology 73: 81–88.

*Streptomyces coelicolor* cells can be transformed as described in Oh S H, Chater K F. 1997. Denaturation of circular or linear DNA facilitates targeted integrative transformation of *Streptomyces coelicolor* A3(2): Possible relevance to other organisms. Journal of Bacteriology 179: 122–127; and Gregorovic G, Vujaklija D. 2001. High efficiency of direct plasmid transfer between two *Streptomyces* spp., and between *Streptomyces* spp. and *E. coli*. Food Technology and Biotechnology 39: 49–53.

*Vibrio cholerae* cells can be transformed as described in Panda D K, Banerjee R, Das J. 1995. Construction of shuttle vectors for cloning in *vibrio cholerae* and *Escherichia coli*. Journal of Biosciences 20: 367–376.

*Haemophilus ducreyi* cells can be transformed as described in Hansen E J, Latimer J L, Thomas S E, Helminen M, Albritton W L, Radolf J D. 1992. Use of electroporation to construct isogenic mutants of *Haemophilus ducreyi*. Journal of Bacteriology 174: 5442–5449; and Windsor H M, Gromkova R C, Koornhof H J. 1993. Transformation of v-factor independence from *Haemophilus ducreyi* to *haemophilus influenzae* and *haemophilus parainfluenzae*. Medical Microbiology Letters 2: 159–167.

The invention also encompasses (i) an expression cassette or vector as described above, for expression of the polypeptide or polypeptide derivative encoded by a polynucleotide, which polypeptide is outer-membrane localized; and (ii) a prokaryotic cell transformed with the expression cassette or vector and which expresses the polypeptide at the cell surface.

In embodiments where the polypeptide is a fusion between a carrier protein and a passenger protein, the passenger protein should be accessible at the surface, as can be determined by tests such as protease accessibility assays or radio-iodination.

A recombinant expression system is selected from procaryotic and eucaryotic hosts, preferably procaryotic. Eucaryotic hosts include yeast cells (e.g., *Saccharomyces cerevisiae* or *Pichia pastoris*); mammalian cells (e.g., COS1, NIH3T3, or JEG3 cells), and plant cells. Prokaryotic hosts include Gram-negative bacteria, and include specifically: *Agrobacteria*, preferably *A. tumefaciens, Rhizobium, Brucella, Bartonella hensela, Pasteurella haemolytica, Mycobacterium tuberculosis, Haemophilus ducreyi, Pseudomonas, E. coli, Klebsiella, Erwinia, Shigella, Salmonella, Vibrio cholerae, Lactobacillus*, Bacille bilié de Calmette-Guérin (BCG), and *Streptococcus*, preferably non-toxicogenic *Vibrio cholerae* mutant strains and attenuated *Salmonella typhimurium* strains.

Bacterial and eucaryotic cells are available from a number of different sources including commercial sources to those skilled in the art, e.g., the American Type Culture Collection (ATCC; Rockville, Md.). Commercial sources of cells used for recombinant protein expression also provide instructions for usage of the cells.

Non-toxicogenic *Vibrio cholerae* mutant strains are known. U.S. Pat. No. 4,882,278 describes strains which have a substantial amount of the coding sequence of each of the two ctxA alleles deleted so that no functional cholerae toxin is produced. WO 92/11354 describes a strain in which the irgA locus is inactivated by mutation; this mutation can be combined in a single strain with ctxA mutations. WO 94/01533 describes a deletion mutant lacking functional ctxA and attRS1 DNA sequences. These mutant strains are genetically engineered to express heterologous proteins, as described in WO 94/19482.

Attenuated *Salmonella typhimurium* strains, genetically engineered for recombinant expression of heterologous proteins or not, are described in WO 92/11361.

Other bacterial strains used as protein expression hosts in the context of the present invention are described for *Shigella flexneri* in High et al., EMBO (1992) 11:1991 and Sizemore et al., Science (1995) 270:299; for *Streptococcus gordonii* in Medaglini et al., Proc. Natl. Acad. Sci. USA (1995) 92:6868; and for Bacille Calmette Guerin in Flynn J. L., Cell. Mol. Biol. (1994) 40 (suppl. I):31, WO 88/06626, WO 90/00594, WO 91/13157, WO 92/01796, and WO 92/21376.

The invention is typically practiced using one or more of the commonly available gram-negative bacteria as cell hosts. However, rough mutants having somewhat differing membrane compositions are expected to also be useful in the practice of the invention. Membranes with higher phospholipid content, for example, may for some fusion polypeptides, provide more efficient surface expression at higher temperatures. Alternatively, it may be desirable to anchor some polypeptides closer to the membrane surface with increased lipid-protein interactions, perhaps for the purpose of increasing immunogenic response or altering adsorbent properties. Such mutants, spontaneously generated or otherwise, are contemplated as useful as host cells and/or as sources for membrane directing and transversing sequences.

In bacteria, the polynucleotide of the invention is inserted into the bacterial genome or remains in a free state as part of a plasmid.

The choice of the expression system depends on the features desired for the expressed polypeptide. For example, it may be useful to produce a polypeptide of the invention in a particular lipidated form.

One skilled in the art would readily understand that not all vectors and expression control sequences and hosts would be expected to express equally well the polynucleotides of this invention. With the guidelines described below, however, a selection of vectors, expression control sequences and hosts may be made without undue experimentation and without departing from the scope of this invention.

In selecting a vector, the host must be chosen that is compatible with the vector which is to exist and possibly replicate in it. Considerations are made with respect to the vector copy number, the ability to control the copy number, expression of other proteins such as antibiotic resistance. In selecting an expression control sequence, a number of variables are considered. Among the important variable are the relative strength of the sequence (e.g. the ability to drive expression under various conditions), the ability to control the sequence's function, compatibility between the polynucleotide to be expressed and the control sequence (e.g. secondary structures are considered to avoid hairpin structures which prevent efficient transcription). In selecting the host, unicellular hosts are selected which are compatible with the selected vector, tolerant of any possible toxic effects of the expressed product, able to secrete to the outer membrane the expressed product efficiently if such is desired, to be able to express the product in the desired conformation, to be easily scaled up, and to which ease of purification of the final product.

The choice of the expression cassette depends on the host system selected as well as the features desired for the expressed polypeptide. Typically, an expression cassette includes a promoter that is functional in the selected host system and can be constitutive or inducible; a ribosome binding site; a start codon (ATG) if necessary; a region encoding a signal peptide, e.g., a lipidation signal peptide; a DNA molecule of the invention; a stop codon; and optionally a 3' terminal region (translation and/or transcription terminator). The signal peptide encoding region is adjacent to the polynucleotide of the invention and placed in proper reading frame. The signal peptide-encoding region is homologous or heterologous to the DNA molecule encoding the mature polypeptide and is compatible with the secretion apparatus of the host used for expression. The open reading frame constituted by the DNA molecule of the invention, solely or together with the signal peptide, is placed under the control of the promoter so that transcription and translation occur in the host system. Promoters and signal peptide encoding regions are widely known and available to those skilled in the art and include, for example, the promoter of *Salmonella typhimurium* (and derivatives) that is inducible by arabinose (promoter araB) and is functional in Gram-negative bacteria such as *E. coli* (as described in U.S. Pat. No. 5,028,530 and in Cagnon et al., (Cagnon et al., Protein Engineering (1991) 4(7):843)); the promoter of the gene of bacteriophage T7 encoding RNA polymerase, that is functional in a number of *E. coli* strains expressing T7 polymerase (described in U.S. Pat. No. 4,952,496); OspA lipidation signal peptide ; and RlpB lipidation signal peptide (Takase et al., J. Bact. (1987) 169:5692).

The expression cassette is typically part of an expression vector, which is selected for its ability to replicate in the chosen expression system. Expression vectors (e.g., plasmids) can be chosen, for example, from those described in Pouwels et al. (Cloning Vectors: A Laboratory Manual 1985, Supp. 1987). Suitable expression vectors can be purchased from various commercial sources.

Methods for transforming/transfecting host cells with expression vectors are well-known in the art and depend on the host system selected as described in Sambrook, J. E. F. et. al. (1989) Molecular Cloning a Laboratory Manual $2^{nd}$ ed. Cold Spring Harbor Laboratory Press, Cold Spring Harbor N.Y.

Upon expression, a recombinant polypeptide of the invention (or a polypeptide derivative) is produced and remains in the intracellular compartment, is secreted/excreted in the extracellular medium or in the periplasmic space, or is embedded in the membrane. The polypeptide is recovered in a substantially purified form from the cell extract or from the supernatant after centrifugation of the recombinant cell culture. Typically, the recombinant polypeptide is purified by antibody-based affinity purification or by other well-known methods that can be readily adapted by a person skilled in the art, such as fusion of the polynucleotide encoding the polypeptide or its derivative to a small affinity binding domain. Antibodies useful for purifying by immunoaffinity the polypeptides of the invention are obtained as described below.

The sequence information provided in the present application enables the design of specific nucleotide probes and primers that are used for diagnostic purposes. Accordingly, another aspect of the invention provides a nucleotide probe or primer having a sequence found in or derived by degeneracy of the genetic code from a sequence shown in SEQ ID NO: 1 or 3 or from a corresponding homologous sequence.

The term "probe" as used in the present application refers to DNA (preferably single stranded) or RNA molecules (or modifications or combinations thereof) that hybridize under the stringent conditions, as defined above, to nucleic acid molecules having SEQ ID NO: 1 or 3, or to their corresponding homologous, complementary or anti-sense sequences. Generally, probes are significantly shorter than full-length sequences. Such probes contain from about 5 to about 100, (for example, 10, 12, 15, 20, 25, 30, 35, 40, 45, 50, 55, 60 . . . and so forth), preferably from about 10 to about 80, nucleotides. In particular, probes have sequences that are at least 75% (for example at least 80%, 85%, 90%, 95%, 96%, 97%, 98%, 99%), and preferably at least 95% homologous to a portion of SEQ ID NO: 1 or 3. Probes may also have sequences that are complementary to such sequences and portions. Probes may contain modified bases such as inosine, methyl-5-deoxycytidine, deoxyuridine, dimethylamino-5-deoxyuridine, or diamino-2,6-purine. Sugar or phosphate residues may also be modified or substituted. For example, a deoxyribose residue may be replaced by a polyamide (Nielsen et al., Science (1991) 254:1497) and phosphate residues may be replaced by ester groups such as diphosphate, alkyl, arylphosphonate and phosphorothioate esters. In addition, the 2'-hydroxyl group on ribonucleotides may be modified by including such groups as alkyl groups.

Probes of the invention are used in diagnostic tests, as capture or detection probes. Such capture probes are conventionally immobilized on a solid support, directly or indirectly, by covalent means or by passive adsorption. A detection probe is labelled by a detection marker selected from: radioactive isotopes, enzymes such as peroxidase, alkaline phosphatase, and enzymes able to hydrolyze a chromogenic, fluorogenic, or luminescent substrate, compounds that are chromogenic, fluorogenic, or luminescent, nucleotide base analogs, and biotin.

Probes of the invention are used in any conventional hybridization technique, such as dot blot (Maniatis et al., Molecular Cloning: A Laboratory Manual (1982) Cold Spring Harbor Laboratory Press, Cold Spring Harbor, N.Y.), Southern blot, northern blot, or the sandwich technique (Dunn et al., Cell (1977), 12:23). The latter technique involves the use of a specific capture probe and/or a specific detection probe with nucleotide sequences that at least partially differ from each other.

A primer is a probe of usually about 10 to about 40 nucleotides (for example, 11, 12, 13, 14, 15, 17, 20, 25, 30 or 35 nucleotides) that is used to initiate enzymatic polymerization of DNA in an amplification process (e.g., PCR), in an elongation process, or in a reverse transcription method. Primers used in diagnostic methods involving PCR are labeled by methods known in the art.

As described herein, the invention also encompasses (i) a reagent comprising a probe of the invention for detecting and/or identifying the presence of *Agrobacterium* in a biological material; (ii) a method for detecting and/or identifying the presence of *Agrobacterium* in a biological material. In one embodiment, the detecting or identifying method involves the following steps: (a) a sample is recovered or derived from the biological material, (b) DNA or RNA is extracted from the material and denatured, and (c) exposed to a probe of the invention, for example, a capture, detection probe or both, under stringent hybridization conditions, such that hybridization is detected. In another embodiment, the detecting or identifying method involves the following steps: (a) a sample is recovered or derived from the biological material, (b) DNA is extracted therefrom, (c) the extracted DNA is primed with at least one, and preferably two, primers of the invention and amplified by polymerase chain reaction, and (d) the amplified DNA fragment is produced.

It is apparent that disclosure of polynucleotide sequences of SEQ ID NO: 1 or 3, their homologs and partial sequences, enable their corresponding amino acid sequences. Accordingly, the invention also encompasses substantially purified polypeptides or polypeptide derivatives having an amino acid sequence encoded by a polynucleotide of the invention.

A "substantially purified polypeptide" as used herein is defined as a polypeptide that is separated from the environment in which it naturally occurs and/or that is free of the majority of the polypeptides that are present in the environment in which it was synthesized. For example, a substantially purified,polypeptide is free from cytoplasmic polypeptides. One band among a number of bands on an SDS-PAGE gel, for example, would not constitute a "substantially purified polypeptide" since the gel sample contains a number of polypeptide species. Those skilled in the art would readily understand that the polypeptides of the invention may be purified from a natural source, i.e., a *Agrobacterium* strain, or produced by recombinant means.

The invention encompasses polypeptides, homologs or fragments which are modified to retain or improve their ability to display passenger proteins to the cell surface. Such modifications include those amino acid substitutions, deletions and insertions as described above which do not alter the inherent topology and membrane targeting ability of the protein to the cell surface.

The polypeptide or polypeptide derivative may be produced and purified using known laboratory techniques for generating antibodies. As described above, the polypeptide or polypeptide derivative may be produced as a fusion protein containing a fused tail that facilitates purification. The fusion product is used to immunize a small mammal, e.g., a mouse or a rabbit, in order to raise antibodies against the polypeptide or polypeptide derivative (monospecific antibodies). Accordingly, the invention also provides a monospecific antibody that binds to a polypeptide or polypeptide derivative of the invention.

By "monospecific antibody" is meant an antibody that is capable of reacting with a specific protein of the invention, i.e. a specific carrier protein such as AopB or a fragment or homolog thereof. An antibody of the invention is either polyclonal or monoclonal. Monospecific antibodies may be recombinant, e.g., chimeric (e.g., constituted by a variable region of murine origin associated with a human constant region), humanized (a human immunoglobulin constant backbone together with hypervariable region of animal, e.g., murine, origin), and/or single chain. Both polyclonal and monospecific antibodies may also be in the form of immunoglobulin fragments, e.g., F(ab)'2 or Fab fragments. The antibodies of the invention are of any isotype, e.g., IgG or IgA, and polyclonal antibodies are of a single isotype or a mixture of isotypes.

Antibodies against the polypeptides, homologs or fragments of the present invention are generated by immunization of a mammal with a composition comprising said polypeptide, homolog or fragment. Such antibodies may be polyclonal or monoclonal. Methods to produce polyclonal or monoclonal antibodies are well known in the art. For a review, see Antibodies, A Laboratory Manual, Cold Spring Harbor Laboratory, Eds. E. Harlow and D. Lane (1988), and D. E. Yelton et al., 1981. Ann. Rev. Biochem. 50:657–680. For monoclonal antibodies, see Kohler & Milstein (1975) Nature 256:495–497.

The antibodies of the invention, which are raised to a polypeptide or polypeptide derivative of the invention such as AopB, are produced and identified using standard immunological assays, e.g., Western blot analysis, dot blot assay, or ELISA (Sambrook, J. E. F. et. al. (1989) Molecular Cloning a Laboratory Manual $2^{nd}$ ed. Cold Spring Harbor Laboratory Press, Cold Spring Harbor N.Y.). The antibodies are used in diagnostic methods to detect the presence of *Agrobacterium* in a sample, such as a biological sample. The antibodies are also used in affinity chromatography for purifying a polypeptide or polypeptide derivative of the invention.

Accordingly, the invention also provides (i) a reagent for detecting the presence of *Agrobacterium* in a biological sample that contains an antibody, polypeptide, or polypeptide derivative of the invention; and (ii) a diagnostic method for detecting the presence of *Agrobacterium* in a biological sample, by contacting the biological sample with an antibody, a polypeptide, or a polypeptide derivative of the invention, such that an immune complex is formed, and by detecting such complex to indicate the presence of *Agrobacterium* in the sample or the organism from which the sample is derived.

Those skilled in the art will readily understand that the immune complex is formed between a component of the sample and the ant-body, polypeptide, or polypeptide derivative, whichever is used, and that any unbound material is removed prior to detecting the complex.

For diagnostic applications, the reagent (i.e., the antibody, polypeptide, or polypeptide derivative of the invention) is either in a free state or immobilized on a solid support, such as a whole cell, a tube, a bead, or any other conventional support used in the field. Immobilization is achieved using direct or indirect means. Direct means include cell surface expression of the reagent, passive adsorption (non-covalent binding) or covalent binding between the support and the reagent. By "indirect means" is meant that an anti-reagent compound that interacts with a reagent is first attached to the solid support.

Another aspect of the invention provides a process for purifying, from a biological sample, a polypeptide or polypeptide derivative of the invention, which involves carrying out antibody-based affinity chromatography with the biological sample, wherein the antibody is a monospecific antibody of the invention.

For use in a purification process of the invention, the antibody is either polyclonal or monospecific, and preferably is of the IgG type. Purified IgGs is prepared from an antiserum using standard methods. Conventional chromatography supports, as well as standard methods for grafting antibodies, are described in, e.g., Antibodies: A Laboratory Manual, D. Lane, E. Harlow, Eds. (1988) and outlined below.

Briefly, a biological sample, such as a RopB-containing extract of *Rhizobium leguminosarum*, preferably in a nonionic detergent-containing buffer solution, is applied to a chromatography material, preferably equilibrated with the buffer used to dilute the biological sample so that the polypeptide or polypeptide derivative of the invention (i.e., the antigen) is allowed to adsorb onto the material. The chromatography material, such as a gel or a resin coupled to an antibody of the invention, is in either a batch form or a column. The unbound components are washed off and the antigen is then eluted with an appropriate elution buffer, such as a glycine buffer or a buffer containing a chaotropic agent, e.g., guanidine HCl, or high salt concentration (e.g., 3 M $MgCl_2$). Eluted fractions are recovered and the presence of the antigen is detected, e.g., by measuring the absorbance at 280 nm.

The present invention also relates to an isolated DNA at the 5' region of the aopB gene and having promoter activity. More specifically, the invention relates to an aopB promoter comprising the functional elements found in the region of nucleotides 6 to 309 of SEQ ID No: 1. The promoter DNA of the present invention comprises at least part of the nucleotide sequence of the 5' flanking region of the transcriptional start sites of aopB. In a preferred embodiment, the promoter DNA of the invention comprises a transcriptional regulation site which allows the promoter to be induced by acidic pH.

B. Surface Display

An aspect of the invention relates to a bacterial cell surface display system. In one embodiment, the *A. tumefaciens* outer membrane protein AopB is used as the carrier protein and *A. tumefaciens* as the host. Experimental data based on whole cell ELISA, immunofluorescence microscopy, flow cytometry and protease accessibility assays using as passenger proteins two reporter proteins, jelly fish green fluorescence protein (GFP) and *Escherichia coli* alkaline phosphatase (PhoA), show that both proteins were directed to the bacterial cell surface.

In one aspect, the invention provides a display system which permits display of passenger proteins in a native state. By "native state" is meant that at least one activity (e.g. enzyme activity) or structural feature (e.g. binding site or antibody epitope) of the passenger protein is retained in the displayed protein, compared to the naturally-occurring or reference state. Both GFP and PhoA were directed to the surface without addition of reducing reagent or any special condition to minimize formation of disulphide bonds. The PhoA protein displayed on the cell surface was enzymatically active, even though the active state of PhoA is dimeric and requires formation of intramolecular disulfide bonds, which can interfere with the display process in other display systems.

At least 4 permissive sites in AopB (amino acids 125, 134, 172, and 207 of SEQ ID No:2) were able to efficiently display the PhoA protein onto the cell surface. Only the N-terminal but not the C-terminal part of AopB was required for the display process, which differs from other display carrier proteins. A surface display vector containing a multiple cloning site was constructed that can conveniently display passenger proteins at the position of amino acid 172 of AopB. Other display vectors can also be constructed to display passenger proteins at other amino acid positions of AopB.

In another aspect, the invention provides a display system which can be regulated by pH when the fusion protein is under control of the aopB promoter. Expression of a aopB-gfp fusion in mutant CGI1 cells from the native aopB promoter was shown to be strong at acidic pH but not at neutral pH, suggesting that the aopB promoter is inducible by acidic pH. By acidic pH is meant a pH less than 7; however, it is understood to those skilled in the art that the choice of acidic pH should take into account factors such as viability of the cells, effects on the protein export machinery of the cell, as well as compatibility of the chosen pH with the desired folding of the passenger protein. In a preferred embodiment, the pH used to induce surface expression of the fusion protein is about 5.5. Regulated expression of the fusion protein may be conveniently used to display on a cell a passenger protein which is potentially toxic to the cell. In a preferred embodiment, the regulated display system uses the aopB promoter to express the fusion protein in *Agrobacteria*, preferrably *A. tumefaciens*.

To effect fusion between the carrier and the passenger protein, the passenger polypeptide is fused to the N-terminus, or preferably, to the C-terminus of the polypeptide of the invention. The fusion may contain a linker peptide or a protease-susceptible site between the carrier and the passenger.

For purposes of display, the hybrid precursor polypeptides may contain heterologous signal peptides. Preferred heterologous signal peptides are those of, or derived from, Gram-negative bacteria. In preferred embodiments, the heterologous signal peptides are joined to the N-terminus of the mature sequence of the carrier protein. Preferred signal peptides include the signal sequence of AopB, specifically amino acids 1–23 of SEQ ID NO:2 or variants and homologs thereof preferably from other *Agrobacterium* species.

Other useful signal peptides include the Lpp targeting sequence, which include the signal sequence and the first 9 amino acids of the mature protein. Examples of other proteins that may serve as sources of secretion and membrane localization signals include *E. coli* outer membrane lipoproteins such as TraT, OsmB, NlpB, BlaZ; *Pseudomonas aeruginosa* lipoprotein 1; *Haemophilus influenza* PA1 and PCN proteins; *Rickettsia rickettsii* 17 kDa lipoprotein; *Neisseria gonorrhea* H.8 protein.

The AopB-based display system can be regulated by the pH of the growth medium. The efficiency of display was highest when the bacteria were grown in an acidic minimal medium, while the display was lower when the bacteria were grown in a neutral minimal or rich medium. The AopB-based *Agrobacterium* display represents a controllable display system that can directly display dimeric or multi-subunit proteins like PhoA (with disulfide bonds) in an active state, in addition to displaying monomeric proteins. This system offers a simple, economic, and efficient display system that can provide enhanced diversity and efficacy of displayed molecules.

The invention encompasses not only AopB as a carrier for surface display, but also encompasses AopB fragments, preferably N-terminal fragments of AopB, homologs and variants, as well as AopB-related membrane proteins which have homology to AopB. AopB-related membrane proteins include RopB of *R. leguminosarum* (60% amino acid sequence similarity), the immunogenic outer membrane proteins of *Brucella* species (42–47% amino acid sequence similarity), Pap31 of *Bartonella hensela* infected with a bacteriophage (46% amino acid sequence similarity), *Pasteurella haemolytica* outer membrane protein PomA (47% amino acid sequence similarity), PPE of *Mycobacterium tuberculosis* (39% amino acid sequence similarity), *Haemophilus ducreyi* major outer membrane protein (43% amino acid sequence similarity), and the outer membrane porin of *Vibrio cholerae* (40% amino acid sequence similarity), as well as the C-terminal half of the porin protein F (OprF) of *Pseudomonas* species AopB-related membrane proteins include those fragments which are functional for display of passenger proteins. Based on homology analysis, it is contemplated that for AopB-related membrane proteins of about the same size as AopB, i.e. 20 kDa to 24 kDa, fragments which are useful as a carrier protein for display comprise at least the N-terminal 150 to 220 amino acids of the naturally occurring AopB-related membrane protein.

A person skilled in the art will readily understand that by performing the following steps, one can optimize the fragment size of the AopB-related membrane protein, for use as a carrier protein. A typical assay comprises the steps of:

(i) joining a reporter (passenger) protein such as GFP in-frame with the test fragment, which is the putative carrier protein. Conveniently, nucleic acid molecules encoding the reporter and the test fragment are joined in-frame to create a fusion protein. The nucleic acid encoding the fusion protein is then inserted into an expression vector for expressing the fusion protein in the bacterium in step (ii);

(ii) transforming a Gram-negative bacterium, preferably a bacterium of the same species as that of the putative carrier protein, with the nucleic acid encoding the fusion protein; and (iii) assaying the transformed bacteria for reporter protein activity using an assay suitable for whole cells, such as FACS. A high level of reporter protein activity at the cell surface would indicate that the fragment is optimally useful as a carrier protein for display.

The sequence of RopB, a 22 kDa outer membrane protein of *Rhizobium leguminosarum*, may be obtained at EMBL accession numbers X80767 or AJ007906.

Various outer membrane proteins of *Brucella* include: OM25_BRUME 25 kDa outer membrane protein (EMBL acc. no. U33003) of *Brucella melitensis*, OM25_BRUCA 25 kDa outer membrane protein (EMBL acc. no. U39358) of *B. melitensis* biovar Canis, OM25_BRUSU 25 kDa outer membrane protein (EMBL acc. no. U39397) of *B. melitensis* biovar Suis, OM25_BRUAB 25 kDa major outer membrane protein precursor (EMBL acc. no. X79284) of *B. melitensis* biovar Abortus, OM25_BRUNE 25 kDa outer membrane protein (EMBL acc. no. U39359) of *B. melitensis* biovar Neotomae, OM25_BRUOV 25 kDa outer membrane protein (EMBL acc. no. U33004) of *B. melitensis* biovar Ovis, the outer membrane protein (EMBL acc. no. AJ313014) of *B. melitensis* biovar Abortus, and OM31_BRUME 31 kDa outer membrane protein (EMBL acc. no. AF076290) of *B. melitensis*.

The sequence of the 31K major protein, Pap31 of *Bartonella henselae* phage 60457 may be found at EMBL accession numbers: AF001274; AF308165; AF308166; AF308167; AF308168; AF308169; and AF308170.

The sequence of outer membrane protein PomA of *Pasteurella haemolytica* may be found at EMBL accession number AF133259 (*Mannheimia haemolytica*).

The sequence of PPE of *Mycobacterium tuberculosis* may be found at EMBL accesion numbers AL009198 or AL008967 (PE_PGRS).

The sequence of the putative outer membrane porin of *Vibrio cholerae* may be found at EMBL accession number AF030977.

The sequence of the major outer membrane protein of *Haemophilus ducreyi* may be found at EMBL accesion number U60646.

Bacteria useful as host for display of passenger proteins include Gram-negative bacteria, and include but are not limited to: *Agrobacteria*, preferably *A. tumefaciens, Rhizobium, Brucella, Bartonella hensela, Pasteurella haemolytica, Mycobacterium tuberculosis, Haemophilus ducreyi, Pseudomonas, E. coli, Klebsiella, Erwinia, Shigella, Salmonella, Vibrio cholerae, Lactobacillus*, Bacille bilié de Calmette-Guérin (BCG), and *Streptococcus*, preferably non-toxicogenic *Vibrio cholerae* mutant strains and attenuated *Salmonella typhimurium* strains.

The carrier proteins of the invention are preferably used in display-compatible hosts. By "display-compatible" is meant that the combination of carrier protein and the host cell is effective in displaying passenger proteins. For example, the combination of *A. tumefaciens* as a host cell and AopB as carrier protein is display compatible, whereas the combination of *E. coli* and and AopB, or *R. meliloti* RCR2011 and AopB, is not. Display compatibility can be readily determined by expressing the fusion of carrier and passenger protein (conveniently a reporter protein) in the host cell of interest, and assaying for the presence of the fusion protein on the cell surface.

AopB, fragments, variants and AopB-related membrane proteins are preferably used in their native hosts for surface display. Homologs and their variants may be used in the following embodiments: RopB may be used as the carrier in *Rhizobium*; the immunogenic outer membrane proteins in *Brucella* species used in *Brucella*; Pap31 of *B. hensela* used in *Bartonella*, preferably *B. hensela*; P. outer membrane protein PomA used in *Pasteurella*, preferably *P. haemolytica*; PPE of *M. tuberculosis* used in *Mycobacterium*, preferably *M. tuberculosis*; *H. ducreyi* major outer membrane protein used in *Haemophilus*, preferably *H. ducreyi*; the outer membrane porin of *V. cholerae* used in *Vibrio*, preferably *V. cholerae*; and the porin protein F (OprF) of *Pseudomonas* used in *Pseudomonas*.

In one embodiment, AopB, its homologs and variants as well as fusions, are expressed under control of the native promoter of aopB. In other embodiments, the AopB-related membrane proteins and fragments are expressed for the purpose of displaying a passenger proteins under control of their native promoter; e.g. RopB would be expressed under control-of the ropB promoter.

The cell surface display system of the invention can be employed for various applications, including:

(I) Live vaccine development. In this application, the passenger protein may contain epitopes which may be presented to the immune system to elicit an immune response;

(II) Peptide library screening. In this application, peptide libraries may be displayed and screened by sequential binding and elution, or by fluorescence-activated cell sorting;

(III) Bioadsorption. In this application, whole cells displaying a passenger protein which can bind to a ligand may be used to remove the ligand from solution;

(IV) Purification. In this application, whole cells displaying a passenger protein which can bind to a ligand or receptor may be used as a affinity matrix to purify the ligand or receptor;

(V) Whole cell catalysis. In this application, enzymes may be immobilized on the cell surface and the cell used for solid-phase catalysis of biochemical reactions.

C. Vaccines

Non-recombinant live vaccines have been used for many years for large scale vaccinations, for example, live attenuated cultures of *Baccillus* Calmette-Guerin (BCG) which confer immunity against tuberculosis.

Recently, emphasis has been shifted to the development of recombinant bacterial vaccines. In this case vaccination consists of the oral administration of a live culture of an attenuated enteric bacterium host such as *E. coli* or *Salmonella typhimurium* which expresses an antigenic peptide from a pathogen. Within the body, some of the bacteria find their way to the intestinal tract where they coexist with the wild type *E. coli* and other enteric microorganisms. In this way they ensure the presence of a low level of antigenic peptide in the body. Thus live vaccines provide potentially more efficient immunity and longer protection against infections compared to subunit or killed bacterial vaccines.

Although the antigen may stimulate an immune response even when produced within the cell, the immunogenicity of peptide antigens can be greatly enhanced if they are expressed on the surface of an appropriate host strain, presumably because the surface of the bacteria such as *Salmonella* or *E. coli* acts as an adjuvant to enhance the immune response to the antigen. Antigens which are exposed on the bacterial cell surface may be more easily recognised by the immune system (compared to antigens which are only released following bacterial death and degradation), since surface antigens are more accessible to their receptors on antigen-recognising and processing cells (macrophages, dendritic cells and B lymphocytes).

The display method of the present invention can thus be used for the surface expression of antigens in Gram-negative bacteria. In a preferred embodiment, the antigen-displaying cell is a cell of the genus *Agrobacterium* or *Rhizobium* for use as a live vaccine since *Agrobacterium* or *Rhizobium* are harmless to mammals including humans. Live vaccines made from these bacteria should be safer compared to genetically weakened (attenuated) strains of human pathogenic bacteria.

Other host cells which may serve as live bacterial vectors for displaying passenger antigens include: *Shigella, Salmonella, Vibrio cholerae, Lactobacillus*, Bacille bilié de Calmette-Guérin (BCG), and *Streptococcus*, which are known in the art.

Since *Agrobacterium* and *Rhizobium* can survive well in the wild, AopB-based and RopB-based display technology may be used to produce live vaccines for fish, which may have to be released into the water.

Non-toxicogenic *Vibrio cholerae* mutant strains that are useful as a live oral vaccine are known. U.S. Pat. No. 4,882,278 describes strains which have a substantial amount of the coding sequence of each of the two ctxA alleles deleted so that no functional cholerae toxin is produced. WO 92/11354 describes a strain in which the irgA locus is inactivated by mutation; this mutation can be combined in a single strain with ctxA mutations. WO 94/01533 describes a deletion mutant lacking functional ctxA and attRS1 DNA sequences. These mutant strains are genetically engineered to express heterologous antigens, as described in WO 94/19482. An effective vaccine dose of a *Vibrio cholerae* strain capable of expressing a polypeptide or polypeptide derivative encoded by a DNA molecule of the invention contains about $1\times10^5$ to about $1\times10^9$, preferably about $1\times10^6$ to about $1\times10^8$, viable bacteria in a volume appropriate for the selected route of administration. Preferred routes of administration include all mucosal routes; most preferably, these vectors are administered intranasally or orally.

Attenuated *Salmonella typhimurium* strains, genetically engineered for recombinant expression of heterologous antigens or not, and their use as oral vaccines are described in WO 92/11361. Preferred routes of administration include all mucosal routes; most preferably, these vectors are administered intranasally or orally.

Other bacterial strains used as vaccine vectors in the context of the present invention are described for *Shigella flexneri* in High et al., EMBO (1992) 11:1991 and Sizemore et al., Science (1995) 270:299; for *Streptococcus gordonii* in Medaglini et al., Proc. Natl. Acad. Sci. USA (1995) 92:6868;

and for Bacille Calmette Guerin in Flynn J. L., Cell. Mol. Biol. (1994) 40 (suppl. I):31, WO 88/06626, WO 90/00594, WO 91/13157, WO 92/01796, and WO 92/21376.

In bacterial vectors, the polynucleotide of the invention is inserted into the bacterial genome or remains in a free state as part of a plasmid.

A variety of antigenic determinants may be expressed on a cell surface in combination with an activating agent such as IL-4 on the surface of a bacterium to further stimulate an immune response to a surface exposed antigen.

Live bacterial vaccines are conventionally administered parenterally, by injection or in oral formulation. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10–95% of active ingredient, preferably 25–70%.

The vaccines are administered in a manner compatible with the dosage formulation, and in such amount as will be therapeutically effective and immunogenic. The quantity to be administered depends on the subject to be treated, including, e.g., the capacity of the individual's immune system to synthesize antibodies, and the degree of protection desired. Precise amounts of active ingredient required to be administered depend on the judgment of the practitioner. However, suitable dosage ranges are of the order of several hundred micrograms active ingredient per vaccination. Suitable regimes for initial administration and booster shots are also variable but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the size of the host.

In many instances, it will be desirable to have multiple administrations of the vaccine, usually not exceeding six vaccinations, more usually not exceeding four vaccinations and preferably one or more, usually at least about three vaccinations. The vaccinations will normally be from two to twelve week intervals, more usually from three to five week intervals. The course of the immunization may be followed by assays for antibodies for the supernatant antigens. The assays may be performed by labeling with conventional labels, such as radionuclides, enzymes, fluorescers, and the like. These techniques are well known and may be found in a wide variety of patents, such as U.S. Pat. Nos. 3,791,932; 4,174,384 and 3,949,064, as illustrative of these types of assays.

D. Library Screening

The cell surface display system may be used to screen a library for a protein with a desired property. By transforming a host organism with an expressible fusion of the carrier nucleic acid and a library of nucleic acids encoding candidate passenger proteins, a population of host cells displaying the candidate proteins on the cell surface may be screened for the desired function, e.g. specific binding to a ligand such as an antibody or antigen. The screening may be performed by means such as affinity separation techniques, including affinity column chromatography, batch elution from affinity matrix material and fluorescent-activated cell sorting (FACS).

Specific members of a bacterial display library produced with the present invention can be selected by FACS, which allows bacteria expressing the desired passenger protein to be detected using a fluorescent counter ligand as a probe. The bacteria could then be obtained free of non-expressor cells using a FACS machine capable of soring single bacteria.

Screening for antibodies employing the methods of the present invention allows one to select an antibody or antibody fragment from a plurality of candidate antibodies that have been expressed on the surface of a host cell. The antibodies are obtained from an expression vector library that may be prepared from DNAs encoding antibodies or antibody fragments. One source of such DNAs could be from an animal immunized with a selected antigen; alternatively, antibody genes from other sources can be used, such as those produced by hybridomas or produced by mutagenesis of a known antibody gene. One preferred method of obtaining DNA segments is to isolate mRNA from antibody cells of an immunized animal. The mRNA may be amplified, for example by PCR, and used to prepare DNA segments to include in the vectors. DNA segments that have been mutagenized from one or more DNAs that encode a selected antibody or antibody fragment may also be used.

Once an antibody expression library is prepared, the selected antigen for which one desires to identify and isolate specific antibody or antibodies is labeled with a detectable label. There are many types of detectable labels, including fluorescent labels. The labeled antigen is contacted with the cells displaying the antibody expression library under conditions that allow specific antigen-antibody binding. Conditions can be varied so that only very tightly binding interactions occur; for example, by using very low concentrations of labeled antigen.

Identifying the antibody or antibody fragment expressing cells may be accomplished by methods that depend on detecting the presence of the bound detectable label. A particularly preferred method for identification and isolation is cell sorting or flow cytometry such as FACS.

Identification of antibody expressing bacteria by FACS is directly based on the-affinity for the soluble hapten thus eliminating artifacts due to binding on solid surfaces. This means only the high affinity antibodies are recovered by sorting following binding of low concentrations of fluorescently labeled antigen. The sorting of positive clones is essentially limited only by the accuracy of the flow cytometer.

Specific members of a bacterial display library produced with the present invention can also be selected by affinity chromatography, in which the ligand specific to the desired passenger protein is bound on a matrix. Because bacterial cells are larger, loading must be done carefully to prevent plugging by non-specific retention of bacteria in the column. After loading and equilibrating the column under conditions sufficient for the desired passenger protein to bind to the matrix-bound ligand, the cells can be eluted either by passing free ligand through the column or by low pH.

The host cells displaying the desired passenger protein may then be further cultured and used to obtain the fusion protein. If desired, the passenger protein may be separated from the carrier protein by means of protease cleavage, if a protease-specific site was built into the junction between the carrier and the passenger.

Once a desired passenger protein has been displayed, the DNA encoding the passenger polypeptide may be mutated,. e.g., by use of a mutator strain. Affinity separation may then be applied again to identify and select the desired mutant.

A "library" of recombinant immunoglobulins containing both heavy and light variable domains could be generated by bacteria, so that the proteins have antigen-binding affinity comparable to the corresponding natural antibodies. Furthermore, since random sequences can be introduced into the antibodies-coding DNA fragments, the variety of recombinant immunoglobulins from bacteria is potentially greater than the number of antibody molecules that can be generated by mammalian cells, so that a greater repertoire of antibodies can be made. Display of the antibody molecules on the surfaces of the bacterial cells can facilitate the selection of high affinity antibody molecules for specific antigens. Therefore, the AopB-based system can be used to generate libraries of antibody molecules and subsequently to select the high affinity antibody molecules.

The display method of the present invention can be used for the detection and characterization of recombinant proteins. For example, the method can be used to map an uncharacterized epitope. As an illustration, sequences encoding either a library of (1) random peptides or (2) peptides derived from an immunoreactive protein of interest can be cloned into an expression vector of the invention to express fusions with AopB. Host cells which are display-compatible with AopB are then transformed with the vector bank and the peptide library-AopB fusion proteins are displayed on the bacterial cell surface. Following growth on a solid-substrate, the resulting bacteria are screened for expression of the fusion protein that react with labeled antibody. Reactive colonies can then be picked and the vectors isolated. Sequence analysis of the DNA insert would reveal which of the cloned peptides sequences corresponded to the epitopes recognized by the antibody.

The display method of the present invention can also be used for detecting recombinant protein activity e.g., antibodies. For example, the method can readily be applied to screening libraries of recombinant antibody-AopB fusion proteins. These libraries may include combinatorial single-chain gene banks of heavy and light variable region genes or mutational libraries of specific recombinant antibody genes. The desired properties to be detected include binding activities, catalytic activities, inhibitory activities and altered structural conformations.

The present invention can also be used as a primary cloning system. For example, a cDNA library can be constructed and inserted in a vector of the present invention and the library screened for the ability to bind a ligand. The ligand/binding molecule combination could include any pair of molecules with an ability to specifically bind to one another, e.g., receptor/ligand, enzyme/substrate (or analog), nucleic acid binding protein/nucleic acid, etc. If one member of the complementary pair is available, this may be a preferred way of isolating a clone for the other of the pair.

E. Bio-Adsorption

The display method of the invention is applicable for removing contaminants from fluids. In this method receptor I proteins expressed on the outer membranes of gram-negative bacteria may be used to selectively interact with a wide variety of undesirable compounds. Metallothionein, for example, binds with a wide variety of heavy metals including iron, cadmium, zinc, copper, vanadium, and similar metals. When bound to the surface of a gram-negative organism this protein is expected to efficiently remove heavy metals from aqueous samples.

Thus one example of a passenger protein which may be used as a bio-adsorbent is metallothionein, of which the human form has been expressed as a fusion with an outer membrane protein (Jacobs et al. Gene 83, 95 (1989)). Because of the way the fusion protein was constructed, metallothionein was localized on the internal side of the $E.$ $coli$ outer membrane and facing the periplasmic space. Nevertheless, since metal ions can diffuse through the outer membrane, the recombinant cells were able to bind as much as 66 fold more $Cd^{+2}$ than normal $E.$ $coli.$ Whole cells which display polypeptides such as selected antibodies, may be also used as adsorbents to remove biological contaminants, for example, bacterial endotoxin from water samples or to remove viral impurities from blood products. The efficiency of such whole cell adsorbents may be increased by cross-linking the bacterial surface. This also may increase the stabilization of the cells against disruption. One method of stabilization involves the specific cross-linking of the cells through the lipopolysaccharide component of the surface. Thus the cells can be aggregated and stabilized without affecting the function of surface-displayed proteins. Other types of cell adsorbents are contemplated including the use of cellulose binding domains, starch binding domains, protein A, lectins, or protease receptors expressed on outer membrane bacterial cell surfaces.

A major constraint in the development of whole cell adsorbents is the availability of bacterial strains with suitable ligands on their surface. According to the display methods of the invention, it should be possible to generate libraries of different peptides of diverse sequences on the bacterial cell surfaces. The cells displaying the peptide(s) that has the high affinity for a specific target molecule can be selected using FACS. The suitable ligands for whole cell adsorbents can be both selected and displayed with the AopB-based system.

In a preferred embodiment, *Agrobacterium* and *Rhizobium*, which possess AopB and the homolog RopB respectively, are used as host cells for bio-adsorption. Bacteria of both genuses can survive well in the wild for many years without much nutrition. *Agrobacterium* and *Rhizobium* cells may be used to select and display on the bacterial surface passenger proteins which bind to hazardous molecules. The displaying cells can be used directly to remove the hazardous molecules from the environment.

F. Purification

Affinity purifications of biomolecules rely primarily on the strong interactions between proteins and ligands. Typically, the ligand is bound to a solid support matrix which is employed in a chromatographic-type separation. More recently, suspensions of starch granules or liposomes have been used as supports for affinity purifications. In some of the most useful and specific separations, the affinity ligands are proteins such as antibodies, lectins or protein receptors. The preparation of protein affinity adsorbents involves the production, purification and the immobilization of the polypeptide on a solid support matrix. These three steps are generally complicated and often prohibitively expensive for large scale applications.

Bacterial cells expressing proteins on their surface can serve as an important source of low cost solid phase affinity matrices. In a preferred embodiment, the affinity matrix comprises whole bacteria on which antibodies are displayed, for use in purifying antigens specific to the antibodies.

Conversely, antigen-displaying whole cells may be used as an affinity matrix to purify antibodies specific to the antigen.

G. Whole Cell Catalysis

The display methods of the invention may be used to immobilize enzymes. Any one of a wide variety of biocatalytically active polypeptides may be expressed on the surface of a bacterial cell using the methods described above. Advantages of having an enzyme expressed on the bacterial cell surface include increased accessibility to substrates, stability, and potentially increased lipid solubility. In a more particular embodiment, biocatalytically active polypeptides immobilized on host cell membranes without additional bacterial host cell components may be used in biphasic reaction systems. Enhanced lipid solubility of the immobilized enzymes enables catalyst substrate interaction in the lipophilic solvents with extraction of the water soluble products into the aqueous phase. Further contemplated embodiments in such an immobilized system include encapsulating immobilized enzymes on membrane surfaces within liposomes or similar vesicles.

The use of whole cells as enzymatic catalysts has been in use for several years. Typically, a microorganism which produces a certain enzyme is used as a biocatalyst, thus avoiding the costs associated with protein purification and immobilization steps. Usually the cells are first killed, treated with a permeabilizing agent to allow the diffusion of reactants and products into the cytoplasm and finally they are stabilized using some form of chemical crosslinking. Several improvements-on the preparation of whole cell biocatalyst have been made over the years. However, certain inherent limitations can not be overcome with the currently available technology. First, the chemical methods which are used for permeabilization of the cell membrane can also result in deactivation of the important enzyme. Second, other intracellular enzymes may compete for the reaction substrate giving rise to undesired byproducts and decreased yields. Third, intracellular degradation processes can limit the functional life of the biocatalyst. These problems may be eliminated if the enzyme is attached to the cell's exterior.

AopB-based display of alkaline phosphatase on the surface should lead to production of immobilized alkaline phosphatase, which can be used to dephosphorylate DNA fragments or for other application. The immobilized enzyme can be then easily removed by centrifugation or filtering.

EXAMPLES

The above disclosure generally describes the present invention. A more complete understanding can be obtained by reference to the following specific examples. These examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

Example 1

Experimental Protocols

Bacterial strains, plasmids and media: Bacterial strains and plasmids used in this study are listed in Table 1. *Escherichia coli* strains were grown at 37° C. in LB (Sambrook et al., 1989) supplemented with 50 μg/ml kanamycin, 100 μg/ml ampicillin and/or 10 μg/ml tetracycline if necessary. *Agrobacterium tumefaciens* strains were grown at 28° C. in MG/L, AB or IB (Cangelosi, G. A., Best, E. A., Martinetti, G., Nester, E. W., 1991. Genetic analysis of *Agrobacterium*. Methods Enzymol. 204, 384–397) supplemented with 100 μg/ml kanamycin and/or 5 μg/ml tetracycline if necessary. *Rhizobium meliloti* strains were grown in LB/MC or M9 medium (Finan, T. M., Kunkel, B., De Vos, G. F., Signer, E. R., 1986. Second symbiotic megaplasmid in *Rhizobium meliloti* carrying exopolysaccharide and thiamine synthesis genes. J. Bacteriol. 167: 66–72; Glazebrook J, Walker G C. 1991. Genetic techniques in *Rhizobium meliloti*. Methods Enzymol. 204: 398–418) supplemented with 10 μg/ml tetracycline when necessary. Plasmid DNA was introduced into *A. tumefaciens* strains of C58 or *R. meliloti* by triparental mating using MT616 as the helper strain.

TABLE 1

Bacterial strains and plasmids

| Strains | Relevant characteristic(s)[a] | Source or reference |
|---|---|---|
| *Escherichia coli* | | |
| DH5α | endA1 hsdR17 supE44 thi-1 recA1 gyrA96 relA1 Δ(argF-lacZYA)U169 φ80dlacZ ΔM15 | Bethesda Research Laboratories |
| MT607 | pro-82 thi-1 hsdR17 supE44 end44 endA1 recA56 | Finan et al., 1986 |
| MT616 | MT607(pKR600), mobilizer | Finan et al., 1986 |
| MT621 | pro-82 thi-1 hsdR17 supE44 end44 endA1 malF::TnphoA; Donor strain of TnphoA | Yarosh et al., 1989 |
| *Agrobacterium tumefaciens* | | |
| C58 | Wild type, nopaline-type pTiC58 plasmid | Laboratory collection |
| A136 | C58 cured of pTiC58, Rf[R], Nal[R] | Watson et al., 1975 |
| CGI1 | Derivative of C58 in which aopB is disrupted by the GFP-tagged mini-Tn5 transposon; Km[R], Gm[R] | This study |

TABLE 1-continued

Bacterial strains and plasmids

| | | |
|---|---|---|
| A6010 | A348 [A136(pTiA6NC)]; Pho⁻, Nal$^R$, Sm$^R$ | Cangelosi et al., 1991 |
| GMI9023 | C58 cured of pTiC58 and pAtC58, Sm$^R$, Rf$^R$ | Rosenberg and Huguet, 1984 |
| A348ΔvirB7 | A348 [A136(pTiA6NC)]; ΔvirB7 | Berger and Christie, 1994 |
| *Rhizobium meliloti* | | |
| RCR2011 | Same as SU47 wild type | Charles and Nester, 1993 |

| Plasmids | Relevant characteristic(s)$^a$ | Source or reference |
|---|---|---|
| pTZ19R | Cloning vector, ColE1 oriV bla, Amp$^R$ | US Biochemical |
| pSW172 | Broad-host-range IncP plasmid containing P$_{lac}$ and downstream polylinker sequence, Tc$^R$ | Chen and Winans, 1991 |
| pAG408 | Plasmid harboring the gfp-tagged mini-Tn5 transposon, Gm$^R$, Km$^R$, Amp$^R$ | Suarez et al., 1997 |
| pJYH2 | pTZ19R carrying a 9 kb SphI fragment containing aopB with the mini-Tn5 insertion at aopB, Km$^R$, Amp$^R$ | This study |
| pJYH5 | pSW172 carrying a 1.4 kb PCR product containing aopB, Tc$^R$ | This study |
| pJYH31 | pSW172 carrying a 0.9 kb PCR product containing aopB, Tc$^R$ | This study |
| pJYH5039 | pJYH5 containing TnphoA inserted at residue 39 of AopB, Km$^R$, Tc$^R$ | This study |
| pJYH5125 | pJYH5 containing TnphoA inserted at residue 125 of AopB, Km$^R$, Tc$^R$ | This study |
| pJYH5134 | pJYH5 containing TnphoA inserted at residue 134 of AopB, Km$^R$, Tc$^R$ | This study |
| pJYH5172 | pJYH5 containing TnphoA inserted at residue 172 of AopB, Km$^R$, Tc$^R$ | This study |
| pJYH5207 | pJYH5 containing TnphoA inserted at residue 207 of AopB, Km$^R$, Tc$^R$ | This study |
| pVJ::PhoA17 | pVK102 containing a virJ gene which is fused with phoA at residue 40 of VirJ, Km$^R$ | Pan et al., 1995 |
| pTC115A::PhoA | pTC115 containing a virA gene which is fused with phoA at the VirA cytoplasmic region, Km$^R$ | This study |
| pMAL-c2 | Cloning vector for expression and purification of maltose binding protein (MBP) fusion protein, Amp$^R$ | New England Biolabs |
| pJYH17 | pMAL-c2 containing a malE::aopB fusion encoding a MBP fused onto the full-length AopB at the EcoRI site of pMAL-c2, Amp$^R$ | This study |
| pJYH20 | A display vector derived from pSW172 and containing the aopB promoter and the aopB coding sequence 1–516 bp, Tc$^R$ | This study |
| pJYH21 | pJYH20 containing the gfp coding sequence at HindIII-PstI, Tc$^R$ | This study |
| pJYH23 | pJYH20 containing the phoA coding sequence at HindIII-PstI, Tc$^R$ | This study |

$^a$Amp, ampicillin; Gm, gentamycin; Km, kanamycin; Nal, nalidixic acid; Rf, rifampicin; Sm, streptomycin; Tc, tetracycline Berger B. R. Christie P. J. 1994. Genetic complementation analysis of the *Agrobacterium tumefaciens* virB operon; virB2 through virB11 are essential virulence genes, J. Bacteriol. 176; 3646–3660; Cangelosi, G. A., Best, E. A., Martinetti, G., Nester, E. W., 1991. Methods Enzymol. 204, 384–397; Charles, T. C., Nester, E. W., 1993. A chromosomally encoded two-component sensory transduction system is required for virulence of *Agrobacterium tumefaciens*, J. Bacteriol, 175: 6614–6625; Chen, C. Y., Winans, S. C., 1991. Controlled expression of the transcriptional activator gene virG in *Agrobacterium tumefaciens* by using the *Escherichia coli* lac promoter. J. Bacteriol. 173; 1139–114; Finan, T. M., Kunkel, B., De Vos, G. F., Signer, E. R., 1986. J. Bacteriol. 167: 66–72; Pan, S. Q., Jin, S., Boulton, M. I., Hawes, M., Gordon, M. P., Nester, E. W., 1995. An *Agrobacterium* virulence factor encoded by a Ti plasmid gene or a chromosomal gene is required for T-DNA transfer into plants. Mol. Microbiol. 17: 259–269; Rosenberg, C., Huguet, T., 1984. The pAtC58 plasmid is not essential for tumor induction. Mol. Gen. Genet. 196: 533–536; Suarez, A., Guttler, A., Stratz, M., Staendner, L. H., Timmis, K. N., Guzman, C. A., 1997. Green fluorescent protein-based reporter systems for genetic analysis of bacteria including monocopy applications. Gene 196: 69–74; Watson, B., Currier, T. C., Gordon, M. P., Chilton, M. D., Nester, E. W., 1975. Plasmid required for virulence of *Agrobacterium tumefaciens*. J. Bacteriol. 123: 255–264; Yarosh, O. K., Charles, T. C., Finan, T. M., 1989. Analysis of C4-dicarboxylate transport genes in *Rhizobium meliloti*. Mol. Microbiol. 3: 813–823.

DNA manipulations: DH5α was routinely used as the host for cloning experiments unless specified otherwise. High efficient competent cells were prepared as described previously (Inoue, H., Nojima, H., Okayama, H., 1990. High efficiency transformation of *Escherichia coli* with plasmids. Gene 96, 23–28). Plasmid DNA was introduced into *E. coli* by transformation according to the standard protocols (Sambrook et al., 1989). Broad-host-range plasmids were introduced into *A. tumefaciens* by triparental mating using MT616 as the helper strain (Ditta, G., Stanfield, S., Corbin, D., Helinski, D. R., 1980. Broad host range DNA cloning system for gram-negative bacteria: construction of a gene bank of *Rhizobium melioti*. Proc. Natl. Acad. Sci. USA 77: 7347–7351) or by electroporation (Cangelosi, G. A., Best, E. A., Martinetti, G., Nester, E. W., 1991. Methods Enzymol. 204, 384–397). Total DNA of *A. tumefaciens* was prepared according to Charles and Nester (Charles, T. C., Nester, E. W., 1993. J. Bacteriol. 175: 6614–6625).

Southern analysis: To generate the DNA probes, plasmid DNA was digested with appropriate restriction enzyme(s). The DNA fragments were isolated from agarose gels and purified by GENECLEAN II kit (Bio101). Probes were labeled randomly with fluorescein (Amersham). Total DNA of *A. tumefaciens* was digested and the fragments were separated on 1.0% agarose gels and transferred onto nylon membranes by using PosiBlot 30—30 Pressure Blotter (Stratagene). Hybridization, washing and detection were conducted according to the recommendations of the manufacturer (Amersham).

Cloning and sequencing of aopB: The total DNA was extracted from the mutant strain CGI1 which contains a mini-Tn5 insertion at the aopB gene. Southern analysis revealed that a 9 kb SphI DNA fragment contained the sequences flanking both sides of the insertion, as the transposon lacks a SphI site. The DNA fragment was extracted from the agarose gel and was purified by using GENECLEAN II kit (Bio101). The SphI DNA fragment was then cloned into pTZ19R at the SphI site. The resulting plasmid was designated pJYH2. Sequencing of pJYH2 was carried out using a mini-Tn5 specific primer and the M13 reverse and −40 universal primers. The resulting sequence data were then used to generate primers for further sequencing. DNA sequencing was carried out using the ABI PRISM 377 DNA sequencer.

In order to clone the full-length wild-type aopB gene, primers p54 (5'-GCAAATC<u>GCTAGC</u>TGTCACTCAGC-3'; SEQ ID NO:5) and p55 (5'-AGAACG<u>GCTAGC</u>GCACTGAAGCGG-3'; SEQ ID NO:6) were designed that can respectively reanneal to the upstream and downstream sequences of the aopB gene. Both primers had NheI sites (the underlined nucleotides) to facilitate subsequent cloning. The total DNA from *A. tumefaciens* strain C58 was used as the templated for PCR to amplify a 1.4 kb fragment. A 50 μl PCR reaction mixture contained 1× reaction buffer, 0.2 mM dNTPs, 20 pmol of each of the primers p54 and p55, and 2.5 units of Taq DNA polymerase (Promega). The PCR reaction mixture was denatured at 95° C. for 1 mm. Then a total of 30 cycles were run as follows: denaturation at 95° C. for 30 s, annealing at 50° C. for 30 s, and extension at 72° C. for 1.5 mm, followed by 1 cycle of extension at 72° C. for 10 mm. The PCR product was digested with NheI and ligated into pSW172 that had been digested with XbaI. The resulting plasmid pJYH5 was sequenced in both directions independently to obtain unambiguous sequence data. Homologous sequences were searched in the databases with the BLAST program. Putative signal peptide was identified by the SMART program.

Purification of MBP-AopB fusion protein and generation of antibody to AopB: DH5α(pJYH17) harboring a MBP-AopB in-frame fusion construct was grown overnight in LB medium in the presence of 100 μg/ml of ampicillin at 37° C. The cell culture was diluted 100 times with fresh rich medium and cultured at 37° C. to $OD_{600} \approx 0.5$. Induction of the MBP-AopB fusion protein was conducted by addition of IPTG to the final concentration of 0.3 mM and growing the cells at 37° C. for another 2–3 h. Purification of MBP-AopB was conducted as described by Pan et al., 1995. Mol. Microbiol. 17: 259–269. The purified protein was injected into rabbits to generate the primary antibody.

Determination of AopB protein topology by TnphoA mutagenesis: The plasmid pJYH5 containing the wild-type aopB gene was transformed into MT621 which contains the TnphoA transposon. Triparental mating was then conducted by mixing MT621(pJYH5), A6010 and MT616 cells together and incubating overnight at 28° C. on MG/L agar plates. The mixture was scraped with a sterile wooden stick and resuspended in IB liquid medium. The cell suspensions were spread onto IB plates containing kanamycin, tetracycline and the chromogenic substrate 5-bromo-4-chloro-3-indolyl phosphate (X-phos, 20 μg/ml) and then incubated at 28° C. for 3 days. The blue colonies were transferred to fresh MG/L plates containing 100 μg/ml kanamycin and 2 μg/ml tetracycline for purification. The plasmids containing TnphoA insertions were introduced into MT607 by triparental mating, using MT616 as helper strain. SmaI and ClaI were used to map the TnphoA insertion positions. Sequencing was conducted by using a phoA specific primer to determine the precise insertion positions. To measure the alkaline phosphatase activities, *A. tumefaciens* cells were cultured overnight at 28° C. in MG/L and then transferred to AB, IB or IB with acetosyringone (AS) (100 μM) at $OD_{600}=0.3$. The alkaline phosphatase activities of the PhoA fusions were determined by measuring the rates of hydrolysis of the substrate p-nitrophenyl phosphate (Brickman, E., Beckwith, J., 1975. Analysis of the regulation of *Escherichia coli* alkaline phosphatase synthesis using deletions and phi80 transducing phages. J. Mol. Biol. 96: 307–316). The specific units of alkaline phosphatase activity are calculated using the following formula: $[(A_{420}-1.75 \times A_{550}) \times 10^3]/[t(min) \times A_{600}]$.

Measurements of aopB gene expression: The aopB gene expression was measured by using both aopB-gfp and aopB-phoA fusions. To use the aopB-gfp fusion, the CGI1 cells were grown in different media. The relative fluorescence intensities ($I_r$) were measured as described previously (Tang, X., Lu, B. F., Pan, S. Q. 1999. A bifunctional transposon mini-Tn5gfp-km which can be used to select for promoter fusions and report gene expression levels in *Agrobacterium tumefaciens*. FEMS Microbiology Letters 179: 37–42). The C58 cells were used as the negative control. The excitation wavelength was 395 nm; the emission wavelength was 510 nm; and the wavelength slit was 5. When the aopB-phoA fusions were used, the alkaline phosphatase activities of the bacterial cells containing the aopB-phoA fusions were measured as described earlier.

Subcellular fractionation: Subcellular fractionation of *A. tumefaciens* was conducted as described previously (De Maagd, R. A., Lugtenberg, B., 1986. Fractionation of *Rhizobium leguminosarum* cells into outer membrane, cytoplasmic membrane, periplasmic, and cytoplasmic components. J. Bacteriol. 167: 1083–1085) with some modifications. Briefly, *A. tumefaciens* strains C58 and CGI1 were cultured in MG/L medium overnight at 28° C. and the cells were collected by centrifugation at 3200×g for 5 min. The cells were then washed once with water and transferred into fresh IB liquid medium at $OD_{600}$ =0.3. The cells was induced at 28° C. for 18–20 h and collected as above. The cell pellet was washed three times with 50 mM Tris-HCl (pH 8.0) by centrifugation at room temperature. One portion of the cell pellet (approximately $2\times10^{10}$ cells based on $OD_{600}$ measurement) was used to isolate the periplasmic fraction as follows. The cell pellet was resuspended in 5 ml of 50 mM Tris-HCl (pH 8.0), 20% sucrose, 2 mM EDTA and 0.2 mg/ml lysozyme. The cell suspension was incubated at room temperature for 30 min and centrifuged at 3000×g for 15 min at 4° C. The resulting supernatant was centrifuged at 20,000×g for 15 min and the supernatant was saved as the periplasmic fraction. Another portion of the cell pellet ($1\times10^{11}$ cells) was used to prepare other subcellular fractions as follows. The cell pellet was resuspended in 5 ml of 50 mM Tris-HCl (pH 8.5), 20% sucrose, 0.2 mM DTT, 0.2 mg/ml DNase I and 0.2 mg/ml RNase A. The cell suspension was passed through a French Press mini-cell five times at 20,000 psi and incubated on ice for 30 min. The cell lysate was diluted with 2 volumes of 50 mM Tris-HCl (pH 8.5) and centrifuged for 2 h at 262,000×g in a Beckman SW80Ti rotor. The supernatant was saved as the cytosolic fraction and the pellet was suspended in 20% sucrose-5 mM EDTA-0.2 mM DTT by sonication and one small portion of the suspension was saved as the total membrane fraction. The remaining suspension was layered on top of the following density gradient: 2 ml of 60% sucrose (wt/wt), 4 ml of 45% sucrose (wt/wt) and 5 ml of 30% sucrose (wt/wt) in 5 mM EDTA (pH 7.5). The gradient was centrifuged for 18 h at 58,000×g in a Beckman SW41Ti rotor. The upper band was collected and saved as the inner membrane fraction and the lower band was saved as the outer membrane fraction. Proteins in the periplasmic, cytosolic, inner membrane and outer membrane fractions were precipitated by addition of 3 volumes of acetone. Each fraction was dissolved in the Laemmli sample buffer.

Whole cell ELISA for AopB: The cells of *A. tumefaciens* strain A6010 were induced in the IB medium in the presence of 100 μM of acetosyngone (AS) and washed twice with PBS (pH 7.4) by centrifugation at 10,000 g for 5 min. The cell concentration was determined by measuring the optical density at 600 nm and adjusted to $4\times10^8$ cells/ml. Then 50 μl of cell suspensions were transferred to the wells of IMMUNLON 2HB microtiter plates. The cells were fixed by addition of 50 μl of 8% paraformaldehyde and incubation at room temperature for 45 min. They were then washed twice with PBS (pH 7.4) and blocked with 120 μl of 2% bovine serum albumin in PBS for 45 min. After three washes with PBS, the cells were incubated for 45 min with the AopB antibody, VirJ antibody (Pan et al., 1995. Mol. Microbiol. 17: 259–269) or GFP monoclonal antibody (Clontech) each diluted (1:500) in PBST/BSA (PBS, 0.02% Tween 20, 0.2% BSA). The cells were washed three times with PBST (PBS, 0.05% Tween 20) for 10 min each time. Then 50 μl of HRP conjugated secondary antibodies (diluted at 1:2000) were added and incubated for 45 min. The cells were washed for 3 times with PBST before 200 μl of TMB-ELISA (GIBCO) were added to each well and incubated in dark for 15 min. The reaction was stopped by addition of 50 μl of 1 N $H_2SO_4$. Absorbance at 450 nm were measured using an ELISA reader.

Western analysis: Protein samples were denatured in the Laemmli sample buffer by boiling for 5 min and loaded on SDS/12% PAGE glycine gels. Proteins were transferred electrophoretically onto PVDF membranes (BIO-RAD). Blocking, washing and detection were conducted with the enhanced chemiluminescence reagents according to the recommendations of the manufacturer (Pierce).

Antisera: Rabbit anti-AopB polyclonal antibody was raised as described earlier. Mouse anti-alkaline phosphatase (AP) monoclonal antibody was purchased from Chemicon International. Mouse anti-GFP monoclonal antibody was purchased from Clontech. Rabbit anti-ChvE antibody was a gift from C. W. Jones. r-Phycoerythrin (r-PE) conjugated goat anti-mouse IgG was from Molecular Probes. HRP conjugated goat anti-rabbit and goat anti-mouse IgG were from Pierce.

Whole cell ELISA experiments for displayed proteins: *A. tumefaciens* cells were grown in different liquid culture media; the cell suspensions were measured for $OD_{600}$; and the cell concentrations were adjusted to $4\times10^8$ cells/ml. Then 50 μl of each cell suspension was transferred to each well of Immunlon 2HB microtiter plates (Dynex). The cells in each-well were fixed by addition of 50 μl of 8% paraformaldehyde and incubation at room temperature for 1 hour. They were then washed twice with PBS (pH 7.4) and blocked with 150 μl of PBS containing 2% BSA (PBS/BSA) for 1 h. After three washes with PBS, the cells were incubated with the first antibody diluted (1:500) in PBS/BSA containing 0.02% Tween-20 for 1 hour. The cells were washed three times with PBS with 0.05% Tween 20 (PBST) using a washing bottle with an incubation of 10 min between washes. Then 50 μl of HRP conjugated goat anti-rabbit or goat anti-mouse IgG diluted at 1:2000 was added and incubated for 1 hour. The cells were washed for 5 times with PBST before 200 μl of TMB-ELISA (GIBCO) was added to the wells and incubated in dark for 15 min. The reaction was stopped by addition of 50 μl of 1 N $H_2SO_4$. Absorbances at 450 nm were measured using an ELISA reader.

Flow cytometry: *A. tumefaciens* strains C58(pJYH5), C58(pJYH5039), C58(pJYH5125), C58(pJYH5134), C58 (pJYH5172) and C58(pJYH5207) were cultured as described above. For each strain, $4\times10^8$ cells were collected by centrifugation at 10,000×g for 1 min. The cell pellets were washed with PBS twice and incubated in 1.5 ml of PBS/BSA for 30 min. The monoclonal mouse anti-AP antibody was diluted in PBS/BSA (1:1000) and then added to the suspensions. The suspensions were incubated at room temperature for 45 min with gentle agitation. After washing three times with PBST, the cells were resuspended in 1.0 ml of r-phycoerythrin conjugated goat anti-mouse IgG (Molecular Probes) diluted (1:100) in PBS/BSA and incubated in dark for 45 min with agitation. After washing once with PBST, the cells were fixed by addition of 1 ml of 2% paraformaldehyde and incubation at room temperature for 30 min. Then four more times of washing were conducted as above; the cells were resuspended in 500 μl of PBS and examined under a FACS flow cytometer. The fluorescence of 10,000 cells was recorded.

Confocal microscopy: Samples of 15 μl of the cell suspensions treated for flow cytometry described above were dropped onto glass slides; one drop of mounting medium (Vector) was applied to each sample to prevent rapid quenching of the fluorescence and a coverslip was placed on top of the emulsion. The cells were examined under confocol microscope with an excitation of 543 nm and emission of 570 nm.

Protease accessibility assays: *A. tumefaciens* cells were grown in different liquid culture media. The cells were digested by trypsin as described previously (Burnett M S, Wang N, Hofmann M, Kitto G B. 2001. Vaccine. 19: 735–742) with some modifications. Briefly, 1 ml of cell suspensions of $OD_{600}$=1 was-collected by centrifugation at 10,000×g for 1 min and washed once in 1 ml of 25 mM HEPES buffer (pH 8.0) containing 10 MM MgCl$_2$. The cell pellet was resuspended in 50 μl of the same buffer and incubated on ice-for 30 min. Trypsin was added to the cell suspension at the final concentration of 0.1 mg/ml; the mixture was incubated at 37° C. for 5 min. The reaction was terminated by addition of 55 μl of 2× Laemmli sample buffer. The samples were boiled for 10 min and then 10 μl of the samples were loaded onto SDS/10% polyacrymide/Tris-glycine gels. Proteins were transferred electrophoretically onto PVDF membranes (Bio-Rad). Blocking, washing and detection were conducted with the enhanced chemiluminescence reagents according to the recommendations of the manufacturer (Pierce). AopB-PhoA and AopB-GFP proteins were visualized by using the anti-AopB antibody. The ChvE protein was visualized as the control by using the anti-ChvE antibody.

Measurement of alkaline phosphatase activity for bacterial cells harboring pJYH23: *A. tumefaciens* cells were cultured overnight in MG/L at 28° C.; the cells were harvested and then resuspended in MG/L, AB, or IB at OD$_{600}$=0.3; the cells were grown at 28° C. for 18 hr. *E. coli* cells were grown in LB at 28° C. overnight; *R. meliloti* cells were grown in LB/MC at 28° C. overnight. Bacterial cells equivalent to 1 ml of OD$_{600}$=1 for each treatment were collected, washed and treated with or without 0.1 mg/ml trypsin as described above for the protease accessibility assays. The bacterial cells were then washed twice with 1 M Tris-HCl (pH 8.0) and resuspended in 1 ml of the same buffer. Then 100 μl of each cell suspension was taken and diluted to 1 ml with 1 M Tris-HCl (pH 8.0). The cell suspensions were used to measure the alkaline phosphatase (AP) activities of the bacterial cells (containing pJYH23) expressing the AopB$_{172}$-PhoA protein by determining the rates of hydrolysis of the substrate p-nitrophenyl phosphate as described previously (Brickman and Beckwith, 1975). The specific units of alkaline phosphatase activity are calculated using the following formula: $[(A_{420-1.75}\times A_{550})\times 10^3]/[t(min)\times A_{600}]$. The decrease of AP activity due to trypsin treatment was expressed as percentage of the units of AP activity eliminated by the trypsin treatment.

Example 2

Identification and Characterization of aopB and Identification of aopB-Related Genes

*A. tumefaciens* C58 was mutagenized with a mini-Tn5 transposon containing a promoter-less gene encoding a GFP variant, which produces bright green fluorescence under UV light (Li, L., Li, Y., Lim, T. M., Pan, S. Q., 1999. GFP-aided confocal laser scanning microscopy can monitor *Agrobacterium tumefaciens* cell morphology and gene expression associated with infection. FEMS Microbiol. Lett. 179: 141–146). The mini-Tn5 transposon was carried on a plasmid pAG408 (Suarez, A., Guttler, A., Stratz, M., Staendner, L. H., Timmis, K. N., Guzman, C. A., 1997. Green fluorescent protein-based reporter systems for genetic analysis of bacteria including monocopy applications. Gene 196: 69–74). One of the mutants, CGI1, contained the transposon insertion at a gene that was differentially induced by low pH on a minimal medium; CGI1 gave bright fluorescence on IB (a minimal medium of pH 5.5) plates but not on AB (a minimal medium of pH 7.0) plates. No difference in growth rate was observed between CGI1 and the parent strain C58 under all the culture conditions (MG/L, AB, IB) tested. The leaves of Kalanchoe plants were inoculated with this mutant strain CGI1 and the parent strain C58. At the concentration of 5×10$^9$ cells/ml, there was no apparent difference in tumor formation between mutant CGI1 and C58. At a lower concentration of 5×10$^7$, however, the mutant CG1 caused much less and smaller tumors on plants than C58. In order to isolate the mini-Tn5 containing DNA fragments, Southern analysis was conducted to estimate their sizes. A 9 kb SphI DNA fragment containing the mini-Tn5 and the sequences flanking the mini-Tn5 insertion was cloned into pTZ19R to generate pJYH2. Sequence analysis of pJYH2 revealed that the transposon was inserted at a gene that is homologous to a gene encoding a *Rhizobium* outer membrane protein (ropB) (Roest, H. P., Mulders, I. H., Wijffelman, C. A., Lugtenberg B. J., 1995. Isolation of ropB, a gene encoding a 22-kDa *Rhizobium leguminosarum* outer membrane protein. Mol. Plant-Microbe Interact. 8: 576–583). This *A. tumefaciens* gene was designated as aopB (*Agrobacterium* outer membrane protein).

Figure 1B:
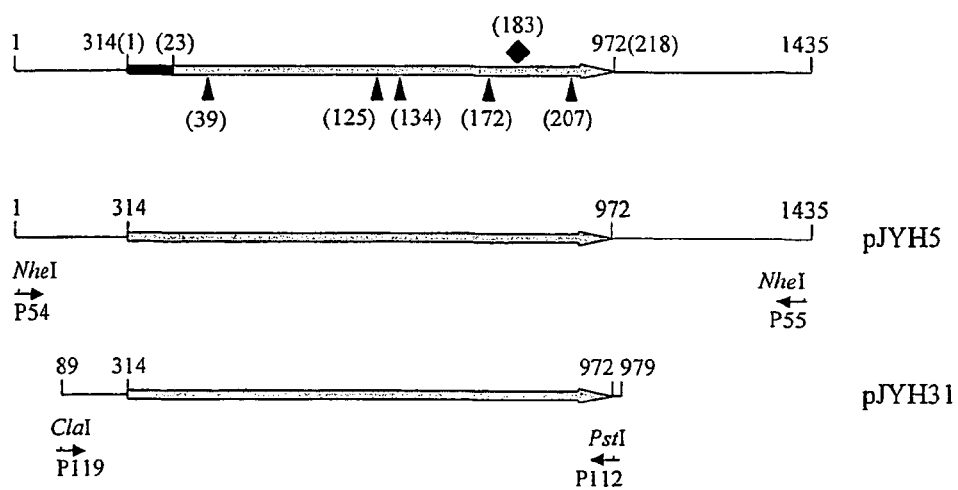
FIG. 1 shows the sequence of the aopB locus and the related constructs.

In order to determine the complete sequence of the gene, the DNA fragment was amplified from C58 by PCR. A fragment of 1.4 kb was obtained that contained both the upstream and downstream sequences of aopB. The resulting fragment was cloned into pSW172 to generate plasmid pJYH5. When pJYH5 was introduced into the mutant CGI1, it could fully restore the ability of the mutant to cause tumors, suggesting that pJYH5 carried a full-length aopB gene. Since the 1.4 kb PCR fragment contained about 500 bp sequence downstream of the aopB gene, it is possible that this short fragment might contain a small ORF that can complement the transposon mutation. To exclude the possibility that the polar effect of the transposon mutation on a gene downstream of aopB might have contributed to the attenuated virulence in CGI1, a PCR fragment was amplified from C58 using p119 (5'-AAATCGATCTATTGCTGGT-TAGGC-3'; SEQ ID NO:7) and p112 (5'-CGACTGCA-GAAGGATCAGAACTTG-3'; SEQ ID NO:8), which contained ClaI and PstI sites, respectively. This generated a smaller DNA fragment, which was then cloned into pSW172 to obtain pJYH31. This fragment carried the sequence from 89 to 979 bp of the 1.4 kp fragment (FIG. 1B) but no ORE downstream of aopB. pJYH31 was introduced into CGI1 by triparental mating. Virulence assays on plant leaves showed that CGI1 (pJYH31) also fully restored the tumorigenesis ability. This unequivocally demonstrated that the attenuated virulence in CGI1 was caused by the mutation at aopB. Sequence analysis indicated that the aopB locus carried an open reading frame (ORE) which encodes a putative protein of 218 amino acids with a molecular weight of 22.8 kDa (FIG. 1A). This putative protein had 60% similarity to RopB (FIG. 2).

To determine the location of the aopB gene, the genomic DNA from A6 and the C58 derivatives A136 and GMI9023 was probed with a DNA fragment containing aopB. Southern analysis showed that each of GMI9023, A136, A6, C58 and CGI1 contained a single SphI fragment containing the aopB gene (FIG. 3). This suggests that the aopB gene is present as a single copy on the chromosome of these strains, since GMI9023 contained neither the Ti plasmid nor the cryptic plasmid. CGI1 contained a 9 kb fragment while GMI9023, A136 and C58 contained a 5.8 kb fragment, because CGI1 had the mini-Tn5 transposon insertion at aopB. Detection of a larger SphI fragment in A6 suggests that it is likely that the octopine strain might also contain an aopB gene but the sequence might be different from the nopaline strains. No hybridization signal was detected in the *Rhizobium* strain, as the homology between the aopB gene and ropB gene at the DNA sequence level is only 66.5%.

The AopB protein has 60% similarity to RopB at the amino acid sequence level (FIG. 2). AopB also shares 42–47% similarity with the immunogenic outer membrane proteins in *Brucella* species, 46% similarity with Pap31 of *Bartonella hensela* infected with a bacteriophage, 47% similarity with *Pasteurella haemolytica* outer membrane protein PomA, 39% similarity with PPE of *Mycobacterium tuberculosis,* 43% similarity with *Haemophilus ducreyi* major outer membrane protein, and 40% similarity with the outer membrane porin of *Vibrio cholerae.* The AopB protein also shares homology with part of the porin protein F (OprF) of *Pseudomonas* species at the C-terminal half.

Example 3

Localization of AopB to the Cell Surface

To determine where the AopB protein was localized in the bacterial cells, the subcellular localization of AopB was determined by mutagenizing pJYH5 with TnphoA transposon. Seventeen blue colonies were obtained out of 3000 transconjugants. The plasmids from these blue colonies were introduced into MT607 using MT616 as the helper strain. Restriction map analysis of these plasmids revealed that 14 of them contained the TnphoA insertions within the AopB open reading frame of pJYH5. Both restriction mapping and DNA sequencing revealed that they contained the phoA insertions at 5 different positions, which mapped throughout the entire AopB protein (FIG. 1B). The AopB residues 134 and 207 were the TnphoA transposition hot spots, as 5 and 4 insertions mapped to these sites, respectively (FIG. 1B). It is also possible that these were the progeny of the same transposition events. Enzymatic assays indicated that the transposon insertions at the 5 different sites generated a comparable level of alkaline phosphatase (PhoA) activity (Table 2). The PhoA activities generated from the aopB-phoA fusions were higher than that from the virJ-phoA fusion (Table 2); and VirJ is known to be present in the periplasm (Pan et al., 1995. Mol. Microbiol. 17: 259–269). These results suggest that the entire AopB protein was localized in the periplasm or outer membrane.

The subcellular fractionation experiments were then conducted to determine the protein location, based on a previously described procedure (De Maagd, R. A., Lugtenberg, B., 1986. J. Bacteriol. 167: 1083–1085; Pan et al, 1995. Mol. Microbiol. 17: 259–269). As shown in FIG. 4, the AopB protein appeared to be present exclusively in the outer membrane fraction, as no AopB was detected in the periplasmic, cytosolic and inner membrane fractions. Interestingly, an in-frame AopB-GFP fusion protein detected in the transposon mutant CGI1 was also present in the outer membrane (lane 12). However, this fusion protein appeared to be unstable because much less amount of AopB-GFP was detected in the outer membrane as compared to the total cell lysate (lanes 2 and 12) and the AopB-GFP fusion protein was undetectable in other fractions (lanes 4, 6, 8 and 10). On the other hand, the native AopB protein appeared to be very stable as the amount of AopB detected in the cell lysate was similar to that in the outer membrane (lanes 1 and 11). Sequencing analysis indicated that the TnphoA transposon was inserted at amino acid position 183. These results suggest that the N-terminus of 183 amino acids was capable of exporting the fusion protein to the outer membrane. The fusion protein might be unstably associated with the outer membrane or prone to degradation during subcellular fractionation, as much less amount of the fusion protein could be detected in the outer membrane fraction (lane 12).

Whole cell ELISA was conducted to confirm the AopB location by determining whether AopB is exposed on the cell surface of the outer membrane and can interact directly with the AopB antibody. As shown in FIG. 5, induced cells of *Agrobacterium* strain A6010 (containing the wild-type aopB) could react with the AopB antibody but not with VirJ or GFP antibody. This confirmed the subcellular fractionation evidence that AopB is an outer membrane protein. Since VirJ is known to be localized predominantly in the periplasmic fraction (Pan et al., 1995. Mol. Microbiol. 17: 259–269), thus the possibility was eliminated that a protein localized in the periplasm could interact with the antibody during the whole cell ELISA experiment. The hydropathy profile of the putative AopB protein did not reveal any large hydrophobic region. Taken together, it can be concluded that AopB is exposed on the cell surface of the outer membrane.

TABLE 2

Alkaline phosphatase (AP) activities of the phoA fusions[a]

| Strains | Fusion type | Fusion position | AP activity |
| --- | --- | --- | --- |
| A6010[b] | — | — | 0 |
| A6010(pTC115A::phoA)[b] | VirA-PhoA | Cytoplasmic domain | 0 |
| A6010(pVJ::phoA17)[b] | VirJ-PhoA | 40 | 75 ± 9 |
| A6010(pJYH5) | — | — | 0 |
| A6010(pJYH5039) | AopB-PhoA | 39 | 854 ± 26 |
| A6010(pJYH5125) | AopB-PhoA | 125 | 763 ± 52 |
| A6010(pJYH5134) | AopB-PhoA | 134 | 668 ± 12 |
| A6010(pJYH5172) | AopB-PhoA | 172 | 1042 ± 48 |
| A6010(pJYH5207) | AopB-PhoA | 207 | 1031 ± 58 |

[a]The alkaline phosphatase (AP) activities were measured with the *Agrobacterium tumefaciens* cells (harboring the plasmids containing the virJ-phoA fusion, virA-phoA fusion or aopB-phoA fusions) grown in induction medium as described in Example 1. A6010(pVJ::PhoA17) and A6010 (pTC115A::PhoA) were used as the positive and the negative control, respectively, because the VirJ-PhoA is periplasmic and the VirA-PhoA fusion is located in the cytoplasm.
[b]*Agrobacterium tumefaciens* cells A6010, A6010(pTC115A::phoA) and A6010(pVJ::phoA17) were induced in the presence of 100 μM acetosyringone (AS) since the induction of virJ and virA gene requires the phenolic compounds.

Example 4

Induction of the aopB Gene by Acidic pH

To confirm that the aopB gene is inducible by acidic pH, the relative fluorescence intensities of the mutant strain CGI1 (containing the aopB-gfp fusion) cultured in different media were compared. As shown in Table 3, the aopB-gfp expression increased by 7 fold when the cells were cultured in IB as compared with AB medium. However, the presence of AS in IB did not affect the aopB-gfp expression. In addition, the aopB gene expression was measured by using the aopB-phoA fusions. The aopB-phoA expression increased 4–5 fold when the cells were cultured in IB as compared with AB medium. Again, AS did not affect aopB-phoA expression. These data strongly suggested that aopB gene could be induced by acidic pH but not by AS.

TABLE 3

Induction of the aopB gene expression

| Strains | Fusion type | Fusion position | Medium | $I_r{}^a$ or Units of AP activity[b] | Induction on fold[c] |
|---|---|---|---|---|---|
| CGI1 | AopB-GFP | 183 | AB | 54 ± 6 | N/A |
| | | | IB | 381 ± 16 | 7.06 |
| | | | IB + AS | 384 ± 19 | 7.11 |
| A6010(pJYH5039) | AopB-PhoA | 39 | AB | 184 ± 8 | N/A |
| | | | IB | 925 ± 61 | 5.03 |
| | | | IB + AS | 901 ± 70 | 4.90 |
| A6010(pJYH5172) | AopB-phoA | 172 | AB | 338 ± 25 | N/A |
| | | | IB | 1409 ± 126 | 4.17 |
| | | | IB + AS | 1431 ± 86 | 4.23 |
| A6010(pVJ::phoA17) | VirJ-PhoA | 40 | IB + AS | 82 ± 6 | N/A |
| A6010(pTC115A::phoA) | VirA-PhoA | Cytoplasmic domain | IB + AS | 0 | N/A |

[a]The relative fluorescence intensities ($I_r$) of Agrobacterium strain CGI1 (containing the aopB-gfp fusion) grown in different media were measured as described in Example 1.
[b]The alkaline phosphatase (AP) activities were measured for Agrobacterium tumefaciens cells (harboring the plasmid containing the virJ-phoA fusion, virA-phoA fusion or aopB-phoA fusions) grown in different media as described in Example 1. During the AP assays, A6010(pVJ::PhoA17) and A6010(pTC115A::PhoA) were used as the positive and the negative control, respectively, because the VirJ-PhoA is periplasmic and the VirA-PhoA fusion is located in the cytoplasm.
[c]The induction fold was calculated by using the gene expression level in the AB medium as the control.

Example 5

Surface Display of GFP and-PhoA by AopB

This example demonstrates that when the N-terminal domain of AopB was fused onto GFP or PhoA, the AopB-GFP and AopB-PhoA fusion proteins were found to be present on the bacterial cell surface. Both GFP and PhoA in the fusions were exposed on the surface; they were available to interact with their corresponding antibodies. The primary antibodies to GFP and PhoA can directly and specifically interact with the fusion proteins present on the surface on the intact bacterial cells. The complexes of the primary antibodies with GFP or PhoA were stable. They can be detected by colorimetric assays once they are allowed to form complexes with enzyme-conjugated secondary antibodies. The relatively large protein alkaline phosphatase (molecular weight of greater than 80 kDa in its dimeric form) was expressed on the surface.

Whole cell ELISA experiments were conducted to test the surface accessibility of the AopB-GFP fusion protein to mouse GFP antibody. It was of interest to test whether the GFP antibody could bind to the AopB-GFP protein produced by the CGI1 cells which contained the aopB-gfp fusion; CG19 was used as the negative control because it could produce cytoplasmic GFP protein at a high level. As shown in FIG. 6, the AopB-GFP protein was indeed located on the bacterial cell surface, because the AopB-GFP protein of the CGI1 whole cells could bind to the GFP antibody (Panel A). In contrast, the cytoplasmic GFP produced by CG19 was inaccessible to the GFP antibody as expected.

It was of interest to know if AopB could display the alkaline phosphatase (PhoA) protein, which could not be readily displayed by other systems. The previously constructed plasmids pJYH5039, pJYH5125, pJYH5134, pJYH5172 and pJYH5207 contain the aopB-phoA fusions with PhoA fused onto AopB at the amino acid positions 39, 125, 134, 172 and 207, respectively. These plasmids were introduced into C58 and the surface accessibility of the AopB-PhoA fusion proteins to the PhoA antibody was then tested. The whole cell ELISA (FIG. 6, panel B), flow cytometry analysis (FIG. 7) and confocal microscopy all consistently demonstrated that AopB could display the PhoA on the cell surface. The efficiency of surface display was the highest when the PhoA was fused onto the amino acid position 172 of AopB; the efficiency was the lowest when the fusion occurred the position 39 (FIG. 6, Panel B; FIG. 7). The data indicated that AopB could be used to directly display the PhoA protein without addition of any reducing reagent in the growth medium. The display of PhoA could be monitored by whole cell ELISA, flow cytometry and confocal microscopy.

To further confirm the surface display of GFP and PhoA by AopB, the protease accessibility assays were conducted, as the passenger proteins displayed on the cell surface could be degraded by externally added proteases (Earhart C. F. 2000. Use of an Lpp-OmpA fusion vehicle for bacterial surface display. Methods Enzymol. 326: 506–516). Trypsin digestion was used to assess the surface localization of AopB-GFP and AopB-PhoA fusion proteins in CGI1 or C58 containing pJYH5039, pJYH5125, pJYH5134, pJYH5172 or pJYH5207. The digestion was conducted in the presence of 10 mM $MgCl_2$ to prevent protease from penetrating into the periplasmic space (Tommassen J, Lugtenberg B. 1984. Amino terminus of outer membrane PhoE protein: localization by use of a bla-phoE hybrid gene. J. Bacteriol. 157: 327–329). The ChvE protein was used as the negative marker, as ChvE is known as a periplasmic protein.

As shown in FIG. 8, the AopB-GFP fusions positioned at amino acid 183 of AopB ($AopB_{183}$-GFP) and the AopB-PhoA fusions positioned at amino acid 125, 134, 172 and 207 of AopB ($AopB_{125}$-PhoA, $AopB_{134}$-PhoA, $AopB_{172}$-PhoA, $AopB_{207}$-PhoA) all decreased significantly when trypsin was added to the whole cells producing the fusion proteins. In contrast, the periplasmic protein ChvE was not degraded by externally added trypsin in all the strains tested.

Consistent with whole cell ELISA, flow cytometry and confocal microscopy, all the results indicated that the N-terminal amino acid positions 125, 134, 172, 183 and 207 of AopB were the permissive sites to direct foreign proteins onto the bacterial cell surface. However, very little digestion of the $AopB_{39}$-PhoA protein was detected, suggesting that the amino acid position 39 could not generate a complete display of PhoA. The whole cell ELISA experiments also indicated that the amino acid position 39 was not an efficient site for the display (FIG. 6). It is possible that the AopB N-terminal domain of only 39 amino acids was inefficient to expose much of the PhoA on the cell surface. Nevertheless, the amino acid position 172 was the best site for displaying PhoA.

One major consideration in cell surface display is the outer membrane integrity of displaying cells, since many surface based assays would be unreliable if the outer membrane is structurally compromised. The protease accessibility experiments showed that the AopB-GFP and AopB-PhoA fusion proteins could be digested by externally added trypsin, while the periplasmic protein ChvE was not significantly digested (FIG. 8). This suggested that the integrity of outer membrane was largely intact for the displaying bacterial cells of the AopB-based system.

Example 6

Construction of a Vector for Surface Display

In order to facilitate convenient display of different proteins, a plasmid vector was constructed using the aopB as the carrier (FIG. 9). To do this, it was first determined if the aopB sequence encoding the N-terminal protein domain alone could facilitate the display. The C-terminal domain of AopB amino acids 173–218) and the downstream sequence were deleted. The aopB promoter and the sequence encoding the AopB N-terminal region (amino acids 1–172) were retained. The amino acid position 172 of AopB was chosen as the fusion site, as this site was the most efficient in displaying the PhoA protein. A pair of primers, p118 (5'-CCGGT ACCGGATCCTGCAGCTAGCAAGCTTCA ACACCGGCACCAACCG TGTAAC-3';SEQ ID NO:9) and p119 (5'-AAATCGATCTATTGCTGGTTAGGC-3'; SEQ ID NO:7), were used to amplify a fragment of 0.7 kb using the C58 genomic DNA as the template. The resulting PCR product contained the aopB promoter (223 bp upstream of start codon) and the aopB coding region ranging from 1 to 513 bp. This fragment was digested by ClaI and KpnI and subsequently ligated with pSW172 cut by the same enzymes. The resulting plasmid pJYH20 contained a multiple cloning site to facilitate the cloning of foreign genes. (FIG. 9).

To test whether the vector plasmid pJYH20 could be used to display proteins such as GFP and PhoA, a 0.7-kb fragment containing the gfp coding sequence was cloned by PCR using primers GFPuvFh3 (5'-GGG AAGCTTGGAGTAAAGGAGAAGAAC-3'; SEQ ID NO:10) and GFPuvRp1 (5'-AA CTGCAGTCATTATTTGTAGAGC-3'; SEQ ID NO:11) and using pGFP$_{uv}$ (Clontech) as the template. HindIII and PstI (underlined) sites were introduced to facilitate subsequent cloning. The start codon ATG was changed to TGG (bolded) to avoid any translational initiation at this site. The resulting fragment was digested by HindIII and PstI and cloned into HindIII-PstI digested pJYH20. The resulting plasmid pJYH21 contained an in-frame-fusion of aopB-gfp. A 1.3-kb phoA fragment was also amplified, which was then cloned into pJYH20 to generate pJYH23. pJYH5039 was used as the template; the primers were PhoAfH3 (5'-GGGAAGCT-TCTGACTCTTATACACAA GTAGCG-3'; SEQ ID NO:12) and PhoAreP1 (5'-GGCTGCAGTTATTTCAGCCCCA GAGCGGC-3'; SEQ ID NO:13), which contained HindIII and PstI (underlined) sites, respectively. pJYH23 contained an in-frame-fusion of aopB-phoA, in which the phoA gene lacked the sequence coding for the N-terminal signal peptide. Plasmid pJYH21 and pJYH23 were then introduced into C58 by triparental mating.

Whole cell ELISA and trypsin digestion experiments were then conducted as described earlier to demonstrate whether GFP and PhoA were expressed on the cell surface in the strains C58(pJYH21) and C58(pJYH23), respectively. As shown in FIG. 6, the display efficiency of both GFP and PhoA by the plasmid vector pJYH20 was similar to the original aopB-gfp and aopB-phoA fusions, as C58(pJYH21) and C58(pJYH23) generated a similar display as CGI1 and C58(pJYH5172), respectively. In the trypsin digestion experiments, the AopB-GFP produced by C58(pJYH21) and AopB-PhoA produced by C58(pJYH23) were also accessible to the trypsin digestion. This proved directly that the N-terminal but not the C-terminal domain of AopB was required for translocation of the passenger fusion proteins onto the cell surface.

This also demonstrated that the display vector plasmid pJYH20 could be used to efficiently display proteins on the bacterial cell surface. The unique restriction sites HindIII, PstI, BamHI, KpnI and SacI located downstream of aopB could simplify the cloning of foreign genes encoding passenger proteins.

Example 7

Effects of Conditions on the Expression and Display of Fusion Proteins

In order to learn more about the characteristics of the AopB-mediated surface display, experiments were conducted to investigate the effects of the culturing media on the expression levels of AopB$_{172}$-PhoA fusion in C58(pJYH23). As shown in FIG. 10, the expression levels of the AopB$_{172}$-PhoA were similar when C58(pJYH23) was grown in MG/L and IB, but the level was much lower in AB medium. The whole cell ELISA and flow cytometry analysis were then conducted to test the display efficiency of AopB$_{172}$-PhoA for C58(pJYH23) grown in MG/L, AB and IB. As shown in FIG. 11, the AopB$_{172}$-PhoA protein could be efficiently displayed on the cell surface only when the cells were grown in IB medium but not in MG/L and AB medium, although the expression level in MG/L was -similar to that in IB (FIGS. 10, 11 and 12). This suggests that the display of proteins by AopB on the bacterial cell surface was induced by an acidic pH. This could be used as an important factor to control the display of proteins that may have detrimental effects on the outer membrane.

Since *E. coli* is the common host used for various genetic manipulations, it was of interest to test if the aopB display system could be directly used in other bacterium like *E. coli* and *Rhizobium meliloti*. The plasmid pJYH23 encoding the AopB$_{172}$-PhoA was introduced into *E. coli* and *R. meliloti* RCR2011. As shown in FIG. 10, the expression levels of the fusion protein in *E. coli* and *R. meliloti* were similar to that in *A. tumefaciens*, but the fusion protein was not efficiently displayed on the cell surface based on the whole cell ELISA, flow cytometry and protease digestion. The growth of *E. coli* and *R. meliloti* cells in IB medium did not allow *E. coli* or *R. meliloti* to display the fusion protein on the bacterial cell surface, even though the alkaline phosphatase activity could be detected in *E. coli* and *R. meliloti* containing pJYH23 (Table 4), suggesting that the PhoA was directed into the periplasmic space. These suggest that the display of AopB-PhoA fusions on the cell surface might require endogenous factor(s) unique in *A. tumefaciens*. This indicates that the RopB (an AopB homolog) of *R. meliloti* might be used in its native host *R. meliloti* as a carrier for surface display.

TABLE 4

Alkaline phosphatase (AP) activities of AopB$_{172}$-PhoA fusion protein under different culturing conditions

| | | Units of AP activity[a] | | % decrease in AP activity after trypsin treatment[b] |
|---|---|---|---|---|
| Strains | Medium | Without trypsin digestion | After trypsin digestion | |
| C58 | MG/L | 0 | NT[c] | NA[d] |
| | AB | 0 | NT | NA |
| | IB | 0 | NT | NA |
| C58(pJYH23) | MG/L | 952 ± 35 | 868 ± 11 | 9 ± 2 |
| | AB | 490 ± 14 | 442 ± 20 | 10 ± 2 |
| | IB | 3044 ± 80 | 815 ± 27 | 73 ± 2 |
| DH5α | LB | 0 | NT | NA |
| DH5α(pJYH23) | LB | 89 ± 4 | 82 ± 5 | 8 ± 2 |
| RCR2011 | LB/MC | 0 | NT | NA |
| RCR2011(pJYH23) | LB/MC | 460 ± 62 | 417 ± 58 | 9 ± 1 |

[a]The alkaline phosphatase (AP) activities were measured for the bacterial cells harboring pJYH23 (containing the aopB-phoA fusion encoding AopB$_{172}$-PhoA) grown in different media as described in the Materials and Methods. C58, DH5α and RCR2011 were used as the negative controls for C58(pJYH23), DH5α(pJYH23) and RCR2011(pJYH23), respectively.
[b]The decrease of AP activity was expressed as percentage of the activity eliminated by trypsin treatment.
[c]NT, not tested.
[d]NA, not applicable.

Example 8

Surface-Displayed PhoA is Enzymatically Active

To determine whether the PhoA protein displayed on the bacterial cell surface was enzymatically active, the alkaline phosphatase (AP) activity was measured for C58(pJYH23) containing the aopB-phoA fusion grown in different growth media. It has been demonstrated previously that PhoA is enzymatically active only when it is exported across the cytoplasmic membrane into the periplasmic space or onto the outer membrane. As shown in Table 4, the AP activity for the bacterial cells grown in IB was about 3.5 times higher than that in MG/L, while the AopB-PhoA fusion protein expression level for the bacteria grown in IB was slightly lower than that in MG/L (FIG. 10). However, only the bacterial cells grown in IB and not in MG/L exhibited the cell surface display of PhoA (FIGS. 11 and 12). Although the AopB-PhoA produced by the bacterial cells grown in MG/L was not displayed on the cell surface, the fusion protein possessed high AP activity, suggesting that the AopB-PhoA was translocated across the cytoplasmic membrane. The higher AP activity of AopB-PhoA for the bacterial cells grown in IB was presumably due to the easier access of the AP substrate to PhoA and thus faster enzymatic reaction, because the AopB-PhoA of these cells was displayed on the cell surface and the AP substrate was not required to penetrate the outer membrane in order to reach the PhoA protein. This suggests that the PhoA protein displayed on the bacterial cell surface is enzymatically active.

To confirm that the surface displayed AopB-PhoA fusion protein is enzymatically active, experiments were conducted to examine the effects of trypsin treatment on the AP activities of the whole bacterial cells expressing AopB-PhoA. As shown in Table 4, the trypsin digestion could eliminate about 73% of the AP activity of the C58(pJYH23) cells grown in IB medium, while only about 10% of the activity was lost due to the trypsin digestion when the cells were grown in MG/L or AB medium. Previous experiments already demonstrated that the bacterial cells grown in IB but not MG/L or AB could display the PhoA (FIGS. 11 and 12). Since only surface exposed proteins of the whole cells could be accessible to the externally added trypsin, the drastic decrease of the AP activity due to trypsin digestion indicated that the PhoA displayed on the bacterial cell surface was indeed enzymatically active. It was observed that the trypsin digestion could only eliminate about 10% of the AP activities in different bacterial cells, including *A. tumefaciens, E. coli* and *R. meliloti*, when the cells were not displaying the PhoA on the cell surface. The weak decrease of the AP activity in these bacterial cells was presumably due to the possibility that trypsin could digest some proteins of outer membrane pores and then enter into the periplasm to digest the periplasmic PhoA, which was produced by the non-displaying bacterial cells. Nevertheless, all the data consistently indicated that the displayed PhoA was enzymatically active. Since PhoA functions as a homodimer with disulfide bonds, the AopB-based *Agrobacterium* display system represents the first system that can be used to directly display a dimeric protein like PhoA (with disulfide bonds) in an active state.

The references cited in this application are incorporated herein by reference to the extent that they supplement, explain, provide background or teach methods, techniques and/or compositions employed herein.

What is claimed is:

1. An isolated polypeptide comprising (I) an amino acid sequence selected from the group consisting of:
   (a) SEQ ID NO: 2;
   (b) a fragment comprising at least 39 consecutive amino acids from the N-terminus of SEQ ID NO: 2; and
   (c) a variant of (a) or (b) that:
      (i) is at least 65% identical in amino acid sequence to the polypeptide of (a) or (b); and
      (ii) is localized to the outer membrane when the variant is expressed in a gram-negative bacterium cell; and
   (II) a passenger protein.

2. The polypeptide of claim 1 wherein the fragment comprising at least 39 consecutive amino acids from the N-terminus of SEQ ID No: 2 comprises at least the N-terminal 125 amino acids of SEQ ID No:2.

3. The polypeptide of claim 1 wherein the fragment comprising at least 39 consecutive amino acids from the N-terminus of SEQ ID No: 2 comprises at least the N-terminal 134 amino acids of SEQ ID No:2.

4. The polypeptide of claim 1 wherein the fragment comprising at least 39 consecutive amino acids from the N-terminus of SEQ ID No: 2 comprises at least the N-terminal 172 amino acids of SEQ ID No:2.

5. The polypeptide of claim 1 wherein the fragment comprising at least 39 consecutive amino acids from the N-terminus of SEQ ID No: 2 comprises at least the N-terminal 183 amino acids of SEQ ID No:2.

6. The polypeptide of claim 1 wherein the fragment comprising at least 39 consecutive amino acids from the N-terminus of SEQ ID No: 2 comprises at least the N-terminal 207 amino acids of SEQ ID No:2.

7. The polypeptide of claim 1, in which the amino acid sequence (I) is (c) a variant of (a) or (b) that is at least 90% identical in amino acid sequence to the polypeptide of (a) or (b).

8. The peptide of claim 1, in which the passenger protein is a disulfide-linked protein.

9. An isolated polypeptide comprising (I) an amino acid sequence selected from the group consisting of:
   (a) SEQ ID NO: 4 and a signal peptide functional in a bacterial cell joined to the amino terminus thereof;
   (b) a fragment comprising at least 16 consecutive amino acids from the N-terminus of SEQ ID NO: 4 and a signal peptide that is functional in a bacterial cell joined to the amino terminus thereof; and
   (c) a variant of (a) or (b) that:
      (i) is at least 65% identical in amino acid sequence to the polypeptide of (a) or (b) that is represented by SEQ ID NO: 4; and
      (ii) is localized to the outer membrane when the variant is: (1) joined in-frame with a bacterial secretion signal and, (2) produced in a gram-negative bacterium cell; and (II) a passenger protein.

10. The polypeptide of claim 9 wherein the fragment comprising at least 16 consecutive amino acids from the N-terminus of SEQ ID No:4 comprises at least the N-terminal 102 amino acids of SEQ ID No:4.

11. The polypeptide of claim 9 wherein the fragment comprising at least 16 consecutive amino acids from the N-terminus of SEQ ID No:4 comprises at least the N-terminal 111 amino acids of SEQ ID No:4.

12. The polypeptide of claim 9 wherein the fragment comprising at least 16 consecutive amino acids from the N-terminus of SEQ ID No:4 comprises at least the N-terminal 149 amino acids of SEQ ID No:4.

13. The polypeptide of claim 9 wherein the fragment comprising at least 16 consecutive amino acids from the N-terminus of SEQ ID No:4 comprises at least the N-terminal 160 amino acids of SEQ ID No:4.

14. The polypeptide of claim 9 wherein the fragment comprising at least 16 consecutive amino acids from the N-terminus of SEQ ID No:4 comprises at least the N-terminal 184 amino acids of SEQ ID No:4.

15. The polypeptide of claim 9, in which the amino acid sequence (I) is (c) a variant of (a) or (b) that is at least 90% identical in amino acid sequence to the polypeptide of (a) or (b).

16. The peptide of claim 9, in which the passenger protein is a disulfide-linked protein.

17. A method of producing a microorganism on whose surface is displayed a passenger protein, the method comprising the steps of:
I) introducing an expression vector into a microorganism to obtain a transformed microorganism; and
II) culturing the transformed microorganism obtained from step (I) to express the protein;
wherein the expression vector comprises:
(a) a nucleic acid encoding a carrier protein, wherein the carrier protein is selected from the group consisting of:
  i) a polypeptide comprising an amino acid sequence selected from the group consisting of:
    (1) SEQ ID NO: 2;
    (2) a fragment comprising at least 39 consecutive amino acids from the N-terminus of SEQ ID NO: 2; and
    (3) a variant of (1) or (2) that:
      (aa) is at least 65% identical in amino acid sequence to the polypeptide of (1) or (2); and
      (bb) is localized to the outer membrane when the variant is expressed in a gram-negative bacterium cell;
  ii) a polypeptide comprising an amino acid sequence selected from the group consisting of:
    (4) SEQ ID NO: 4 and a signal peptide that is functional in a bacterial cell joined to the amino terminus thereof;
    (5) a fragment comprising at least 16 consecutive amino acids from the N-terminus of SEQ ID NO: 4 and a signal peptide that is functional in a bacterial cell joined to the amino terminus thereof; and
    (6) a variant of (4) or (5) that:
      (cc) is at least 65% identical in amino acid sequence to the polypeptide of (4) or (5) in the portion represented by SEQ ID NO: 4; and
      (dd) is localized to the outer membrane when the variant is joined in-frame with a bacterial secretion signal and produced in a gram-negative bacterium cell; and (iii) a member of the AopB-related outer membrane protein family; wherein the carrier protein is display-compatible with the microorganism and wherein the carrier protein contains a bacterial secretion signal functional in the microorganism;
(b) a nucleic acid encoding a passenger protein, which nucleic acid being joined in frame with, and 3' of, the nucleic acid encoding the carrier protein; and
(c) expression control sequences operably linked to the nucleic acid encoding the carrier protein, wherein the expression control sequences are suitable for expressing the nucleic acid encoding the carrier protein in the microorganism.

18. The method of claim 17 wherein the expression control sequences comprise an AopB promoter.

19. The method of claim 17 wherein the microorganism is cultured under acidic pH conditions.

20. The method according to claim 17 wherein the carrier protein is a polypeptide comprising an amino acid sequence selected from the group consisting of:
(a) SEQ ID NO: 2;
(b) a fragment comprising at least 39 consecutive amino acids from the N-terminus of SEQ ID NO: 2; and
(c) a variant of (a) or (b) that:
  (i) is at least 65% identical in amino acid sequence to the peptide (a) or (b); and
  (ii) is localized to the outer membrane when the variant is expressed in a gram-negative bacterium cell; and
wherein the microorganism is *Agrobacterium*.

21. The method according to claim 20 wherein the *Agrobacterium* is *A. tumefaciens*.

22. The method according to claim 17 further comprising the step of:
(III) determining if the cultured microorganism obtained from step (II) presents the passenger protein on the surface of the microorganism and selecting those organisms with the passenger protein on the surface.

23. The method of claim 22 wherein the determining step comprises fluorescence-activated cell sorting (FACS).

24. The method according to claim 17 in which the carrier protein is (ii) and the display-compatible microorganism is *Agrobacterium*.

25. The method according to claim 17 wherein the carrier protein is a polypeptide comprising an amino acid sequence selected from the group consisting of:
(a) SEQ ID NO: 4 and a signal peptide that is functional in a bacterial cell joined to the amino terminus thereof;
(b) a fragment comprising at least 16 consecutive amino acids from the N-terminus of SEQ ID NO: 4 and a signal peptide that is functional in a bacterial cell joined to the amino terminus thereof; and
(c) a variant of (a) or (b) that:
  (i) is at least 65% identical in amino acid sequence to the corresponding polypeptide of (a) or (b) in the portion represented by SEQ ID NO: 4; and
  (ii) is localized to the outer membrane when the variant is: (1) joined in-frame with a bacterial secretion signal and, (2) produced in a gram-negative bacterium cell; and wherein the microorganism is *Agrobacterium*.

26. The method of claim 17, in which the carrier protein is selected from the group consisting of the polypeptide fragment comprising at least 125 consecutive amino acids from the N-terminus of SEQ ID No: 2, the polypeptide fragment comprising at least 134 consecutive amino acids from the N-terminus of SEQ ID No: 2, the polypeptide fragment comprising at least 172 consecutive amino acids from the N-terminus of SEQ ID No: 2, the polypeptide fragment comprising at least 183 consecutive amino acids from the N-terminus of SEQ ID No: 2, the polypeptide fragment comprising at least 207 consecutive amino acids from the N-terminus of SEQ ID No: 2, the polypeptide fragment comprising at least 102 consecutive amino acids from the N-terminus of SEQ ID No:4, the polypeptide fragment comprising at least 111 consecutive amino acids from the N-terminus of SEQ ID No:4, the polypeptide fragment comprising at least 149 consecutive amino acids from the N-terminus of SEQ ID No:4, the polypeptide fragment comprising at least 160 consecutive amino acids from the N-terminus of SEQ ID No:4 and the polypeptide fragment comprising at least 184 consecutive amino acids from the N-terminus of SEQ ID No:4;

and wherein said microorganism is an *Agrobacterium*.

27. The method of claim 17, in which the carrier protein is (ii).

28. The method of claim 17, in which the amino acid sequence (i) is a variant of (1) or (2) that is at least 90% identical in amino acid sequence to the polypeptide of (1) or (2) or the amino acid sequence (ii) is a variant of (4) or (5) that is at least 90% identical in amino acid sequence to the polypeptide of (4) or (5).

29. The method of claim 20, in which the carrier protein has an amino acid sequence that is a variant of (a) or (b) that is at least 90% identical in amino acid sequence to the polypeptide of (a) or (b).

30. The method of claim 25, in which the carrier protein has an amino acid sequence that is a variant of (a) or (b) that is at least 90% identical in amino acid sequence to the polypeptide of (a) or (b).

31. The method of claim 17, in which the passenger protein is a disulfide-linked protein.

32. The method of claim 28, in which the passenger protein is a disulfide-linked protein.

33. The method of claim 17, in which the passenger protein forms a dimer or multimer when localized at the outer membrane.

34. The method of claim 28, in which the passenger protein forms a dimer or a multimer when localized at the outer membrane.

35. A method of producing a microorganism on whose surface is displayed a passenger protein, the method comprising the steps of:
   I) introducing an expression vector into a microorganism to obtain a transformed microorganism; and
   II) culturing the transformed microorganism obtained from step (I) to express the protein;
   wherein the expression vector comprises:
      a) a nucleic acid encoding a carrier protein that consists of an amino terminal fragment of from 150 to 220 consecutive amino acids of a protein that is a member of the AopB-related outer membrane protein family; wherein the carrier protein is display-compatible with the microorganism and wherein the carrier protein contains a bacterial secretion signal functional in the microorganism;
      b) a nucleic acid encoding a passenger protein, which nucleic acid being joined in frame with, and 3' of, the nucleic acid encoding the carrier protein; and
      c) expression control sequences operably linked to the nucleic acid encoding the carrier protein, wherein the expression control sequences are suitable for expressing the nucleic acid encoding the carrier protein in the microorganism.

36. The method according to claim 35, wherein the carrier protein and the microorganism are selected from the group consisting of:
   (a) the carrier protein which consists of from 150 to 220 consecutive amino acids from the N-terminus of the RopB polypeptide sequence and the display-compatible microorganism which is *Rhizobium*,
   (b) the carrier protein which consists of from 150 to 220 consecutive amino acids from the N-terminus of an outer membrane protein sequence of *Brucella* and the display-compatible microorganism which is *Brucella*,
   (c) the carrier protein which consists of from 150 to 220 consecutive amino acids from the N-terminus of the Pap31polypeptide sequence and the display-compatible microorganism which is *Bartonella*,
   (d) the carrier protein which consists of from 150 to 220 consecutive amino acids from the N-terminus of the PomA polypeptide sequence and the display-compatible microorganism which is *Pasteurella* (*Mannheimia*),
   (e) the carrier protein which consists of from 150 to 220 consecutive amino acids, from the N-terminus of the PPE polypeptide sequence and the display-compatible microorganism which is *Mycobacterium*,
   (f) the carrier protein which consists of from 150 to 220 consecutive amino acids from the N-terminus of the major outer membrane protein sequence and the display-compatible microorganism which is *Haemophilus*, and
   (g) the carrier protein which consists of from 150 to 220 consecutive amino acids from the N-terminus of the outer membrane porin polypeptide sequence and the display-compatible microorganism which is *Vibrio*.

37. The method according to claim 36 further comprising the step of:
   (III) determining if the cultured microorganism obtained from step (II) presents the passenger protein on the surface of the microorganism and selecting those organisms with the passenger protein on the surface.

38. The method of claim 36, in which the passenger protein is a disulfide-linked protein.

39. The method of claim 35, in which the passenger protein is a disulfide-linked protein.

40. The method of claim 36, in which the passenger protein forms a dimer or a multimer when localized at the outer membrane.

41. The method of claim 35, in which the passenger protein forms a dimer or a multimer when localized at the outer membrane.

42. A method for expressing a fusion protein on the surface of *Agrobacterium*, the method comprising the steps of:
   (I) introducing a vector into a bacterium of the *Agrobacterium* genus; and
   (II) culturing the bacterium obtained from step (I) to express the fusion protein;
   wherein the vector comprises:
      (a) a nucleic acid sequence which encodes a fusion protein comprising a first polypeptide comprising an amino acid sequence selected from the group consisting of:
         (1) SEQ ID NO: 2;
         (2) a fragment comprising at least 39 consecutive amino acids from the N-terminus of SEQ ID NO: 2; and
         (3) a variant of (1) or (2) that:
            (i) is at least 65% identical in amino acid sequence to the corresponding polypeptide of (1) or (2); and
            (ii) is localized to the outer membrane when the variant is expressed in a gram-negative bacterium cell;

and a second polypeptide,
wherein the fusion protein contains a bacterial secretion signal; and
  (b) expression control sequences operably linked to the nucleic acid encoding the fusion protein, wherein the expression control sequences are suitable for expressing the nucleic acid encoding the fusion protein in *Agrobacterium*.

43. The method of claim 42, in which the second polypeptide is fused to the C-terminus of the first polypeptide.

44. The method of claim 42, in which the amino acid sequence of the first polypeptide is a variant of (1) or (2) that is at least 90% identical in amino acid sequence to the polypeptide of (1) or (2).

* * * * *

SEQUENCE LISTING

```
<160> NUMBER OF SEQ ID NOS: 13

<210> SEQ ID NO 1
<211> LENGTH: 1435
<212> TYPE: DNA
<213> ORGANISM: Agrobacterium tumefaciens
<220> FEATURE:
<221> NAME/KEY: CDS
<222> LOCATION: (316)..(969)
<220> FEATURE:
<221> NAME/KEY: misc_feature
<222> LOCATION: (316)..(384)
<223> OTHER INFORMATION: encodes putative signal sequence
```

<400> SEQUENCE: 1

```
ctagctgtca ctcagctcca aaagaattgg gcgattttc attcacaatg caatttcggt      60
ttaatttgaa tataactaag tttaaaggcg atctattgct ggttaggctt ctgttagggt    120
taatataacc cttgtggcaa ttaggcaacg tctaattcta gtcacgtctc tgccccaaac    180
aattcacatt ttggctcttt gatctccgca ttctcccatc aagttcagtt tccagagggg    240
caaattaacc cgacgatttt taccgcgtct gaaaacaatg ttttgagtgc agagcggtcc    300
tgaaaggaga ataac atg cgt att ttc gta gca acc ctt atg gct tcg acc    351
                 Met Arg Ile Phe Val Ala Thr Leu Met Ala Ser Thr
                  1               5                  10 atg gca gcc gcc ggt ttt tcg gct gct tac gcc gcc gac gcc gta aat    399
Met Ala Ala Ala Gly Phe Ser Ala Ala Tyr Ala Ala Asp Ala Val Asn
         15                  20                  25 gag gtg ccg cag gca ccg gta gcc tac gac cag ccc gcc gcg gtc aag    447
Glu Val Pro Gln Ala Pro Val Ala Tyr Asp Gln Pro Ala Ala Val Lys
     30                  35                  40 gat tgg tcc ggc gcc tac ctc ggt ggt acg gtc aac tat gac tgg ggc    495
Asp Trp Ser Gly Ala Tyr Leu Gly Gly Thr Val Asn Tyr Asp Trp Gly
 45                  50                  55                  60 cgt ttc agc tcc agc aat gac ggt cgt gac gcc aag ggc ttc ggt ggc    543
Arg Phe Ser Ser Ser Asn Asp Gly Arg Asp Ala Lys Gly Phe Gly Gly
                 65                  70                  75 ggc gtc tat ggt ggt tac aac atg cag agc ggc cag atc gtt tac ggt    591
Gly Val Tyr Gly Gly Tyr Asn Met Gln Ser Gly Gln Ile Val Tyr Gly
         80                  85                  90 gct gaa gca gac gtg aac atg ggc gac gag aag ggc tcc gcc ggt acg    639
Ala Glu Ala Asp Val Asn Met Gly Asp Glu Lys Gly Ser Ala Gly Thr
     95                 100                 105 gtt gcc ggt cgc gcc gtc gaa ggc aag cag ggc gtc aac ggc tcg ctg    687
Val Ala Gly Arg Ala Val Glu Gly Lys Gln Gly Val Asn Gly Ser Leu
    110                 115                 120 cgt ggc cgc gtc ggt tac gac atg aac ccg ttc ctg ctt tat ggt acg    735
Arg Gly Arg Val Gly Tyr Asp Met Asn Pro Phe Leu Leu Tyr Gly Thr
125                 130                 135                 140 gcc ggt ctt gct gtc tcc gac aac aag gtt cgt gac ggc gtc aac aag    783
Ala Gly Leu Ala Val Ser Asp Asn Lys Val Arg Asp Gly Val Asn Lys
                145                 150                 155 gac agc gcc acg gct ctc ggt tac acg gtt ggc gcc ggt gtt gaa gcc    831
Asp Ser Ala Thr Ala Leu Gly Tyr Thr Val Gly Ala Gly Val Glu Ala
        160                 165                 170 atg gtg acc gac aac atc acc gct cgt ctg gaa tat cgc tac agc gat    879
Met Val Thr Asp Asn Ile Thr Ala Arg Leu Glu Tyr Arg Tyr Ser Asp
    175                 180                 185 tac cag aag aag gac tac acg ctc ggc aac gat gcc ttc tcg cgt ggt    927
Tyr Gln Lys Lys Asp Tyr Thr Leu Gly Asn Asp Ala Phe Ser Arg Gly
    190                 195                 200 ttt gac gac cac tcg gtc aag gcc ggt atc ggc gtc aag ttc                969
Phe Asp Asp His Ser Val Lys Ala Gly Ile Gly Val Lys Phe
205                 210                 215 tgatccttct cggatcggtc aaggaaaagc cggggtttac gccccggctt ttttttgttt   1029
ctgtgatttg ccatcgcctt aacgcccggt ggaaagaacc gggcgttttg ttcggcgggt   1089
ctaggcggcg gctttcattt ccgcataggc gtcgaaacgc ttgccgaagg tttctggcca   1149
ggctgccagc gcatcacgtc cctcggccca ctcaccggca aaacgcaggt cgagatagcc   1209
gatcatcgct gcaagggcga aatggccgcc atgcagcttc ttgccggttt tcggcaggtt   1269
ggcgttgagg tgatcgagcc cgcggaccac cttgctccac tgcttgtcga tccacggctg   1329
```

```
atgaatcttg tcttccgggc ggaaacgccg ctcgtagacg atggcgagca ggcaatccat    1389
gatgccgtcg cacagagctt ccagaatttc cgcttcagtg cgctag                   1435
```

<210> SEQ ID NO 2
<211> LENGTH: 218
<212> TYPE: PRT
<213> ORGANISM: Agrobacterium tumefaciens

<400> SEQUENCE: 2

```
Met Arg Ile Phe Val Ala Thr Leu Met Ala Ser Thr Met Ala Ala Ala
1               5                   10                  15

Gly Phe Ser Ala Ala Tyr Ala Ala Asp Ala Val Asn Glu Val Pro Gln
            20                  25                  30

Ala Pro Val Ala Tyr Asp Gln Pro Ala Ala Val Lys Asp Trp Ser Gly
        35                  40                  45

Ala Tyr Leu Gly Gly Thr Val Asn Tyr Asp Trp Gly Arg Phe Ser Ser
    50                  55                  60

Ser Asn Asp Gly Arg Asp Ala Lys Gly Phe Gly Gly Val Tyr Gly
65                  70                  75                  80

Gly Tyr Asn Met Gln Ser Gly Gln Ile Val Tyr Gly Ala Glu Ala Asp
                85                  90                  95

Val Asn Met Gly Asp Glu Lys Gly Ser Ala Gly Thr Val Ala Gly Arg
            100                 105                 110

Ala Val Glu Gly Lys Gln Gly Val Asn Gly Ser Leu Arg Gly Arg Val
        115                 120                 125

Gly Tyr Asp Met Asn Pro Phe Leu Leu Tyr Gly Thr Ala Gly Leu Ala
    130                 135                 140

Val Ser Asp Asn Lys Val Arg Asp Gly Val Asn Lys Asp Ser Ala Thr
145                 150                 155                 160

Ala Leu Gly Tyr Thr Val Gly Ala Gly Val Glu Ala Met Val Thr Asp
                165                 170                 175

Asn Ile Thr Ala Arg Leu Glu Tyr Arg Tyr Ser Asp Tyr Gln Lys Lys
            180                 185                 190

Asp Tyr Thr Leu Gly Asn Asp Ala Phe Ser Arg Gly Phe Asp Asp His
        195                 200                 205

Ser Val Lys Ala Gly Ile Gly Val Lys Phe
    210                 215
```

<210> SEQ ID NO 3
<211> LENGTH: 585
<212> TYPE: DNA
<213> ORGANISM: Agrobacterium tumefaciens
<220> FEATURE:
<221> NAME/KEY: CDS
<222> LOCATION: (1)..(585)
<220> FEATURE:
<221> NAME/KEY: misc_feature
<222> LOCATION: (1)..(585)
<223> OTHER INFORMATION: aopB without signal sequence

<400> SEQUENCE: 3

```
gcc gac gcc gta aat gag gtg ccg cag gca ccg gta gcc tac gac cag    48
Ala Asp Ala Val Asn Glu Val Pro Gln Ala Pro Val Ala Tyr Asp Gln
1               5                   10                  15 ccc gcc gcg gtc aag gat tgg tcc ggc gcc tac ctc ggt ggt acg gtc    96
Pro Ala Ala Val Lys Asp Trp Ser Gly Ala Tyr Leu Gly Gly Thr Val
            20                  25                  30 aac tat gac tgg ggc cgt ttc agc tcc agc aat gac ggt cgt gac gcc   144
Asn Tyr Asp Trp Gly Arg Phe Ser Ser Ser Asn Asp Gly Arg Asp Ala
```

```
                Asn Tyr Asp Trp Gly Arg Phe Ser Ser Asn Asp Gly Arg Asp Ala
                     35                  40                  45 aag ggc ttc ggt ggc ggc gtc tat ggt ggt tac aac atg cag agc ggc          192
Lys Gly Phe Gly Gly Gly Val Tyr Gly Gly Tyr Asn Met Gln Ser Gly
 50                  55                  60 cag atc gtt tac ggt gct gaa gca gac gtg aac atg ggc gac gag aag          240
Gln Ile Val Tyr Gly Ala Glu Ala Asp Val Asn Met Gly Asp Glu Lys
 65                  70                  75                  80 ggc tcc gcc ggt acg gtt gcc ggt cgc gcc gtc gaa ggc aag cag ggc          288
Gly Ser Ala Gly Thr Val Ala Gly Arg Ala Val Glu Gly Lys Gln Gly
                 85                  90                  95 gtc aac ggc tcg ctg cgt ggc cgc gtc ggt tac gac atg aac ccg ttc          336
Val Asn Gly Ser Leu Arg Gly Arg Val Gly Tyr Asp Met Asn Pro Phe
                100                 105                 110 ctg ctt tat ggt acg gcc ggt ctt gct gtc tcc gac aac aag gtt cgt          384
Leu Leu Tyr Gly Thr Ala Gly Leu Ala Val Ser Asp Asn Lys Val Arg
            115                 120                 125 gac ggc gtc aac aag gac agc gcc acg gct ctc ggt tac acg gtt ggt          432
Asp Gly Val Asn Lys Asp Ser Ala Thr Ala Leu Gly Tyr Thr Val Gly
        130                 135                 140 gcc ggt gtt gaa gcc atg gtg acc gac aac atc acc gct cgt ctg gaa          480
Ala Gly Val Glu Ala Met Val Thr Asp Asn Ile Thr Ala Arg Leu Glu
145                 150                 155                 160 tat cgc tac agc gat tac cag aag aag gac tac acg ctc ggc aac gat          528
Tyr Arg Tyr Ser Asp Tyr Gln Lys Lys Asp Tyr Thr Leu Gly Asn Asp
                165                 170                 175 gcc ttc tcg cgt ggt ttt gac gac cac tcg gtc aag gcc ggt atc ggc          576
Ala Phe Ser Arg Gly Phe Asp Asp His Ser Val Lys Ala Gly Ile Gly
            180                 185                 190 gtc aag ttc                                                              585
Val Lys Phe
        195

<210> SEQ ID NO 4
<211> LENGTH: 195
<212> TYPE: PRT
<213> ORGANISM: Agrobacterium tumefaciens

<400> SEQUENCE: 4

Ala Asp Ala Val Asn Glu Val Pro Gln Ala Pro Val Ala Tyr Asp Gln
1               5                  10                  15

Pro Ala Ala Val Lys Asp Trp Ser Gly Ala Tyr Leu Gly Gly Thr Val
                20                  25                  30

Asn Tyr Asp Trp Gly Arg Phe Ser Ser Asn Asp Gly Arg Asp Ala
         35                  40                  45

Lys Gly Phe Gly Gly Gly Val Tyr Gly Gly Tyr Asn Met Gln Ser Gly
 50                  55                  60

Gln Ile Val Tyr Gly Ala Glu Ala Asp Val Asn Met Gly Asp Glu Lys
 65                  70                  75                  80

Gly Ser Ala Gly Thr Val Ala Gly Arg Ala Val Glu Gly Lys Gln Gly
                 85                  90                  95

Val Asn Gly Ser Leu Arg Gly Arg Val Gly Tyr Asp Met Asn Pro Phe
                100                 105                 110

Leu Leu Tyr Gly Thr Ala Gly Leu Ala Val Ser Asp Asn Lys Val Arg
            115                 120                 125

Asp Gly Val Asn Lys Asp Ser Ala Thr Ala Leu Gly Tyr Thr Val Gly
        130                 135                 140
```

```
Ala Gly Val Glu Ala Met Val Thr Asp Asn Ile Thr Ala Arg Leu Glu
145                 150                 155                 160

Tyr Arg Tyr Ser Asp Tyr Gln Lys Lys Asp Tyr Thr Leu Gly Asn Asp
                165                 170                 175

Ala Phe Ser Arg Gly Phe Asp Asp His Ser Val Lys Ala Gly Ile Gly
            180                 185                 190

Val Lys Phe
    195

<210> SEQ ID NO 5
<211> LENGTH: 24
<212> TYPE: DNA
<213> ORGANISM: Artificial Sequence
<220> FEATURE:
<223> OTHER INFORMATION: Primer p54

<400> SEQUENCE: 5
gcaaatcgct agctgtcact cagc                                       24

<210> SEQ ID NO 6
<211> LENGTH: 24
<212> TYPE: DNA
<213> ORGANISM: Artificial Sequence
<220> FEATURE:
<223> OTHER INFORMATION: Primer p55

<400> SEQUENCE: 6
agaacggcta gcgcactgaa gcgg                                       24

<210> SEQ ID NO 7
<211> LENGTH: 24
<212> TYPE: DNA
<213> ORGANISM: Artificial Sequence
<220> FEATURE:
<223> OTHER INFORMATION: Primer p119

<400> SEQUENCE: 7
aaatcgatct attgctggtt aggc                                       24

<210> SEQ ID NO 8
<211> LENGTH: 24
<212> TYPE: DNA
<213> ORGANISM: Artificial Sequence
<220> FEATURE:
<223> OTHER INFORMATION: Primer p112

<400> SEQUENCE: 8
cgactgcaga aggatcagaa cttg                                       24

<210> SEQ ID NO 9
<211> LENGTH: 54
<212> TYPE: DNA
<213> ORGANISM: Artificial Sequence
<220> FEATURE:
<223> OTHER INFORMATION: Primer p118

<400> SEQUENCE: 9
ccggtaccgg atcctgcagc tagcaagctt caacaccggc accaaccgtg taac        54

<210> SEQ ID NO 10
<211> LENGTH: 27
<212> TYPE: DNA
<213> ORGANISM: Artificial Sequence
<220> FEATURE:
```

```
<223> OTHER INFORMATION: Primer GFPuvFh3

<400> SEQUENCE: 10
gggaagcttg gagtaaagga gaagaac                                         27

<210> SEQ ID NO 11
<211> LENGTH: 24
<212> TYPE: DNA
<213> ORGANISM: Artificial Sequence
<220> FEATURE:
<223> OTHER INFORMATION: Primer GFPuvRp1

<400> SEQUENCE: 11
aactgcagtc attatttgta gagc                                            24

<210> SEQ ID NO 12
<211> LENGTH: 32
<212> TYPE: DNA
<213> ORGANISM: Artificial Sequence
<220> FEATURE:
<223> OTHER INFORMATION: Primer PhoAfH3

<400> SEQUENCE: 12
gggaagcttc tgactcttat acacaagtag cg                                   32

<210> SEQ ID NO 13
<211> LENGTH: 29
<212> TYPE: DNA
<213> ORGANISM: Artificial Sequence
<220> FEATURE:
<223> OTHER INFORMATION: Primer PhoAreP1

<400> SEQUENCE: 13
ggctgcagtt atttcagccc cagagcggc                                       29
```